(12) United States Patent
Zuo et al.

(10) Patent No.: US 8,119,369 B2
(45) Date of Patent: Feb. 21, 2012

(54) HUMAN SUMO-3 FOR ENHANCING PROTEIN EXPRESSION

(75) Inventors: Xun Zuo, Malvern, PA (US); David E. Sterner, Lansdowne, PA (US); Tauseef R. Butt, Malvern, PA (US)

(73) Assignee: Lifesensors, Inc., Malvern, PA (US)

( * ) Notice: Subject to any disclaimer, the term of this patent is extended or adjusted under 35 U.S.C. 154(b) by 389 days.

(21) Appl. No.: 11/794,532

(22) PCT Filed: Dec. 30, 2005

(86) PCT No.: PCT/US2005/047210
§ 371 (c)(1),
(2), (4) Date: May 18, 2009

(87) PCT Pub. No.: WO2006/073976
PCT Pub. Date: Jul. 13, 2006

(65) Prior Publication Data
US 2010/0021987 A1 Jan. 28, 2010

Related U.S. Application Data

(60) Provisional application No. 60/640,107, filed on Dec. 30, 2004.

(51) Int. Cl.
*C12P 21/04* (2006.01)
*C07H 21/04* (2006.01)

(52) U.S. Cl. ............. 435/69.7; 435/71.1; 536/23.4

(58) Field of Classification Search ................. None
See application file for complete search history.

(56) References Cited

U.S. PATENT DOCUMENTS

| 6,596,527 B1 | 7/2003 | Yeh et al. |
| 2003/0086918 A1* | 5/2003 | Lima et al. .......... 424/94.63 |
| 2003/0153045 A1 | 8/2003 | Butt et al. |

FOREIGN PATENT DOCUMENTS

| WO | 03/057174 A3 | 7/2003 |
| WO | 2004/030615 A | 4/2004 |

OTHER PUBLICATIONS

Su et al., "Molecular features of human ubiquitin-like SUMO genes and their encoded proteins", Gene, 2002, 296: 65-73.*
Zhang et al. "Enzymes of the SUMO Modification Pathway Localize to Filaments of the Nuclear Pore Complex", Mol. Cell. Biol., 2002, 22(18):6498-6508.*
Malakhov et al., SUMO Fusions and SUMO-specific Protease for Efficient Expression and Purification of Proteins, Journal of Structural and Functional Genomics, 2004, 5:75-86.

* cited by examiner

*Primary Examiner* — Suzanne M Noakes
(74) *Attorney, Agent, or Firm* — Dann, Dorfman, Herrell & Skillman; Robert C. Netter, Jr.

(57) ABSTRACT

The inventive subject matter relates to novel compositions, methods, and kits for enhancing the expression, solubility, and isolation of heterologous proteins. Further, the inventive subject matter relates to methods for generating proteins with novel N-terminal amino acids, unlike wild-type proteins which always are translated from mRNA with methionine at the N-terminus.

24 Claims, 13 Drawing Sheets

```
PfUlp   ------GSYNYSKVSRWTKRKQVDIPSF---DLLLIPLHVGGNEWTLGSI------
AnUlp   ------GYDSVKRMAKRAKIGGKDLLDVDTVFIFVHNK-AEWTLIVV-------- yUlp1   ----------
yUlp2   ----------
hSENP1  ----------
hSENP2  ----------
hSENP3  ----------
hSENP5  ----------
hSENP6  VIKRMLNKKECIAVIDSNPGQEBSDPRYKRNICSVKISVKKINHTASENEEFNKGESTSQKVADRTKSENGLQNESLSSTHHTDGLSKIRLNYSDESPEAGKM
hSENP7  ------------------------------------------------------QTVSQQS
AtULP1a ----------
AtULP1b ----------
AtULP1c ----------
AtULP1d ----------
AtESD4  ----------
XopD    ----------
XSENP1a ----------
DmUlp1  ----------
CeUlp-1 ----------
CeUlp-2 ----------
SpUlp1  ----------
SpUlp2  ----------
KlUlp1  ----------
PfUlp   ----------
AnUlp   ---------- yUlp1   -------------------DLAKKCTIGYVDSLSNGP-NAMSFAILTDIQKYVMEESKHTIGEDFDLIHLDC-----
yUlp2   ---TNLDAILDFHQNKDKEDALNSDEISIRMPIVNILTFDSLRQTH-SREIDPIKEFLISTALDKYSIQLDKTQIKMKTCP-----
hSENP1  -------------------DFRKKMITYDSMGGIN-MEACRLLQTLAQBSIDKKRKGEFDTNGWQLFSKAGSQ-----
hSENP2  -------------------DLRKKCLAYLDSNGQKG-HRICEILLQTLQDESKTKRNSDLNLLEWTHHSMKPHE
hSENP3  -------------------DVRRRITTYFDSQRTLN-RRCPKHTAKYIQABAVKKDRLDFEQGMKGYFRMN-----
hSENP5  -------------------TLSMRIISFVDSQGIHF-KPCVENIRKYLJTEAPKIKNRPEFLQGMQZAVTKC-----
hSENP6  LEDELVDFSEQDNQDDSSDDGFLADDNCSSETGQWMELKPYTICKQPCILLMDSLRGPSRNVVCILREYLEVEWEVAKGSKRSFSKDVNKGSRPK-----
hSENP7  QAQQSQSDNKTIDNDLRTTSTLSLSAEDSQSTEBSMSVPKKWCKRPCILLILDSLKAASVRNTVQMREYLEVEWEVKLKTERQFSKINNVDLCPK-----
AtULP1a -------------------WIKDQFQYLDSFRGRE-PKILALARYFVDEVRDKSEVDLLDVSRMRQEFVQD-----
AtULP1b -------------------NNRERKFVYLDSLFTGVGHTILANAKIVDEVKQKSQKMIDVSSWGMEYVEB-----
AtULP1c -------------------DBSGLATIIHLDSLGLHPFELLIFNVGRFLREEMWYLAQD-APLDLPLSAKVWRDLPRM--IN
AtULP1d -------------------NHRRSKLLYLDSLWQVD-PHCLNFALAKYMGDBANEKSGKLIDANSWDMEPVED-----
AtESD4  -------------------NNRRSKLLYLDSLNGVD-PHCLNFALAKYMGDBANEKSGKLIDANSWDMEPVED-----
XopD    -------------------DRRHDAVAAYHYDSMAQKD-PCQ-----RYLADMAAVHLGLDYQQTHEMP-----
XSENP1a -------------------DLRKKSITYFDSNGGLM-NDACRLLQYLKQESVDKRGACFDSRGWTLTCKYSEE
DmUlp1  -------------------HLRMKTIFYYDSMGRPM-QFALDALVKYHRRSLDKRKQPFDWTGFVVERAQW-----
CeUlp-1 -------------------DMGERKCIEFYDSLYDGF-TAVLPALRGYLRABSLDKKKEAMWFSGWTIQQMTD
```

Figure 1B. (cont'd)

```
          BglII
          ~~~~~~
    1     AGATCTCGATCCCGCGAAATTAATACGACTCACTATAGGGGAATTGTGAG

XbaI
                ~~~~~~
    51    CGGATAACAATTCCCCTCTAGAAATAATTTTGTTTAACTTTAAGAAGGAG

NcoI
                ~~~~~~
                MetGlyHisHisHisHisHisHisGlyGlySerGluGluLysP
    101   ATATACCATGGGTCATCACCATCATCATCACGGAGGTTCCGAGGAGAAGC roLysGluGlyValLysThrGluAsnAspHisIleAsnLeuLysValAla
    151   CCAAGGAGGGTGTGAAGACAGAGAATGACCACATCAACCTGAAGGTGGCC

GlyGlnAspGlySerValValGlnPheLysIleLysArgHisThrProLe
    201   GGGCAGGACGGCTCCGTGGTGCAGTTCAAGATCAAGAGGCACACGCCGCT uSerLysLeuMetLysAlaTyrCysGluArgGlnGlyLeuSerMetArgG
    251   GAGCAAGCTGATGAAGGCCTACTGCGAGAGGCAGGGCTTGTCAATGAGGC lnIleArgPheArgPheAspGlyGlnProIleAsnGluThrAspThrPro
    301   AGATCAGATTCAGGTTCGACGGGCAGCCAATCAATGAAACTGACACTCCA

AlaGlnLeuGluMetGluAspGluAspThrIleAspValPheGlnGlnGl
    351   GCACAGCTGGAGATGGAGGACGAGGACACCATCGACGTGTTCCAGCAGCA

BsaI  BamHI  EcoRI   SacI    SalI HindIII
                        ~~~~~~~~~~~~~~~~~~~~~~~~~~~  ~~~~~~~~~~~~~~
          nThrGlyGly***
    401   GACGGGAGGTTGAGACCGGATCCGAATTCGAGCTCCGTCGACAAGCTTGC
                         ↑
          Hydrolase Cleavage Site NotI
          EagI        XhoI
          ~~~~~~      ~~~~~~
    451   GGCCGCACTCGAG
```

Figure 6B

HUMAN SUMO-3 FOR ENHANCING PROTEIN EXPRESSION

This application claims the benefit of U.S. Provisional Application No. 60/640,107, filed Dec. 30, 2004, the contents of which is hereby incorporated by reference in its entirety.

BACKGROUND OF THE INVENTIVE SUBJECT MATTER

1. Field of the Inventive Subject Matter

The inventive subject matter relates to novel compositions, methods, and kits for enhancing the expression, solubility, isolation, and purification of heterologous proteins. Further, inventive subject matter relates to methods for generating proteins with novel N-terminal amino acids, unlike wild-type proteins which always are translated from mRNA with methionine as the N-terminus amino acid.

2. Background

Functional genomic studies have been hampered by the inability to uniformly express and purify biologically active proteins in heterologous expression systems. Despite the use of identical transcriptional and translational signals in a given expression vector, expressed protein levels have been observed to vary dramatically. For this reason, several strategies have been developed to express heterologous proteins in bacteria, yeast, mammalian cells, and insect cells as gene-fusions (see Butt, T. R., S. Jonnalagadda, B. P. Monia, E. J. Sternberg, J. A. Marsh, J. M. Stadel, D. J. Ecker, and S. T. Crooke, 1989, Ubiquitin fusion augments the yield of cloned gene products in *Escherichia coli*, Proc Natl Acad Sci USA 86:2540-4; Ecker, D. J., J. M. Stadel, T. R. Butt, J. A. Marsh, B. P. Monia, D. A. Powers, J. A. Gorman, P. E. Clark, F. Warren, A. Shatzman, and et al., 1989, Increasing gene expression in yeast by fusion to ubiquitin, J Biol Chem 264: 7715-9; Ikonomou, L., Y. J. Schneider, and S. N. Agathos, 2003, Insect cell culture for industrial production of recombinant proteins, Appl Microbiol Biotechnol 62:1-20; and Kapust, R. B., and D. S. Waugh, 1999, *Escherichia coli* maltose-binding protein is uncommonly effective at promoting the solubility of polypeptides to which it is fused, Protein Sci 8:1668-74). Yet such strategies have proved ineffective or insufficient in practice because of poor expression levels, poor solubility, low yields, or a combination thereof.

The expression of heterologous genes in bacteria is by far the simplest and most inexpensive means available for research or commercial purposes. However, some heterologous gene products fail to attain their correct three-dimensional conformation in *E. coli*, while others become sequestered in large insoluble aggregates or "inclusion bodies" when overproduced (see Georgiou, G., and P. Valax, 1999, Isolating inclusion bodies from bacteria, Methods Enzymol 309:48-58; and Jonasson, P., S. Liljeqvist, P. A. Nygren, and S. Stahl, 2002, Genetic design for facilitated production and recovery of recombinant proteins in *Escherichia coli*, Biotechnol Appl Biochem 35:91-105). Major denaturant-induced solubilization methods followed by removal of the denaturant under conditions that favor refolding are often required to produce a reasonable yield of the recombinant protein. Selection of open reading frames (hereinafter "ORFs") for structural genomics projects has also shown that only about 20% of the genes expressed in *E. coli* render proteins that are soluble or correctly folded (see Waldo, G. S., B. M. Standish, J. Berendzen, and T. C. Terwilliger, 1999, Rapid protein-folding assay using green fluorescent protein, Nat Biotechnol 17:691-5). These numbers are startlingly disappointing, especially given that most scientists rely on *E. coli* for initial attempts to express gene products. Several gene fusion systems ostensibly producing fusion proteins incorporating putative expression enhancers such as NusA, maltose binding protein (MBP), glutathione-S-transferase (GST), and thioredoxin (Trx) have been developed (see Jonasson, P., S. Liljeqvist, P. A. Nygren, and S. Stahl, 2002, Genetic design for facilitated production and recovery of recombinant proteins in *Escherichia coli*, Biotechnol Appl Biochem 35:91-105). All of these systems have clear drawbacks, ranging from inefficient expression to inconsistent cleavage from desired structure.

Thus, there is a need for more effective and efficient protein expression systems. This need is met by the inventive subject matter, using novel compositions and methods which have not heretofore been known. The use of the new SUMO fusions and SUMO proteases disclosed in the inventive subject matter herein circumvents the problems of the prior art, and significantly improves upon previously described expression systems based on *Saccharomyces cerevisiae* Smt3 and *Saccharomyces cerevisiae* Ulp1 protease.

SUMMARY OF THE INVENTIVE SUBJECT MATTER

The inventive subject matter relates to a composition for enhancing expression levels of a protein of interest, comprising:

(a) an isolated nucleic acid sequence encoding a SUMO protein;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest, and provided that said SUMO protein is not *Saccharomyces cerevisiae* Smt3.

In addition, the inventive subject matter relates to a composition for enhancing solubility of a protein of interest, comprising:

(a) an isolated nucleic acid sequence encoding a SUMO protein;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest, and provided that said SUMO protein is not *Saccharomyces cerevisiae* Smt3.

Further, the inventive subject matter relates to an expression vector comprising:

(a) an isolated nucleic acid sequence encoding a SUMO protein;

(b) an isolated nucleic acid sequence encoding a protein of interest; and (c) an isolated nucleic acid encoding at least one purification tag, wherein, upon expression in a suitable expression system, said expression vector produces a fusion protein in which said purification tag is N-terminus to said SUMO protein, and said SUMO protein is attached to the amino terminus of said protein of interest, and provided that said SUMO protein is not *Saccharomyces cerevisiae* Smt3.

The inventive subject matter also relates to a method for enhancing expression and isolation of a protein of interest, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding said protein of interest, and (iii) an isolated nucleic acid encoding at least one purification tag, operably linked; and (b) isolating the protein produced by expression of said nucleic acid insert, wherein upon expression in said target cell, said expression vector encodes a fusion protein in which said purification tag is N-terminus to said SUMO protein, and said SUMO protein is attached to the amino terminus of the protein of interest, and provided that said SUMO protein is not *Saccharomyces cerevisiae* Smt3.

Further, the inventive subject matter relates to a method for enhancing the solubility and isolation of a protein of interest, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding said protein of interest, and (iii) an isolated nucleic acid encoding at least one purification tag, operably linked; and (b) isolating the protein produced by expression of said nucleic acid insert;

wherein upon expression in said target cell, said expression vector encodes a fusion protein in which said purification tag is N-terminus to said SUMO protein, and said SUMO protein is attached to the amino terminus of the protein of interest, and provided that said SUMO protein is not *Saccharomyces cerevisiae* Smt3.

More particularly, the inventive subject matter relates to a method for enhancing expression and isolation of a protein of interest, comprising the steps of:]

(a) transforming a target cell with an expression vector comprising (1) a vector which is suitable for transforming a target cell and (2) a nucleic acid insert comprising (i) an isolated nucleic acid sequence encoding human SUMO-3 (SEQ ID NO: 4), (ii) an isolated nucleic acid sequence encoding said protein of interest, and (iii) an isolated nucleic acid encoding at least one purification tag, operably linked;

(b) isolating the protein produced by expression of said nucleic acid insert;

(c) lysing the cell expressing the fusion protein;

(d) purifying the fusion protein by way of said at least one purification tag;

(e) cleaving the SUMO moiety and purification tag(s) from the protein of interest with human SUMO protease SENP2 (SEQ ID NO: 43) or a catalytic domain thereof; and (f) isolating the protein of interest,
wherein upon expression in said target cell, said expression vector encodes a fusion protein in which said purification tag is N-terminus to said SUMO protein, and said SUMO protein is attached to the amino terminus of the protein of interest.

Further, the inventive subject matter particularly relates to a method for enhancing solubility and isolation of a protein of interest, comprising the steps of:

(a) transforming a target cell with an expression vector comprising (1) a vector which is suitable for transforming a target cell and (2) a nucleic acid insert comprising (i) an isolated nucleic acid sequence encoding human SUMO-3 (SEQ ID NO: 4), (ii) an isolated nucleic acid sequence encoding said protein of interest, and (iii) an isolated nucleic acid encoding at least one purification tag, operably linked;

(b) isolating the protein produced by expression of said nucleic acid insert;

(c) lysing the cell expressing the fusion protein;

(d) purifying the fusion protein by way of said at least one purification tag;

(e) cleaving the SUMO moiety and purification tag(s) from the protein of interest with human SUMO protease SENP2 (SEQ ID NO: 43) or a catalytic domain thereof; and (f) isolating the protein of interest,
wherein upon expression in said target cell, said expression vector encodes a fusion protein in which said purification tag is N-terminal to said SUMO protein, and said SUMO protein is attached to the amino terminus of the protein of interest.

In addition, the inventive subject matter relates to a method for generating proteins with a novel N-terminal amino acid which is not proline, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding a protein of interest having a novel N-terminal amino acid, and (iii) an isolated nucleic acid encoding at least one purification tag, operably linked;

(b) isolating the protein produced by expression of said nucleic acid insert,
wherein upon expression in said target cell, said expression vector encodes a fusion protein in which said purification tag is N-terminus to said SUMO protein, and said SUMO protein is attached to the amino terminus of said novel N-terminal amino acid of the protein of interest;

(c) cleaving the SUMO moiety and purification tag(s) from the protein of interest with an appropriate SUMO protease, or a catalytic domain thereof; and (d) isolating the protein of interest having a novel N-terminal amino acid,
provided that said SUMO protease is not *Saccharomyces cerevisiae* Ulp1, and provided that said isolated nucleic acid sequence encoding a SUMO protein is not *Saccharomyces cerevisiae* Smt3.

In another aspect, the inventive subject matter relates to a method for generating proteins with a proline N-terminal amino acid, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding a protein of interest having at least one N-terminal amino acid which is not proline and having a proline adjoining said at least one N-terminal amino acid, and (iii) an isolated nucleic acid encoding at least one purification tag, operably linked;

(b) isolating the protein produced by expression of said nucleic acid insert,
wherein upon expression in said target cell, said expression vector encodes a fusion protein in which said purification tag is N-terminus to said SUMO protein, and said SUMO protein is attached to the amino terminus of said at least one N-terminal amino acid of the protein of interest, and provided that said isolated nucleic acid sequence encoding a SUMO protein is not *Saccharomyces cerevisiae* Smt3;

(c) cleaving the SUMO moiety and purification tag(s) from the protein of interest with an appropriate SUMO protease, or a catalytic domain thereof, provided that said SUMO protease is not *Saccharomyces cerevisiae* Ulp1;

(d) isolating the protein of interest having at least one N-terminal amino acid which is not proline and having a proline adjoining said at least one N-terminal amino acid; and (e) treating said protein of interest with an aminopeptidase to remove said at least one N-terminal amino acid which is not proline and leaving proline as the amino terminus.

Finally, the inventive subject matter relates to a kit for enhancing expression levels of a protein of interest, comprising:

(a) a vector which is suitable for transforming a target cell and which has at least one cloning site for cloning a nucleic acid encoding a protein of interest, operably linked to a nucleic acid insert comprising (i) an isolated nucleic acid sequence encoding a SUMO protein, and (ii) an isolated nucleic acid encoding at least one purification tag, provided that said isolated nucleic acid sequence encoding a SUMO protein is not *Saccharomyces cerevisiae* Smt3, wherein said at least one cloning site is oriented in said vector so that upon cloning in a nucleic acid sequence encoding said protein of interest and expression in a target cell, said vector encodes a fusion protein in which said purification tag is N-terminus to said SUMO protein, and said SUMO protein is attached to the amino terminus of the protein of interest; and (b) a cleavage enzyme for cleaving the SUMO moiety and purification tag(s) from the protein of interest.

BRIEF DESCRIPTION OF THE DRAWINGS

FIG. 1A is an alignment of the polypeptide sequences of the predicted mature forms of known and putative SUMO proteins from various representative organisms. From top to bottom, the sequence are SEQ ID NO: 1, SEQ ID NO: 71, SEQ ID NO: 3, SEQ ID NO: 5, SEQ ID NO: 7, SEQ ID NO: 72, SEQ ID NO: 73, SEQ ID NO: 74, SEQ ID NO: 75, SEQ ID NO: 76, SEQ ID NO: 77, SEQ ID NO: 9, SEQ ID NO: 11, SEQ ID NO: 78, SEQ ID NO: 79, SEQ ID NO: 80, SEQ ID NO: 81, SEQ ID NO: 82, SEQ ID NO: 83, SEQ ID NO: 84, and SEQ ID NO: 85.

FIG. 1B is an alignment of the polypeptide sequences of the catalytic domains of known and putative SUMO proteases from various representative organisms. From top to bottom, the sequences are SEQ ID NOs: 86-108.

FIG. 6B shows the regions that flank the sequences of 6xHis-SUMO in the plasmid, using hSUMO-3 as an example. The nucleotide sequence is SEQ ID NO: 113 and the amino acid sequence is SEQ ID NO: 15.

DETAILED DESCRIPTION OF THE INVENTIVE SUBJECT MATTER

Definitions

Figure 2:
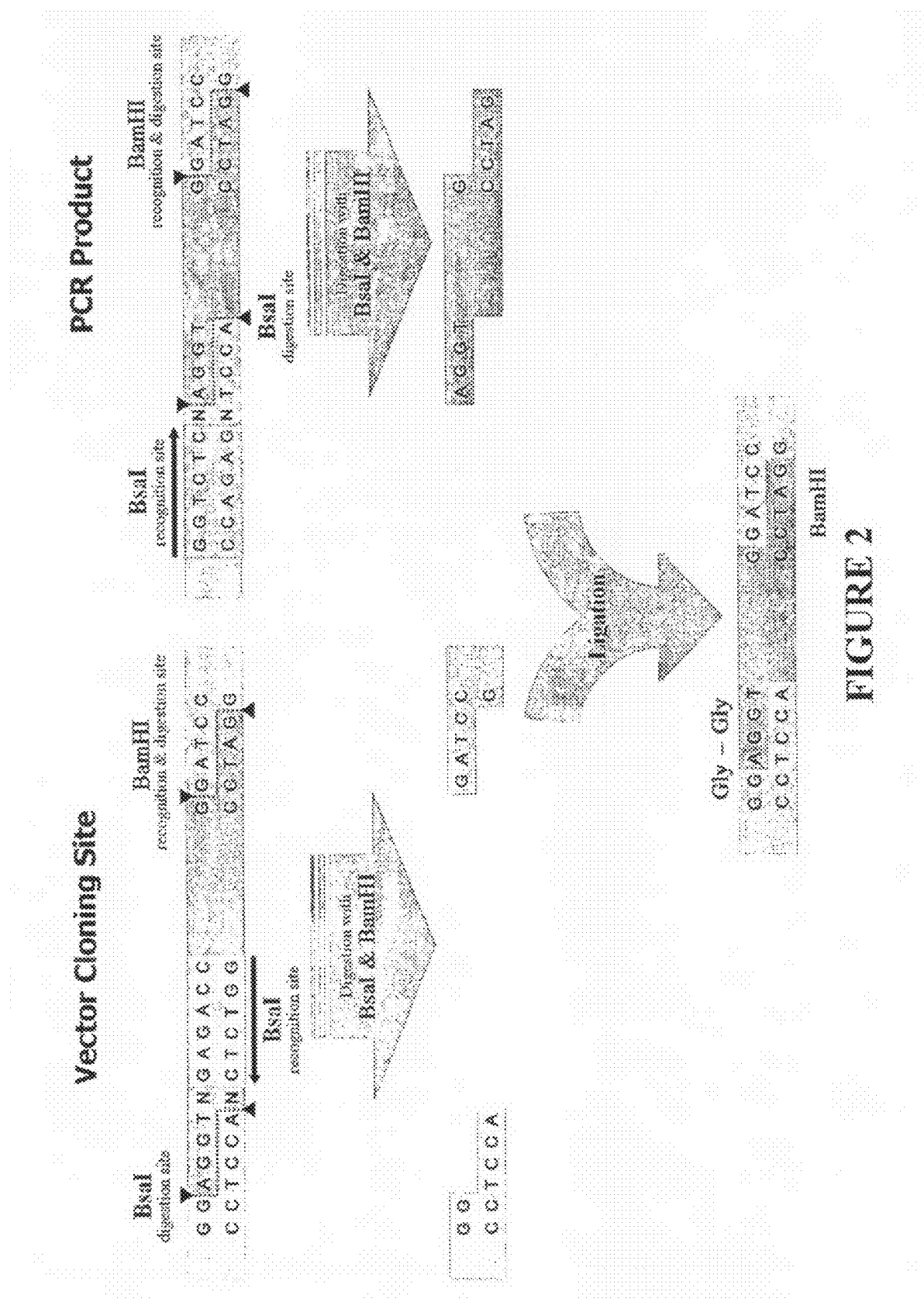
FIG. 2 is a schematic representation of a representative cloning technique used to generate SUMO fusion proteins. The BsaI digestion site under Vector Cloning Site is SEQ ID NO: 109 (top strand) and SEQ ID NO: 110 (bottom strand). The BsaI recognition site under PCR Product is SEQ ID NO: 111 (top strand) and SEQ ID NO: 112 (bottom strand).

For clarity, the term "vector" as used herein refers to a plasmid or other structure which is capable of receiving a heterologous nucleic acid sequence by standard cloning techniques, while the term "expression vector" as used herein refers to a plasmid or other vector into which a heterologous nucleic acid sequence has been cloned.

The term "purification tag" as used herein refers to a moiety attached to a protein of interest which enhances the ability to specifically isolate the protein of interest from other compositions, or from a solution or suspension. An exemplary purification tag is poly (6x) histidine. Purification tags are well known in the art, and are referred to herein without limitation.

The term "catalytic domain" as used herein in relation to proteases, refers to a fragment of a protease which retains the catalytic activity of the wild-type protease.

The term "novel N-terminal amino acid" as used herein refers to an N-terminal amino acid of a polypeptide which is not methionine. As is well known in the art, methionine is the first amino acid in the natural translation of mRNA to a polypeptide, and it is considered novel to produce proteins with an amino acid other than methionine at the N-terminal without resort to use of an aminopeptidase.

The term "mature" as used herein in relation to certain proteins refers to polypeptide sequences remaining after post-translational processing.

The term "equivalent" as used herein in relation to the inventive compositions refers to a composition that performs substantially the same function as another composition in substantially the same way.

The term "homologue" as used herein in relation to the inventive compositions refers to a composition having an amino acid or nucleic acid sequence which corresponds or is similar to another composition in position, structure, and/or function. Homologous proteins should have at least 70% sequence homology, preferably at least 80% sequence homology, and most preferably at least 90% sequence homology. It is now well known to one of ordinary skill in the art that many proteins have identifiable functional domains, such as a substrate binding domain, a recognition sequence, or an active domain having, for example, a protease function. It is also well known, as discussed below, that substantially greater sequence variation is permitted in non-functional domains than functional domains, and thus sequence homology for purposes of this definition may be established over less than all of a protein sequence. Unless otherwise specifically described herein, Applicants hereby incorporate by reference the characteristics which are known in the art relating to particular proteins.

Further, the concept of sequence homology is tied to the distinction between conservative and non-conservative substitutions. In this regard, "identity" refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between sequences of two or more nucleotides or two or more amino acids. "Identity" measures the percentage of identical matches between the smaller of two or more sequences with gap alignments (if any) addressed by a particular mathematical model, computer program, or algorithm.

The term "similarity" is used with regard to a related concept; in contrast to "identity," "similarity" refers to a measure of relatedness that includes both identical matches and conservative substitution matches. If two polypeptide sequences have, for example, 10/20 identical amino acids, and the remainder are all non-conservative substitutions, then the percentage identity and similarity would both be 50%. If in the same example, there are five more positions where there are conservative substitutions, then the percentage identity remains 50%, but the percentage similarity would be 75% (15/20). Therefore, in cases where there are conservative substitutions, the percentage similarity between two polypeptides will be higher than the percentage identity between those two polypeptides. For purposes of this application, Applicants consider conservative substitutions to be a "match" for purposes of determining percent homology.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced, for example, into non-homologous regions of a molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, e.g., Kyte, et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where a biologically functional protein is intended for use in embodiments involving protein-protein interactions, as disclosed herein. In certain embodiments, the greatest local average hydrophilicity of a protein, as governed by the hydrophilicity of its adjacent amino acids, correlates with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. Such regions are referred to as "epitopic core regions, and in some embodiments correlate with a biological property of the protein."

Exemplary amino acid substitutions are set forth in the following Table A.

TABLE A

Amino Acid Substitution

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyricAcid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues, in specific proteins or in similar proteins, that are important for activity or structure. In view of such a comparison, the skilled artisan can readily determine or predict the importance of amino acid residues in a protein that correspond to amino acid residues important for activity or structure in similar proteins. One skilled in the art may then opt for amino acid substitutions for such predicted important amino acid residues in order to maintain function.

One skilled in the art can also analyze the three-dimensional structure of a protein, and the amino acid sequence of the protein in relation to that structure. In view of such information, one skilled in the art may predict the alignment of amino acid residues of an protein with respect to its three-dimensional structure, or may determine three-dimensional structure experimentally. In certain embodiments, one skilled in the art may choose to not make radical changes to amino acid residues on the surface of the protein, since such residues may be involved in interactions with other molecules. Moreover, one skilled in the art may generate test variants, containing a single amino acid substitution at each desired amino acid residue which can be screened using activity assays known to those skilled in the art. Thus, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided, either alone or in combination with other mutations.

The term "operably linked" means that the components to which the term is applied are in a relationship that allows them to carry out their inherent functions under suitable conditions. For example, a control sequence "operably linked" to a protein coding sequence is ligated thereto so that expression of the protein coding sequence is achieved under conditions compatible with the transcriptional activity of the control sequences.

The Inventive Subject Matter

The expression of heterologous genes in bacteria is by far the simplest and most inexpensive means available for research or commercial purposes. However, some heterologous gene products fail to attain their correct three-dimensional conformation in *E. coli*, while others become sequestered in large insoluble aggregates or "inclusion bodies" when overproduced. Major denaturant-induced solubilization methods followed by removal of the denaturant under conditions that favor refolding are then required to produce a reasonable yield of the recombinant protein.

For purposes of evaluating and selecting expression systems, selection of open reading frames for structural genomics projects has shown that only about 20% of the genes expressed in *E. coli* render proteins that are soluble or correctly folded. These numbers are startlingly disappointing, especially given that most scientists rely on *E. coli* for initial attempts to express gene products. Several gene fusion systems, which ostensibly produce fusion proteins, incorporate putative expression enhancers such as NusA, MBP, GST, and Trx. All of these systems have clear drawbacks, ranging from inefficient expression to inconsistent cleavage from desired structure.

Recent work shows that the use of yeast SUMO (Smt3) as an N-terminal tag can increase the expression and solubility of various proteins. Further, yeast SUMO protease Ulp1 has been used to process fusion proteins the fusions in vitro to produce an un-fused protein product of interest. Using these yeast components or variations thereof, expression systems have been developed (see Applicants' work in Malakhov, et al., 2004, *SUMO fusions and SUMO-specific protease for efficient expression and purification of proteins*, J Struct Funct Genomics 5:75-86), but SUMO proteins and proteases other than *Saccharomyces cerevisiae* Smt3 and Ulp1 have not previously been employed in expression systems.

Fusion proteins made with other enhancers, such as NusA, promote solubility of partner proteins, presumably due to their large size. In addition, protein fusions with glutathione-S-transferase (GST) or maltose binding protein (MBP) have been proposed to enhance expression and yield of fusion partners. However, enhanced expression is not always observed when GST is used, as GST forms dimers and can retard protein solubility. Another problem with GST, and other fusion systems, is that the desired protein may have to be removed from the fusion (See, e.g., Marblestone, et al., (2006) Comparison of SUMO Fusion Technology with Traditional Gene Fusion System: Effects of Recombinant Protein Expression and Purification. Protein Science 15(1):182-9; Butt, et al., (2005) SUMO Fusion Technology for Difficult to Express Proteins. Protein Expr. Purif. 43:1-9; Zuo, et al., (2005) Expression and Purification of SARS Coronavirus Proteins Using SUMO-Fusions. Protein Expr. Purif. 42:100-110; and Zuo, et al., (2005) Enhanced expression and purification of membrane proteins by SUMO fusion in *Echerichia coli*. J Struct. Funct. Genomics 6(2-3):103-11.). To circumvent this problem, protease sites, such as Factor Xa, thrombin, enterokinase or Tev protease sites have been engineered downstream of the fusion partner. Often in these cases, however, incomplete cleavage, and inappropriate cleavage within the fusion protein, or both, are observed (see Jonasson, et al. supra).

Inventive Compositions

The inventive subject matter relates to a composition for enhancing expression levels of a protein of interest, comprising:

(a) an isolated nucleic acid sequence encoding a SUMO protein;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest, and provided that said SUMO protein is not *Saccharomyces cerevisiae* Smt3.

In one aspect of the inventive subject matter, said nucleic acid sequence encoding a SUMO protein is derived from an organism selected from the group consisting of human, mouse, insect, plant, yeast, and other eukaryotic organisms.

In another aspect of the inventive subject matter, said organism comprises *Homo sapiens, Arabidopsis thalania*, tomato, *Xenopus laevis, Drosophila melanogaster, Caenorhabditis elegans, Schizosaccharomyces pombe, Plasmodium falciparum*, or *Aspergillus nidulans*.

In a preferred embodiment, said nucleic acid sequence encoding a SUMO protein comprises human SUMO-1, human SUMO-2, human SUMO-3, any one of *Arabidopsis*

*thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, an equivalent thereof, a homologue thereof, or a combination thereof.

In another preferred embodiment, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof.

In a more preferred embodiment, said nucleic acid sequence encoding a SUMO protein comprises human SUMO-3 (SEQ ID NO: 4).

In a further aspect of the inventive subject matter, said nucleic acid composition for enhancing expression levels of a protein of interest, comprises:

(a) an isolated enhancer nucleic acid sequence comprising human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest.

In a preferred embodiment, said enhancer nucleic acid sequence comprises human SUMO-3 (SEQ ID NO: 4).

In addition, the inventive subject matter relates to a composition for enhancing solubility of a protein of interest, comprising:

(a) an isolated nucleic acid sequence encoding a SUMO protein;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest, and provided that said SUMO protein is not *Saccharomyces cerevisiae* Smt3.

In one aspect of the inventive subject matter, said nucleic acid sequence encoding a SUMO protein is derived from an organism selected from the group consisting of human, mouse, insect, plant, yeast, and other eukaryotic organisms.

In another aspect of the inventive subject matter, said organism comprises *Homo sapiens, Arabidopsis thalania, tomato, Xenopus laevis, Drosophila melanogaster, Caenorhabditis elegans, Schizosaccharomyces pombe, Plasmodium falciparum*, or *Aspergillus nidulans*.

In a further aspect of the inventive subject matter, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, an equivalent thereof, a homologue thereof, or a combination thereof.

In an alternate aspect of the inventive subject matter, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof.

In a preferred embodiment, said nucleic acid sequence encoding a SUMO protein comprises human SUMO-3 (SEQ ID NO: 4).

In yet another aspect of the inventive subject matter, said nucleic acid composition for enhancing solubility of a protein of interest, comprising:

(a) an isolated enhancer nucleic acid sequence comprising human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest.

In a preferred embodiment, said enhancer nucleic acid sequence comprises human SUMO-3 (SEQ ID NO: 4).

Further, the inventive subject matter relates to an expression vector comprises:

(a) an isolated nucleic acid sequence encoding a SUMO protein;

(b) an isolated nucleic acid sequence encoding a protein of interest; and (c) an isolated nucleic acid encoding at least one purification tag, wherein, upon expression in a suitable expression system, said expression vector produces a fusion protein in which said purification tag is N-terminus to said SUMO protein, and said SUMO protein is attached to the amino terminus of said protein of interest, and provided that said SUMO protein is not *Saccharomyces cerevisiae* Smt3.

In one aspect of the inventive subject matter, said nucleic acid sequence encoding a SUMO protein is derived from an organism selected from the group consisting of human, mouse, insect, plant, yeast, and other eukaryotic organisms.

In another aspect of the inventive subject matter, said organism comprises *Homo sapiens, Arabidopsis thalania, tomato, Xenopus laevis, Drosophila melanogaster, Cae-* norhabditis elegans, Schizosaccharomyces pombe, Plasmodium falciparum, or Aspergillus nidulans.

In a further aspect of the inventive subject matter, said nucleic acid sequence encoding a SUMO protein is selected from the group consisting of human SUMO-1, human SUMO-2, human SUMO-3, any one of Arabidopsis thalania SUMO-1 through SUMO-8, tomato SUMO, any one of Xenopus laevis SUMO-1 through SUMO-3, Drosophila melanogaster Smt3, Caenorhabditis elegans SMO-1, Schizosaccharomyces pombe Pmt3, malarial parasite Plasmodium falciparum SUMO, mold Aspergillus nidulans SUMO, an equivalent thereof, a homologue thereof, or a combination thereof.

In an alternate aspect of the inventive subject matter, said organism comprises Homo sapiens, Arabidopsis thalania, tomato, Xenopus laevis, Drosophila melanogaster, Caenorhabditis elegans, Schizosaccharomyces pombe, Plasmodium falciparum, or Aspergillus nidulans.

In a preferred embodiment, said nucleic acid sequence encoding a SUMO protein is human SUMO-3 (SEQ ID NO: 4).

In yet another aspect of the inventive subject matter, said expression vector comprises:

(a) an isolated enhancer nucleic acid sequence comprising human SUMO-1, human SUMO-2, human SUMO-3, any one of Arabidopsis thalania SUMO-1 through SUMO-8, tomato SUMO, any one of Xenopus laevis SUMO-1 through SUMO-3, Drosophila melanogaster Smt3, Caenorhabditis elegans SMO-1, Schizosaccharomyces pombe Pmt3, malarial parasite Plasmodium falciparum SUMO, mold Aspergillus nidulans SUMO, or a combination thereof;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest.

In a preferred embodiment, said enhancer nucleic acid sequence comprises human SUMO-3 (SEQ ID NO: 4).

Inventive Methods

The inventive subject matter also relates to a method for enhancing expression and isolation of a protein of interest, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding said protein of interest, and (iii) an isolated nucleic acid encoding at least one purification tag, operably linked; and (b) isolating the protein produced by expression of said nucleic acid insert, wherein upon expression in said target cell, said expression vector encodes a fusion protein in which said purification tag is N-terminus to said SUMO protein, and said SUMO protein is attached to the amino terminus of the protein of interest, and provided that said SUMO protein is not Saccharomyces cerevisiae Smt3.

In one aspect of the inventive subject matter, said nucleic acid sequence encoding a SUMO protein is derived from an organism selected from the group consisting of human, mouse, insect, plant, yeast, and other eukaryotic organisms.

In another aspect of the inventive subject matter, said organism comprises Homo sapiens, Arabidopsis thalania, tomato, Xenopus laevis, Drosophila melanogaster, Caenorhabditis elegans, Schizosaccharomyces pombe, Plasmodium falciparum, or Aspergillus nidulans.

In a further aspect of the inventive subject matter, said nucleic acid sequence encoding a SUMO protein is selected from the group consisting human SUMO-2, human SUMO-3, any one of Arabidopsis thalania SUMO-1 through SUMO-8, tomato SUMO, any one of Xenopus laevis SUMO-1 through sumo-3, Drosophila melanogaster SUMO, Caenorhabditis elegans SUMO, Schizosaccharomyces pombe Pmt3, malarial parasite Plasmodium falciparum SUMO, mold Aspergillus nidulans SUMO, an equivalent thereof, a homologue thereof, or a combination thereof.

In an alternate aspect of the inventive subject matter, said nucleic acid sequence encoding a SUMO protein comprises human SUMO-1, human SUMO-2, human SUMO-3, any one of Arabidopsis thalania SUMO-1 through SUMO-8, tomato SUMO, any one of Xenopus laevis SUMO-1 through SUMO-3, Drosophila melanogaster Smt3, Caenorhabditis elegans SMO-1, Schizosaccharomyces pombe Pmt3, malarial parasite Plasmodium falciparum SUMO, mold Aspergillus nidulans SUMO, or a combination thereof.

In a preferred embodiment, said nucleic acid sequence encoding a SUMO protein is human SUMO-3 (SEQ ID NO: 4).

In yet another aspect of the inventive subject matter, said method for enhancing expression and isolation of a protein of interest, comprising the steps of:

(a) transforming a target cell with an expression vector comprising an isolated enhancer nucleic acid sequence comprising human SUMO-1, human SUMO-2, human SUMO-3, any one of Arabidopsis thalania SUMO-1 through SUMO-8, tomato SUMO, any one of Xenopus laevis SUMO-1 through SUMO-3, Drosophila melanogaster Smt3, Caenorhabditis elegans SMO-1, Schizosaccharomyces pombe Pmt3, malarial parasite Plasmodium falciparum SUMO, mold Aspergillus nidulans SUMO, or a combination thereof;

(b) an isolated nucleic acid sequence encoding said protein of interest; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest.

In a preferred embodiment, said enhancer nucleic acid sequence comprises human SUMO-3 (SEQ ID NO: 4).

In another aspect of the inventive subject matter, said method optionally comprises one or more additional step(s) of:

(d) lysing the target cell expressing the fusion protein;

(e) purifying the fusion protein by way of said at least one purification tag;

(f) cleaving the SUMO moiety and purification tag(s) from the protein of interest with an appropriate SUMO protease or a catalytic domain thereof, provided that said SUMO protease is not Saccharomyces cerevisiae Ulp1; and (g) isolating the protein of interest.

In a further aspect of the inventive subject matter, said SUMO protease is derived from an organism selected from the group consisting of human, mouse, insect, plant, yeast, other eukaryotes, and prokaryotic plant and animal pathogens.

In an alternate aspect of the inventive subject matter, said organism comprises *Homo sapiens, Mus musculus, Saccharomyces cerevisiae, Arabidopsis thalania, Caenorhabditis elegans, Drosophila melanogaster, Schizosaccharomyces pombe, Aspergillus nidulans, Xenopus laevis, Xanthomonas campestris, Kluyveromyces lactis,* or *Plasmodium falciparum.*

In yet another aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b, *Xanthomonas campestris* XopD, *Kluyveromyces lactis* Ulp1, *Plasmodium falciparum* Ulp, an equivalent thereof, a homologue thereof, a catalytic domain thereof, or a combination thereof.

In a preferred embodiment, said SUMO protease comprises human SUMO protease SENP2 (SEQ ID NO: 43) or a catalytic domain thereof.

In another aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b, *Xanthomonas campestris* XopD, *Kluyveromyces lactis* Ulp1, *Plasmodium falciparum* Ulp, a catalytic domain thereof, or a combination thereof.

In a preferred embodiment, said SUMO protease comprises human SUMO protease SENP2 (SEQ ID NO: 43) or a catalytic domain thereof.

Further, the inventive subject matter relates to a method for enhancing the solubility and isolation of a protein of interest, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding said protein of interest, and (iii) an isolated nucleic acid encoding at least one purification tag, operably linked; and (b) isolating the protein produced by expression of said nucleic acid insert;

wherein upon expression in said target cell, said expression vector encodes a fusion protein in which said purification tag is N-terminus to said SUMO protein, and said SUMO protein is attached to the amino terminus of the protein of interest, and provided that said SUMO protein is not *Saccharomyces cerevisiae* Smt3.

In one aspect of the inventive subject matter, said nucleic acid sequence encoding a SUMO protein is derived from an organism selected from the group consisting of human, mouse, insect, plant, yeast, and other eukaryotic organisms.

In another aspect of the inventive subject matter, said organism comprises *Homo sapiens, Arabidopsis thalania,* tomato, *Xenopus laevis, Drosophila melanogaster, Caenorhabditis elegans, Schizosaccharomyces pombe, Plasmodium falciparum,* or *Aspergillus nidulans.*

In a further aspect of the inventive subject matter, said nucleic acid sequence encoding a SUMO protein is selected from the group consisting selected from the group consisting of human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, an equivalent thereof, a homologue thereof, or a combination thereof.

In a preferred embodiment, said nucleic acid sequence encoding a SUMO protein comprises human SUMO-3 (SEQ ID NO: 4).

In an alternate aspect of the inventive subject matter, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof.

In a preferred embodiment, said nucleic acid sequence encoding a SUMO protein comprises human SUMO-3 (SEQ ID NO: 4).

In yet another aspect of the inventive subject matter, said method optionally comprises one or more additional step(s) of:

(d) lysing the target cell expressing the fusion protein;

(e) purifying the fusion protein by way of said at least one purification tag;

(f) cleaving the SUMO moiety and purification tag(s) from the protein of interest with an appropriate SUMO protease, or a catalytic domain thereof; and (g) isolating the protein of interest, provided that said SUMO protease is not *Saccharomyces cerevisiae* Ulp1.

In another aspect of the inventive subject matter, said SUMO protease is derived from an organism selected from the group consisting of human, mouse, insect, plant, yeast, other eukaryotes, and prokaryotic plant and animal pathogens.

In a further aspect of the inventive subject matter, said organism comprises *Homo sapiens, Mus musculus, Saccharomyces cerevisiae, Arabidopsis thalania, Caenorhabditis elegans, Drosophila melanogaster, Schizosaccharomyces pombe, Aspergillus nidulans, Xenopus laevis, Xanthomonas campestris, Kluyveromyces lactis,* or *Plasmodium falciparum.*

In an alternate aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b,

*Xanthomonas campestris* XopD, *Kluyveromyces lactis* Ulp1, and *Plasmodium falciparum* Ulp, an equivalent thereof, a homologue thereof, a catalytic domain thereof, or a combination thereof.

In a preferred embodiment, said SUMO protease comprises human SUMO protease SENP2 (SEQ ID NO: 43) or a catalytic domain thereof.

In yet another aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b, *Xanthomonas campestris* XopD, *Kluyveromyces lactis* Ulp1, *Plasmodium falciparum* Ulp, a catalytic domain thereof, or a combination thereof.

In a preferred embodiment, said SUMO protease comprises human SUMO protease SENP2 (SEQ ID NO: 43) or a catalytic domain thereof.

More particularly, the inventive subject matter relates to a method for enhancing expression and isolation of a protein of interest, comprising the steps of:

(a) transforming a target cell with an expression vector comprising (1) a vector which is suitable for transforming a target cell and (2) a nucleic acid insert comprising (i) an isolated nucleic acid sequence encoding human SUMO-3 (SEQ ID NO: 4), (ii) an isolated nucleic acid sequence encoding said protein of interest, and (iii) an isolated nucleic acid encoding at least one purification tag, operably linked;

(b) isolating the protein produced by expression of said nucleic acid insert;

(c) lysing the cell expressing the fusion protein;

(d) purifying the fusion protein by way of said at least one purification tag;

(e) cleaving the SUMO moiety and purification tag(s) from the protein of interest with human SUMO protease SENP2 (SEQ ID NO: 43) or a catalytic domain thereof; and (f) isolating the protein of interest, wherein upon expression in said target cell, said expression vector encodes a fusion protein in which said purification tag is N-terminus to said SUMO protein, and said SUMO protein is attached to the amino terminus of the protein of interest.

Further, the inventive subject matter particularly relates to a method for enhancing solubility and isolation of a protein of interest, comprising the steps of:

(a) transforming a target cell with an expression vector comprising (1) a vector which is suitable for transforming a target cell and (2) a nucleic acid insert comprising (i) an isolated nucleic acid sequence encoding human SUMO-3 (SEQ ID NO: 4), (ii) an isolated nucleic acid sequence encoding said protein of interest, and (iii) an isolated nucleic acid encoding at least one purification tag, operably linked;

(b) isolating the protein produced by expression of said nucleic acid insert;

(c) lysing the cell expressing the fusion protein;

(d) purifying the fusion protein by way of said at least one purification tag;

(e) cleaving the SUMO moiety and purification tag(s) from the protein of interest with human SUMO protease SENP2 (SEQ ID NO: 43) or a catalytic domain thereof; and (f) isolating the protein of interest, wherein upon expression in said target cell, said expression vector encodes a fusion protein in which said purification tag is N-terminal to said SUMO protein, and said SUMO protein is attached to the amino terminus of the protein of interest.

In addition, the inventive subject matter relates to a method for generating proteins with a novel N-terminal amino acid which is not proline, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding a protein of interest having a novel N-terminal amino acid, and (iii) an isolated nucleic acid encoding at least one purification tag, operably linked;

(b) isolating the protein produced by expression of said nucleic acid insert, wherein upon expression in said target cell, said expression vector encodes a fusion protein in which said purification tag is N-terminus to said SUMO protein, and said SUMO protein is attached to the amino terminus of said novel N-terminal amino acid of the protein of interest;

(c) cleaving the SUMO moiety and purification tag(s) from the protein of interest with an appropriate SUMO protease, or a catalytic domain thereof; and (d) isolating the protein of interest having a novel N-terminal amino acid, provided that said SUMO protease is not *Saccharomyces cerevisiae* Ulp1, and provided that said isolated nucleic acid sequence encoding a SUMO protein is not *Saccharomyces cerevisiae* Smt3.

In one aspect of the inventive subject matter, said nucleic acid sequence encoding a SUMO protein is derived from an organism selected from the group consisting of human, mouse, insect, plant, yeast, and other eukaryotic organisms.

In another aspect of the inventive subject matter, said organism comprises *Homo sapiens, Arabidopsis thalania,* tomato, *Xenopus laevis, Drosophila melanogaster, Caenorhabditis elegans, Schizosaccharomyces pombe, Plasmodium falciparum,* or *Aspergillus nidulans.*

In a further aspect of the inventive subject matter, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, an equivalent thereof, a homologue thereof, or a combination thereof.

In a preferred embodiment, said nucleic acid sequence encoding a SUMO protein comprises human SUMO-3 (SEQ ID NO: 4).

In an alternate aspect of the inventive subject matter, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof.

In a preferred embodiment, said nucleic acid sequence encoding a SUMO protein comprises human SUMO-3 (SEQ ID NO: 4).

In yet another aspect of the inventive subject matter, said expression vector comprises (a) human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof;

(b) an isolated nucleic acid sequence encoding said protein of interest having a novel N-terminal amino acid; and (c) an isolated nucleic acid encoding at least one purification tag, wherein, upon expression in a suitable expression system, said nucleic acid composition produces a fusion protein in which said purification tag is N-terminus to said SUMO protein, and said SUMO protein is attached to the amino terminus of said protein of interest having a novel N-terminal amino acid.

In a preferred embodiment, said enhancer nucleic acid sequence comprises human SUMO-3 (SEQ ID NO: 4).

In another aspect of the inventive subject matter, said cleavage enzyme comprises a SUMO protease, or a catalytic domain thereof.

In a further aspect of the inventive subject matter, said SUMO protease is derived from an organism selected from the group consisting of human, mouse, insect, plant, yeast, other eukaryotes, and prokaryotic plant and animal pathogens.

In an alternate aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b, *Xanthomonas campestris* XopD, *Kluyveromyces lactis* Ulp1, or *Plasmodium falciparum* Ulp, an equivalent thereof, a homologue thereof, a catalytic domain thereof, or a combination thereof.

In a preferred embodiment, said SUMO protease comprises human SUMO protease SENP2 (SEQ ID NO: 43) or a catalytic domain thereof.

In yet another aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b, *Xanthomonas campestris* XopD, *Kluyveromyces lactis* Ulp1, *Plasmodium falciparum* Ulp, a catalytic domain thereof, or a combination thereof.

In a preferred embodiment, said SUMO protease comprises human SUMO protease SENP2 (SEQ ID NO: 43) or a catalytic domain thereof.

In another aspect, the inventive subject matter relates to a method for generating proteins with a proline N-terminal amino acid, comprising the steps of:

(a) transforming a target cell with an expression vector comprising (1) a vector which is suitable for transforming a target cell and (2) a nucleic acid insert comprising (i) an isolated nucleic acid sequence encoding a SUMO protein, (ii) an isolated nucleic acid sequence encoding a protein of interest having at least one N-terminal amino acid which is not proline and having a proline adjoining said at least one N-terminal amino acid, and (iii) an isolated nucleic acid encoding at least one purification tag, operably linked;

(b) isolating the protein produced by expression of said nucleic acid insert, wherein upon expression in said target cell, said expression vector encodes a fusion protein in which said purification tag is N-terminus to said SUMO protein, and said SUMO protein is attached to the amino terminus of said at least one N-terminal amino acid of the protein of interest, and provided that said isolated nucleic acid sequence encoding a SUMO protein is not *Saccharomyces cerevisiae* Smt3;

(c) cleaving the SUMO moiety and purification tag(s) from the protein of interest with an appropriate SUMO protease, or a catalytic domain thereof, provided that said SUMO protease is not *Saccharomyces cerevisiae* Ulp1;

(d) isolating the protein of interest having at least one N-terminal amino acid which is not proline and having a proline adjoining said at least one N-terminal amino acid; and (e) treating said protein of interest with an aminopeptidase to remove said at least one N-terminal amino acid which is not proline and leaving proline as the amino terminus.

In one aspect of the inventive subject matter, said at least one N-terminal amino acid which is not proline comprises methionine and said aminopeptidase comprises methionine aminopeptidase or (b) said at least one N-terminal amino acid which is not proline comprises alanine and said aminopeptidase comprises alanine aminopeptidase.

Inventive Kits

Finally, the inventive subject matter relates to a kit for enhancing expression levels of a protein of interest, comprising:

(a) a vector which is suitable for transforming a target cell and which has at least one cloning site for cloning a nucleic acid encoding a protein of interest, operably linked to a nucleic acid insert comprising (i) an isolated nucleic acid sequence encoding a SUMO protein, and (ii) an isolated nucleic acid encoding at least one purification tag, provided that said isolated nucleic acid sequence encoding a SUMO protein is not *Saccharomyces cerevisiae* Smt3, wherein said at least one cloning site is oriented in said vector so that upon cloning in a nucleic acid sequence encoding said protein of interest and expression in a target cell, said vector encodes a fusion protein in which said purification tag is N-terminus to said SUMO protein, and said SUMO protein is attached to the amino terminus of the protein of interest; and (b) a cleavage enzyme for cleaving the SUMO moiety and purification tag(s) from the protein of interest.

In one aspect of the inventive subject matter, said nucleic acid sequence encoding a SUMO protein is derived from an organism selected from the group consisting of human, mouse, insect, plant, yeast, and other eukaryotic organisms.

In another aspect of the inventive subject matter, said organism comprises *Homo sapiens, Arabidopsis thalania,* tomato, *Xenopus laevis, Drosophila melanogaster, Caenorhabditis elegans, Schizosaccharomyces pombe, Plasmodium falciparum,* or *Aspergillus nidulans.*

In a further aspect of the inventive subject matter, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, an equivalent thereof, a homologue thereof, or a combination thereof.

In an alternate aspect of the inventive subject matter, said nucleic acid sequence encoding a SUMO protein comprises human SUMO-1, human SUMO-2, human SUMO-3, any one of *Arabidopsis thalania* SUMO-1 through SUMO-8, tomato SUMO, any one of *Xenopus laevis* SUMO-1 through SUMO-3, *Drosophila melanogaster* Smt3, *Caenorhabditis elegans* SMO-1, *Schizosaccharomyces pombe* Pmt3, malarial parasite *Plasmodium falciparum* SUMO, mold *Aspergillus nidulans* SUMO, or a combination thereof.

In a preferred embodiment, said nucleic acid sequence encoding a SUMO protein comprises human SUMO-3 (SEQ ID NO: 4).

In yet another aspect of the inventive subject matter, said cleavage enzyme is a SUMO protease, or a catalytic domain thereof.

In another aspect of the inventive subject matter, said SUMO protease is derived from an organism selected from the group consisting of human, mouse, insect, plant, yeast, other eukaryotes, and prokaryotic plant and animal pathogens.

In a further aspect of the inventive subject matter, said organism comprises *Homo sapiens, Mus musculus, Saccharomyces cerevisiae, Arabidopsis thalania, Caenorhabditis elegans, Drosophila melanogaster, Schizosaccharomyces pombe, Aspergillus nidulans, Xenopus laevis, Xanthomonas campestris, Kluyveromyces lactis,* or *Plasmodium falciparum.*

In an alternate aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b, *Xanthomonas campestris* XopD, *Kluyveromyces lactis* Ulp1, and *Plasmodium falciparum* Ulp, an equivalent thereof, a homologue thereof, a catalytic domain thereof, or a combination thereof.

In a preferred embodiment, said SUMO protease comprises human SUMO protease SENP2 (SEQ ID NO: 43) or a catalytic domain thereof.

In yet another aspect of the inventive subject matter, said SUMO protease comprises *Saccharomyces cerevisiae* Ulp2, human SENP1, human SENP2, human SENP3, human SENP5, human SENP6, human SENP7, mouse SENP1, mouse SENP2, mouse SENP3, mouse SENP5, mouse SENP6, mouse SENP7, any one of *Arabidopsis thalania* Ulp1a through Ulp1d, any one of *Arabidopsis thalania* Ulp2a through Ulp2h, *Arabidopsis thalania* ESD4, *Caenorhabditis elegans* Ulp-1, *Caenorhabditis elegans* Ulp-2, *Drosophila melanogaster* ULP1, *Schizosaccharomyces pombe* Ulp1, *Schizosaccharomyces pombe* ULP2, *Aspergillus nidulans* Ulp, *Xenopus laevis* XSENP1a, *Xenopus laevis* XSENP1b, *Xanthomonas campestris* XopD, *Kluyveromyces lactis* Ulp1, *Plasmodium falciparum* Ulp, a catalytic domain thereof, or a combination thereof.

In a preferred embodiment, said SUMO protease comprises human SUMO protease SENP2 (SEQ ID NO: 43) or a catalytic domain thereof.

Thus, some embodiments of the inventive subject matter may be understood to encompass compositions and methods for enhancing expression levels and solubility of a protein of interest, and for isolating said protein. Optionally, the protein of interest may be produced with a desired N-terminus, other than methionine as produced in nature.

In accordance with an embodiment of the inventive subject matter, a method for improving the expression of a protein, particularly an unexpressed or poorly expressed protein, is provided. In particular, the inventive subject matter relates to a method which comprises attaching a SUMO protein from human, mouse, insect, plant, yeast, or other eukaryote to the amino-terminus of the protein to be expressed, also referred to herein as the protein of interest. Applicants have found that SUMO proteins share a similar, common 3-D structure with one another and with ubiquitin. A hallmark of SUMO and most other ubiquitin-related proteins is that they are synthesized as precursors and processed by a hydrolase or protease at the carboxy-terminus, at a di-glycine motif, to generate a mature sequence. Another feature of the inventive subject matter is the use of such a protease from human, mouse, insect, plant, yeast, or other eukaryote or prokaryotic plant or animal pathogen to process expressed SUMO fusion proteins to generate proteins of interest with desired N-termini.

Methods employing fusion proteins with full-length or partial SUMO and other Ubls to obtain expression and purification have been previously described by Applicants in U.S. application Ser. Nos. 10/338,411 and 10/389,640. These previous SUMO-fusion expression systems have been based on the SUMO protein Smt3 from the yeast *Saccharomyces cerevisiae* and have employed the *S. cerevisiae* SUMO protease Ulp1 for cleavage of the fusion. Cleavage of SUMO fusions was possible except when proline was the amino-terminal residue of the protein of interest.

An exemplary method comprises i) generating a construct encoding a fusion protein by operably linking a nucleic acid sequence encoding a SUMO protein from human, mouse, insect, plant, yeast, or other eukaryotic organism, except not *Saccharomyces cerevisiae* Smt3, to a nucleic acid sequence encoding the protein of interest and to a nucleic acid sequence encoding at least one purification tag, whereby the purification tag is added to the amino terminus of the SUMO protein, which in turn is attached to the amino-terminus of the protein of interest, and ii) introducing the nucleic acid encoding the fusion protein into a host cell. To purify the protein of interest and generate a non-methionine N-terminus, the method may further comprise: iii) lysing host cells expressing the fusion protein, iv) purifying the fusion protein by way of the affinity tag, and v) cleaving off the SUMO moiety with an appropriate recombinant SUMO protease, which may be derived from human, mouse, insect, plant, yeast, or other eukaryote, or prokaryotic plant or animal pathogen to release the protein of interest from the fusion protein.

A more specific example of the inventive subject matter is the use of the human SUMO-3 protein (SEQ ID NO: 4) as an N-terminal fusion to increase the expression of a protein of interest in *E. coli*, followed by purification and in vitro cleavage by the catalytic domain of the human SUMO protease SENP2 (SEQ ID NO: 43). Applicants have found that, surprisingly, human SUMO-3 is a more effective expression tag than yeast SUMO (Smt3), and the human SUMO protease SENP2 cleaves an hSUMO-3 fusion protein in vitro much more effectively than does the yeast SUMO protease Ulp1.

There are a number of reasons for the lack of efficient recombinant protein expression in a host, including, for example, short half-life, improper folding, compartmentalization and codon bias. While the Human Genome project has successfully created a DNA "map" of the human genome, the development of protein expression technologies that function uniformly in different expression platforms and for all the protein motifs has not yet been achieved.

Provided herein are methods which allow for the expression of fusion proteins with SUMO protein species other than ySmt3, such as human SUMO-3, to improve expression. Purification can be based on an optionally SUMO-attached affinity tag (i.e. purification tag) such as 6xHis, and cleavage is then obtained in vitro with a specific SUMO hydrolase other than *S. cerevisiae* Ulp1, such as human SENP2, that recognizes the particular SUMO protein used. The SUMO protein and protease pair may potentially be derived from any organism(s), and may be from the same species or different species.

The inventive subject matter may also be utilized to generate proteins with novel N-termini in eukaryotic cells.

The identity of the N-terminus of a protein has been proposed to control its half-life, also called the N-end Rule (Varshavsky, A., 1996, The N-end rule: functions, mysteries, uses, Proc Natl Acad Sci USA 93:12142-9). Many important biopharmaceuticals, such as growth factors, chemokines, and other cellular proteins, require desired N-termini for therapeutic activity. It has not been previously possible to generate desired N-termini in vivo, as nature initiates translation from methionine. In previously existing N-terminal modification systems, one or more amino acids may be removed from the N-terminus, other amino acids may be added, and various covalent modifications may be introduced to the exposed N-termini (Link, A. J., K. Robison, and G. M. Church, 1997, Comparing the predicted and observed properties of proteins encoded in the genome of *Escherichia coli* K-12, Electrophoresis 18:1259-313). These modification systems are complex and vary to some degree in specificity and performance (Varshavsky, A., 2003, The N-end rule and regulation of apoptosis, Nat Cell Biol 5:373-6). This means that recombinantly produced proteins that do not undergo in vitro processing by a protease of known specificity may have unexpected and/or heterogeneous N-termini.

According to the inventive subject matter, any amino acid can be incorporated as the N-terminal residue of a protein of interest by altering the appropriate codon in the nucleic acid encoding for the protein of interest. The altered protein of interest is then attached to a SUMO protein, expressed in a desired cell, and purified as described herein and then cleaved with a specific protease.

Alternatively, the fusion protein may be expressed in vivo to produce the protein of interest so long as there is specific protease activity in the cell (i.e. native or provided exogenously). Every amino acid except for proline may be employed as the amino-terminal residue by these methods. To employ proline as the amino-terminal residue of the protein of interest, a fusion protein in which the cleavage site of the Ubl protease is followed by the amino acid sequence Met-Pro. Following reconstitution and cleavage with the appropriate protease, the Met-Pro amino-terminus of the protein of interest is further treated with an aminopeptidase such as alanine aminopeptidase or methionine aminopeptidase (see Ben-Bassat, A., 1991, Methods for removing N-terminal methionine from recombinant proteins, Bioprocess Technol 12:147-59) to remove the N-terminal amino acid and leave proline as the amino-terminus.

Figure 1A:
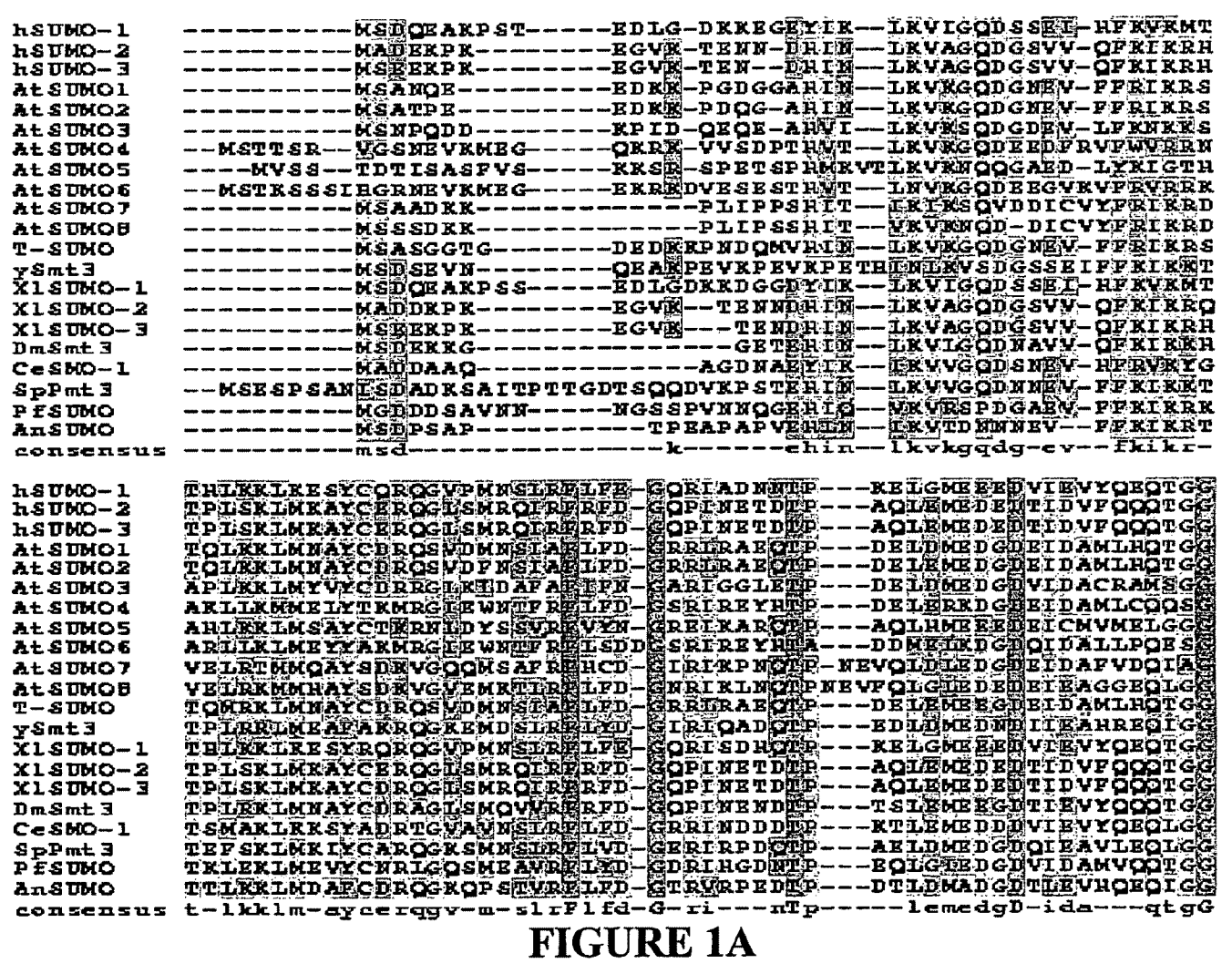

Any of the known or putative SUMO proteins (see FIG. 1A for representative sets of sequences of their mature forms) may be utilized in the compositions and methods of the inventive subject matter to (1) enhance expression of heterologous fusion proteins of interest, (2) enhance solubility of heterologous fusion proteins of interest, (3) allow affinity purification of the fusion protein by way of an additional N-terminal tag such as 6xHis, and (4) allow recognition for cleavage. These SUMO proteins include but are not limited to those presented in the alignment in FIG. 1A. FIG. 1A is an alignment of the published polypeptide sequences of the predicted mature forms of known and putative SUMO proteins from various organisms. Only a representative set of previously described SUMO sequences are provided; it is expected that all eukaryotes have one or more forms of SUMO. There is only one SUMO protein in the yeast *Saccharomyces cerevisiae* (ySmt3), but there are 3 in mammals such as human (hSUMO-1, -2, and -3) and mouse, and there are as many as 8 in the plant *Arabidopsis thalania* (see Kurepa, et al., 2003, The small ubiquitin-like modifier (SUMO) protein modification system in *Arabidopsis*, Accumulation of SUMO1 and -2 conjugates is increased by stress, J Biol Chem 278:6862-72; and Lois, et al., 2003, Small ubiquitin-like modifier modulates abscisic acid signaling in *Arabidopsis*, Plant Cell 15:1347-59); examples of other diverse eukaryotes for which SUMO proteins have been identified are also known: the tomato (Hanania, et al., 1999, Isolation of a novel SUMO protein from tomato that suppresses EIX-induced cell death, Plant J 19:533-41), the frog *Xenopus laevis* (Saitoh, et al., 1998, Ubc9p and the conjugation of SUMO-1 to RanGAP1 and RanBP2, Curr. Biol. 8:121-124), the fruit fly *Drosophila melanogaster* (Lehembre, et al., 2000, Covalent modification of the transcriptional repressor tramtrack by the ubiquitin-related protein Smt3 in *Drosophila* flies, Mol. Cell. Biol. 20:1072-1082), the nematode *Caenorhabditis elegans*, the yeast *Schizosaccharomyces pombe* (Tanaka, et al., 1999, Characterization of a fission yeast SUMO-1 homologue, pmt3p, required for multiple nuclear events, including the control of telomere length and chromosome segregation, Mol. Cell. Biol. 19:8660-8672), the malarial parasite *Plasmodium falciparum*, and the mold *Aspergillus nidulans*, among many others.

Any of the known or putative SUMO proteases (see FIG. 1B and the Sequence Listing for the sequences of their catalytic domains) may be utilized in the compositions and methods of the inventive subject matter to remove SUMO from the proteins of interest, provided that said SUMO protease is not *Saccharomyces cerevisiae* Ulp1. These SUMO proteases include but are not limited to those presented in an alignment in FIG. 1B. FIG. 1B is an alignment of the published polypeptide sequences of the catalytic domains of known and putative SUMO proteases from various organisms. The catalytic triad residues of the protease active site are indicated in bold. Only a representative set of previously described SUMO protease sequences are provided, and it is expected that all eukaryotes may have multiple SUMO proteases. There are two SUMO proteases in *S. cerevisiae* (Ulp1 and Ulp2), at least 6 in human (SENP1, 2, 3, 5, 6, and 7), and possibly more than a dozen in *Arabidopsis*.

The inventive SUMO fusion system has been successfully applied to express the enhanced green fluorescent protein (eGFP) in *E. coli*, purify the fusion, and generate the final product by cleavage with proteases in vitro. The inventive subject matter allows for: (1) the enhancement of the expression of under-expressed proteins; (2) increasing of the solubility of proteins that are insoluble or of low solubility; (3) protecting a protein of interest from degradation by intracellular N-terminus proteases by fusing SUMO sequences to the N-terminus; (4) cleaving the fusion protein in vitro to efficiently generate authentic proteins; and (5) generating proteins with novel N-termini amino acids.

Most known proteases, including the ones that are commonly used in recombinant protein processing, recognize small, 4-8 residues, and degenerate stretches of amino acid sequence and, as a consequence, often cleave within a protein of interest. Importantly, SUMO proteases are structure-specific enzymes that recognize the entire structure of a respective SUMO protein and not just several amino acid residues. The combination of properties of SUMO fusion proteins, along with the specificity and robustness of the respective proteases, creates a superior system for recombinant protein expression, purification and processing. Since SUMO fusion can both enhance recombinant protein yield and generate new N-termini, this technology provides an important tool for post-genomic biotechnology analyses.

In another embodiment of the inventive subject matter, kits are provided for performing the methods described herein, for use in effecting enhanced expression, solubility, secretion, purification, localization, and alteration of the amino terminus of a protein of interest. Such kits comprise a recombinant vector containing a nucleic acid sequence encoding a SUMO protein from human, mouse, insect, plant, yeast, or other eukaryotic organism, except not *Saccharomyces cerevisiae* Smt3, operably linked to a promoter suitable for expression in the desired host cell and a multiple cloning site suitable for cloning a nucleic acid encoding the protein of interest. The recombinant vector may also contain a nucleic acid sequence encoding for at least one purification tag.

Such kits comprise a recombinant vector containing a nucleic acid sequence encoding a SUMO molecule operably linked to a promoter suitable for expression in the desired cell and a multiple cloning site suitable for cloning a nucleic acid encoding the protein of interest in the reading frame ("in-frame") with the nucleic acid sequence encoding the SUMO molecule. The promoter is preferably a strong promoter and may be constitutive or regulated. Such promoters are well known in the art and include, but are not limited to, the examples of T7 in *E. coli*, CUP1 or ADH1 in yeast, or the polyhedrin promoter in the insect baculovirus system.

The recombinant vector may also contain a nucleic acid sequence encoding at least one purification tag in-frame with the sequence encoding the SUMO molecule. Purification tags are well known in the art (see Sambrook, J., E. F. Fritsch, and T. Maniatis, 1989, Molecular Cloning: A Laboratory Manual, Second Edition, Cold Spring Harbor Laboratory, Cold Spring Harbor, N.Y.; and Terpe, K., 2003, Overview of tag protein fusions: from molecular and biochemical fundamentals to commercial systems, Appl Microbiol Biotechnol 60:523-33) and include, but are not limited to: polyhistidine tags such as 6xHis, polyarginine tags, glutathione-S-transferase (GST), maltose binding protein (MBP), S-tag, influenza virus HA tag, thioredoxin, staphylococcal protein A tag, the FLAG™ epitope, AviTag epitope, which also permits subsequent biotinylation, and the c-myc epitope. Materials and methods for the purification of fusion proteins via purification tags are also well known in the art (see Sambrook et al., supra, and such commercial sources as the Novagen catalog, 2004, as well as the Examples below). Reagents, including but not limited to at least one solid support capable of binding the purification tag, lysis buffers, wash buffers, and elution buffers may also be included in the inventive kits.

Such kits may further comprise a protease composition capable of cleaving a SUMO molecule from the fusion protein and optional purification tag. A more complete kit embodiment includes at least one solid phase capable of binding at least one purification tag; appropriate buffers including wash and cleavage buffers; instruction material; and frozen stocks of appropriate host cells. The kits may also further comprise reagents for altering the nucleic acid encoding a protein of interest to generate amino termini which are different from those native to the wild-type protein. Methods for altering the nucleic acid are well known in the art and include, but are not limited to, site-directed mutagenesis and oligonucleotide-based site-directed mutagenesis (see commercial sources such as the BD Biosciences, Qiagen, and Stratagene catalogs, 2004; Ausubel et al., eds., 1995, Current Protocols in Molecular Biology, John Wiley and Sons, Inc.).

FIG. 2 is a schematic representation of a cloning strategy used to generate various SUMO fusion proteins. In this cloning strategy, the nucleic acid sequence encoding the protein to be expressed as a fusion with SUMO is amplified by PCR with primers that introduce a Bsa I site (or other type II restriction enzyme capable of generating an ACCT overhang) at the 5' end and BamHI site (or other site in the multiple cloning sequence of pET24) at the 3' end. The vector encoding SUMO contains, in this example, a BsaI site and a BamHI site at the 3' end of the SUMO encoding region. The PCR product and vector are cleaved by BsaI and BamHI (or other appropriate restriction enzyme) for insertion of the cleaved PCR product into the vector. The ligation reconstitutes the codons encoding the Gly-Gly motif, the cleavage site of the resulting fusion protein.

Figure 3A:
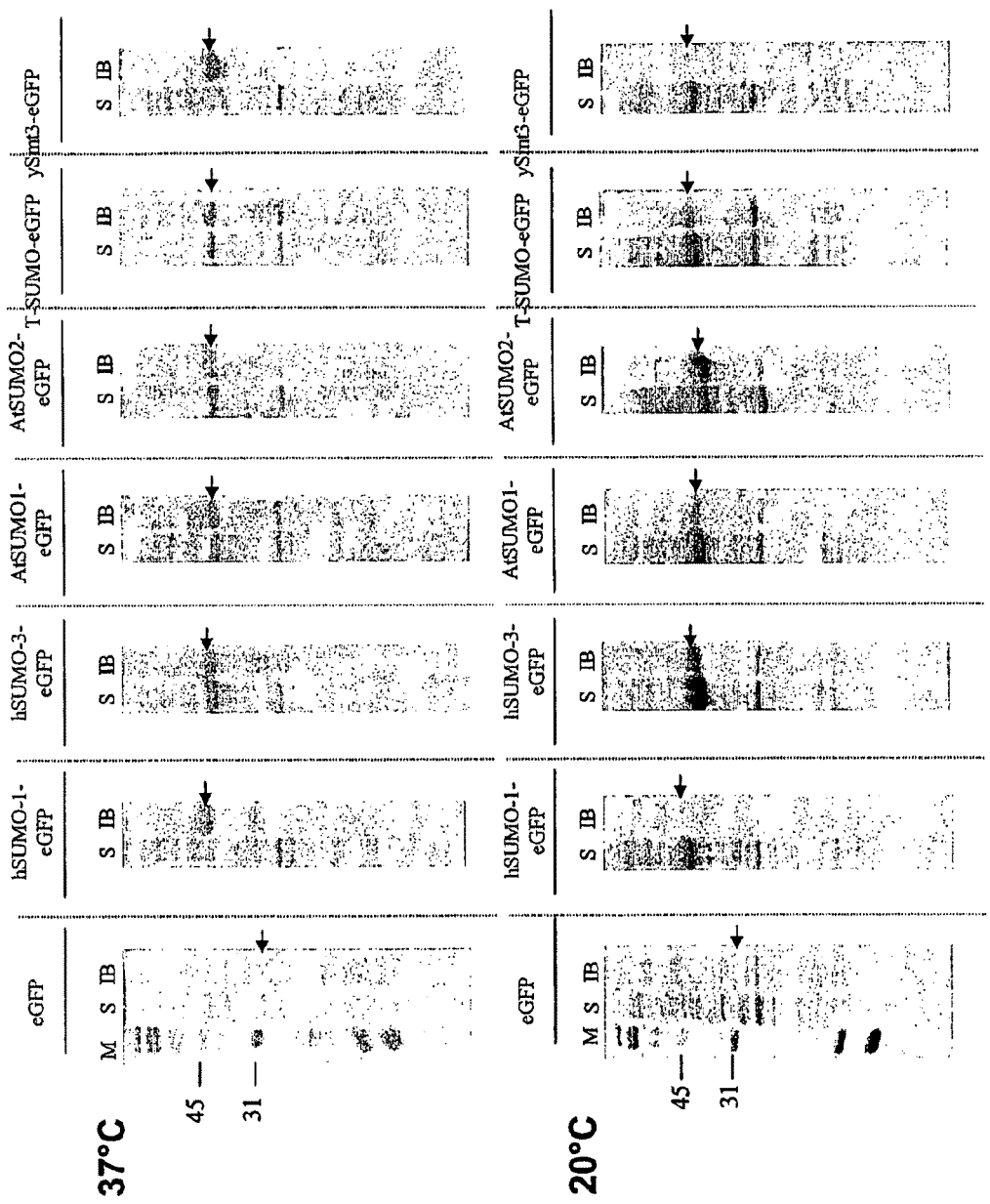
FIG. 3A shows a Coomassie-stained SDS-PAGE gel of soluble (S) and insoluble inclusion body (IB) fractions from pET24d-6xHis-SUMO-eGFP-containing cells induced with IPTG.

FIG. 3A shows a Coomassie-stained gel that demonstrates that the attachment of various SUMO proteins to the amino-terminus of target protein eGFP increases the expression and/or enhances the solubility of the protein in *E. coli*. Shown are soluble (S) and insoluble inclusion body (IB) fractions from pET24d-6xHis-SUMO-eGFP-containing cells that were induced with IPTG and grown at 37° C. or 20° C.

Figure 3B:
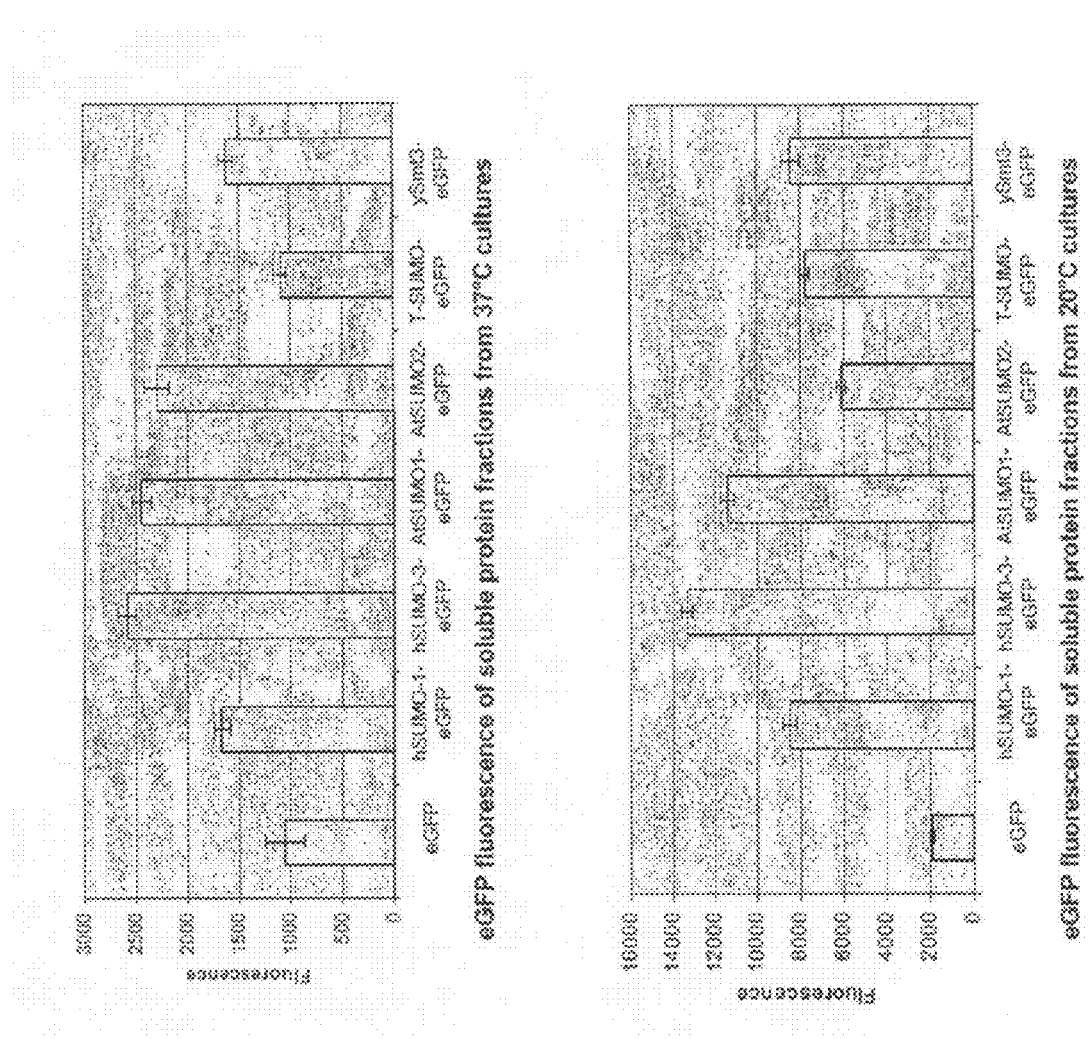
FIG. 3B shows fluorescence comparisons of eGFP unfused or fused with described SUMO tags.

FIG. 3B shows a quantitative comparison of yields of different SUMO-eGFP fusions in soluble fractions, by way of eGFP fluorescence. The data are presented in arbitrary units and the values were from three fluorimetric measurements (mean with standard deviations) under the same conditions.

Figure 4A:
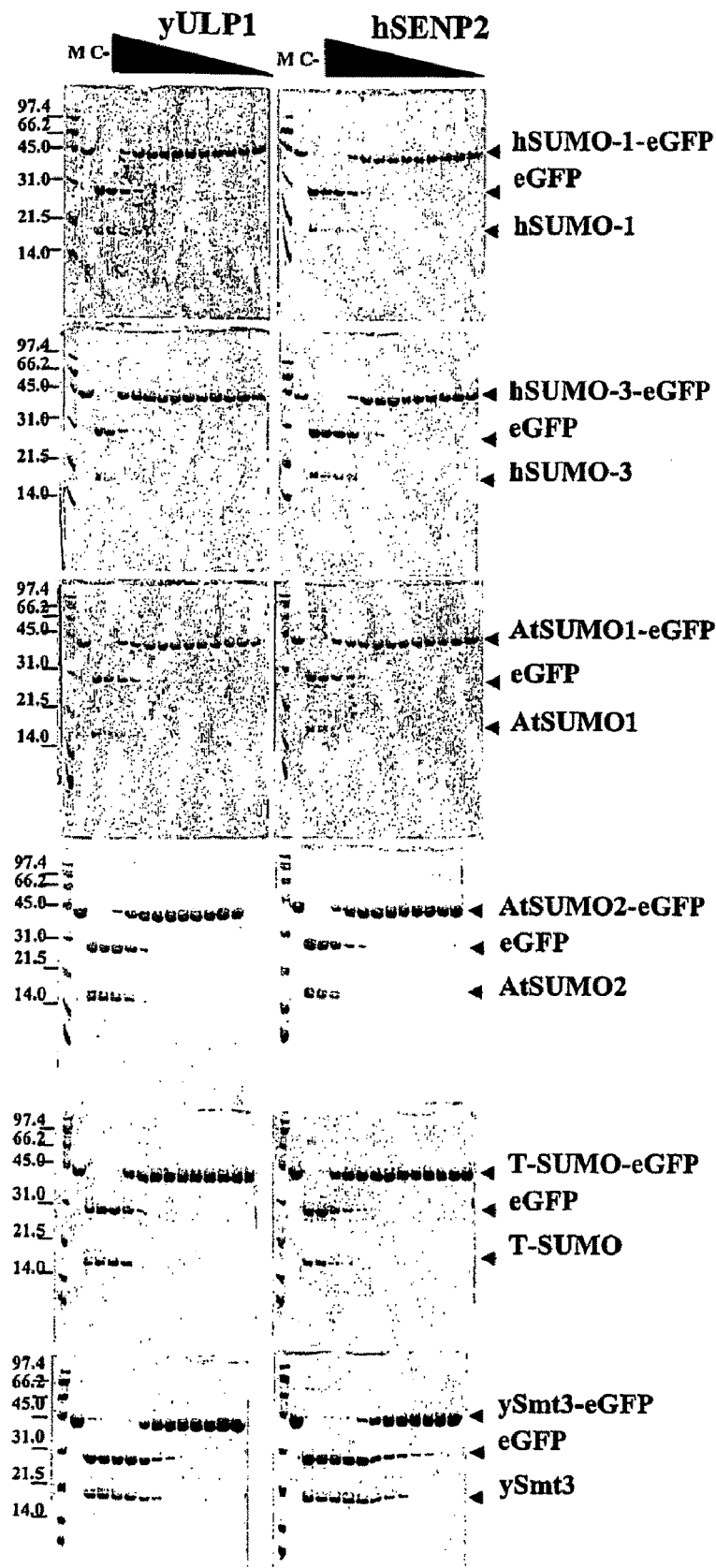
FIG. 4A shows a Coomassie-stained SDS-PAGE gel of a 2-fold dilution series comparing human SENP2 and yeast Ulp1 used to cleave a variety of SUMO-eGFP fusions.

FIG. 4A shows Coomassie-stained gels of in vitro reactions in which 2-fold dilution series of human SENP2 or yeast Ulp1 were used to cleave a variety of SUMO-eGFP fusions, demonstrating the different efficiencies and specificities of cleavage.

Figure 4B:
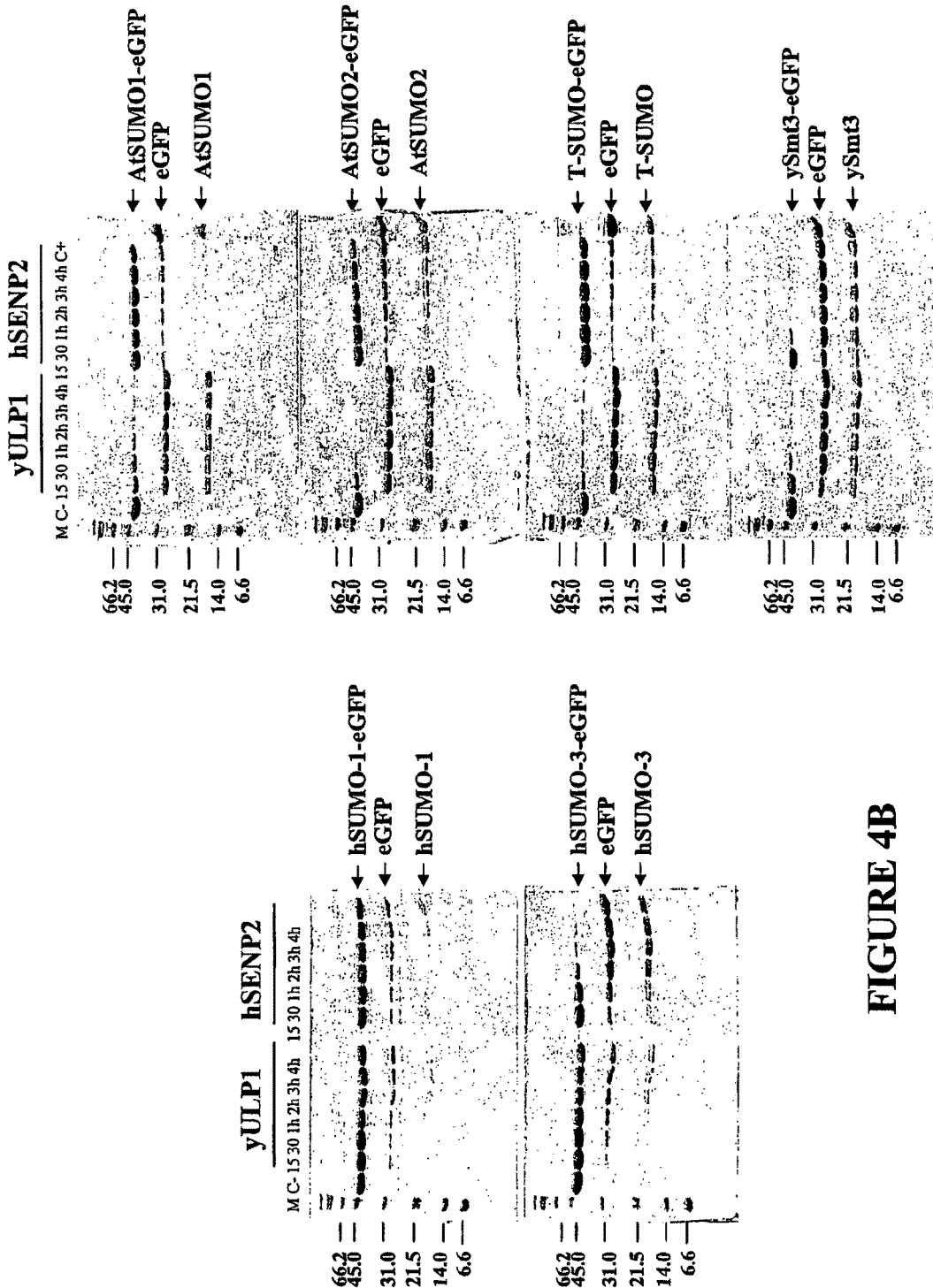
FIG. 4B shows a Coomassie-stained SDS-PAGE gel of a time course comparing cleavage of various SUMO-eGFP fusions by human SENP2 and yeast Ulp1.

FIG. 4B shows Coomassie-stained gels of time courses of cleavage of various SUMO-eGFP fusions by human SENP2 or yeast Ulp1, demonstrating the different efficiencies and specificities of cleavage.

Figure 4C:
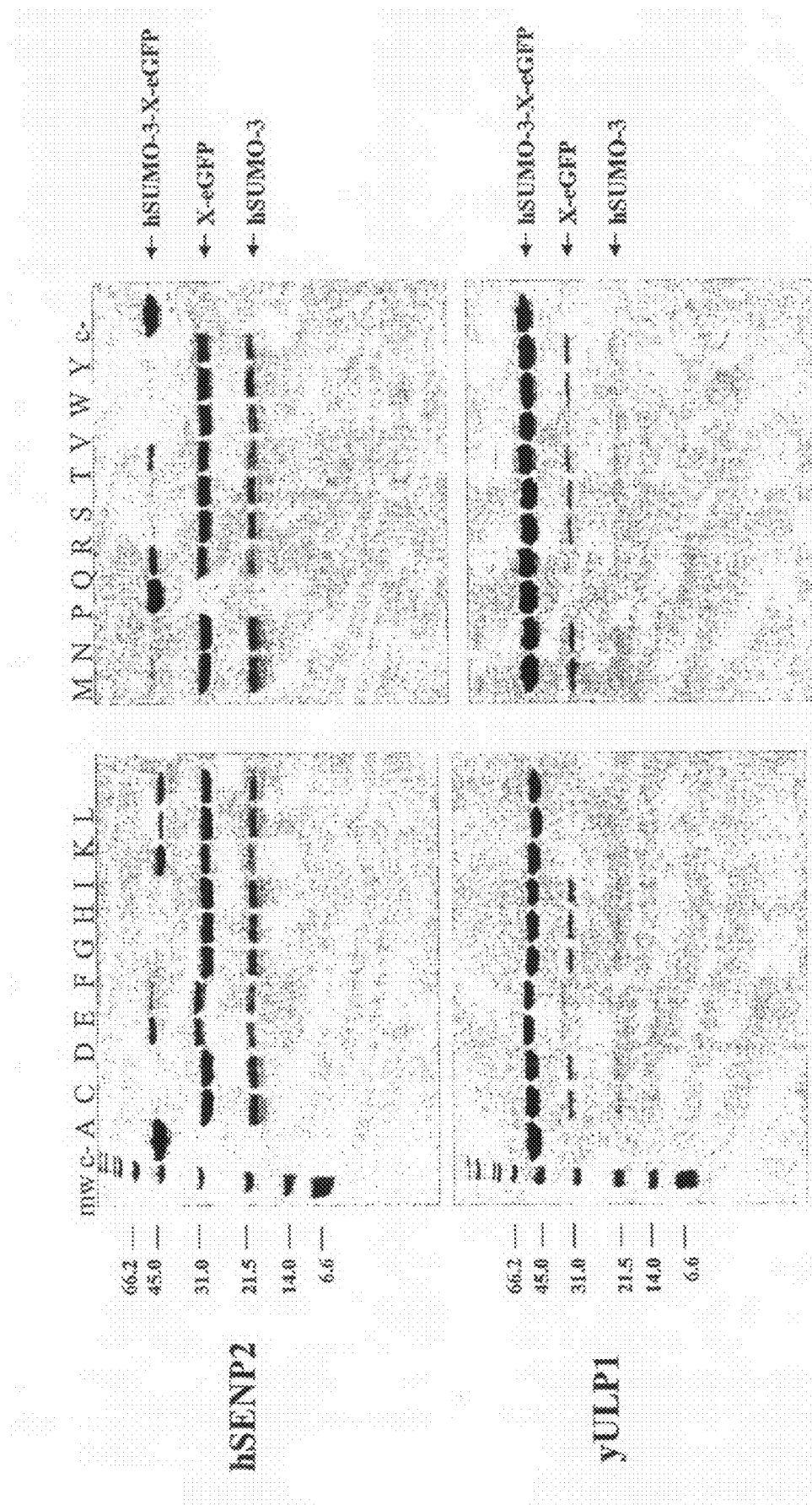
FIG. 4C shows Coomassie-stained SDS-PAGE gels comparing human SENP2 and yeast Ulp1 used to cleave hSUMO3-eGFP fusions with each of the 20 amino acids at the N-terminus of eGFP.

FIG. 4C shows Coomassie-stained SDS-PAGE gels comparing human SENP2 and yeast Ulp1 used to cleave hSUMO3-eGFP fusions with each of the 20 amino acids at the N-terminus of eGFP, demonstrating the improved efficiencies and specificities of cleavage by SENP2.

Figure 5:
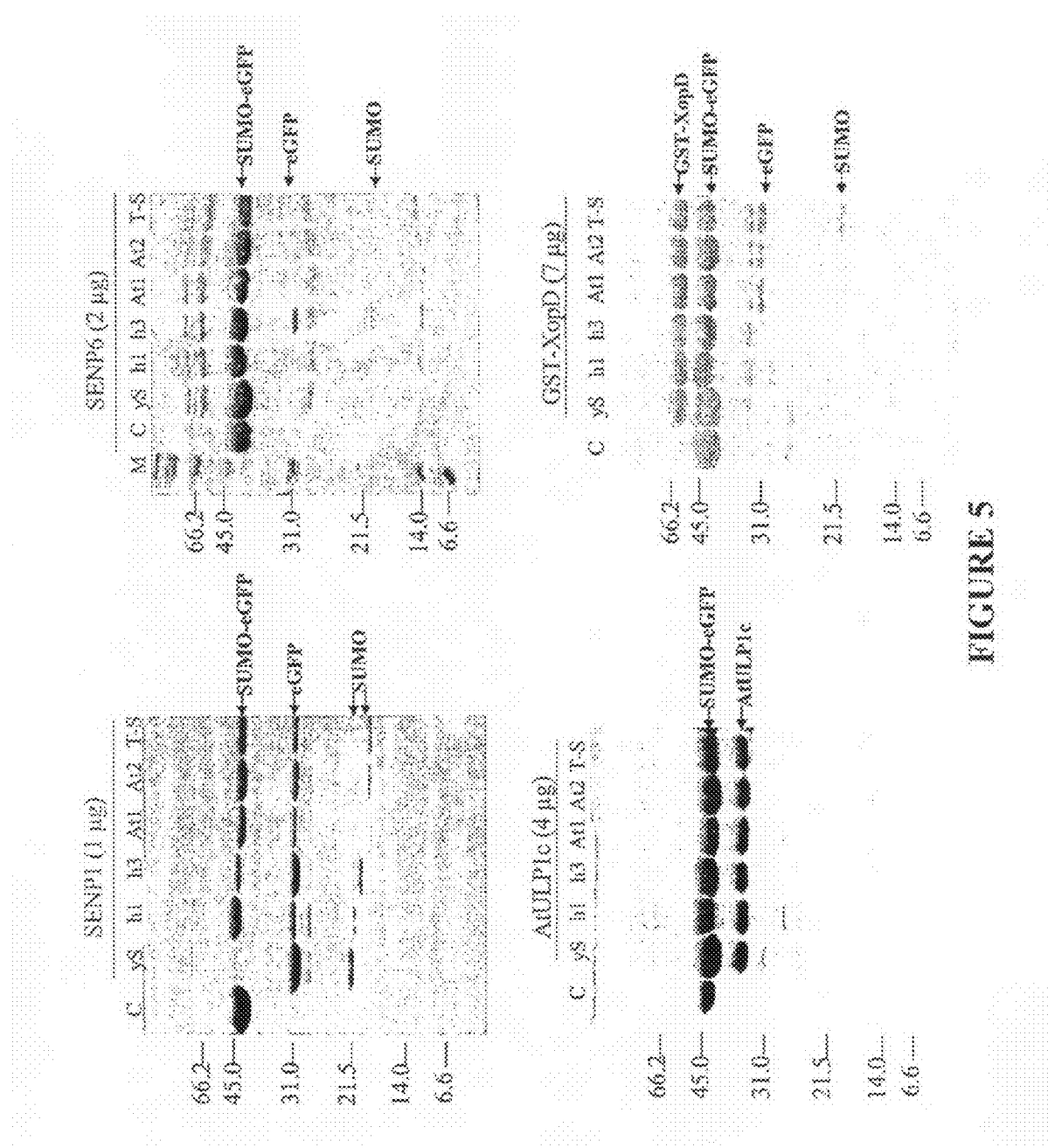
FIG. 5 shows a Coomassie-stained SDS-PAGE gel of in vitro cleavage reactions of the SUMO proteases SENP1, SENP6, AtULP1c, and GST-XopD for various fusion proteins.

FIG. 5 shows Coomassie-stained gels of in vitro reactions of four additional SUMO proteases from several species against various SUMO-eGFP fusions, demonstrating that various SUMO protease catalytic domains are capable of cleaving different SUMO proteins from GFP with differing specificities and efficiencies.

Figure 6A:
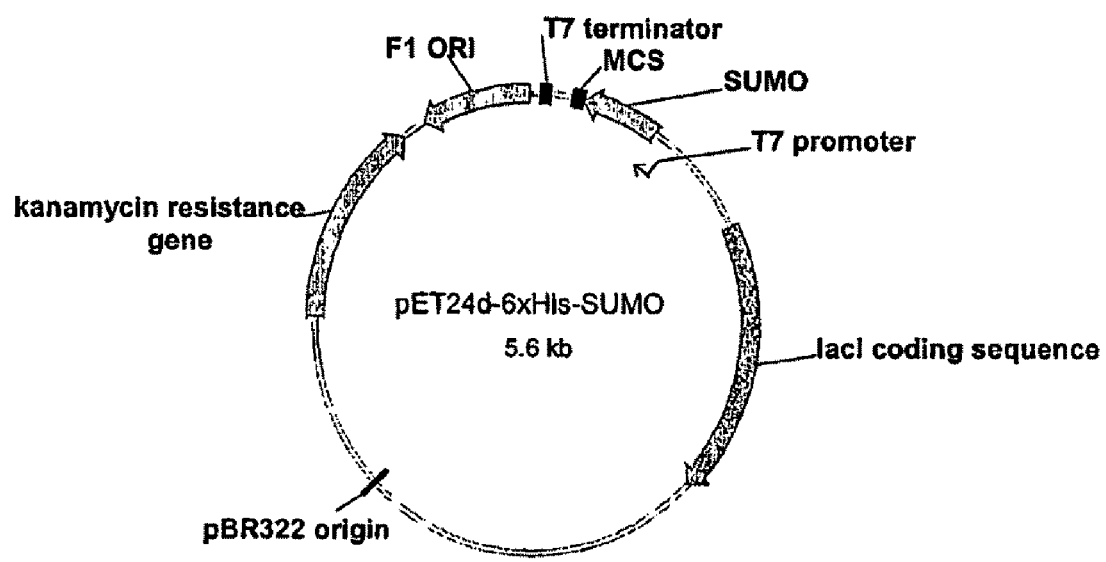
FIG. 6A is a map of an exemplary plasmid pET24d-6xHis-SUMO expression vector, as used in the inventive subject matter.

FIG. 6A is a map of an exemplary plasmid pET24d-6xHis-SUMO expression vector, as used in the inventive subject matter; it can contain any of the SUMO proteins described in this application or from any eukaryote. The parental vector used for the present data was pET24d, but alternative versions of pET vectors or other expression plasmids may be used. FIG. 6B shows the regions that flank the sequences of 6xHis-SUMO in the plasmid (using hSUMO-3 as an example).

The Sequence Listing contains the amino acid and nucleotide sequence sequences of the various SUMO proteins used in these studies.

SEQ ID NO: 1 and SEQ ID NO: 2 depict the amino acid sequence and nucleotide sequence of human SUMO-1 (hSUMO-1).

SEQ ID NO: 4 and SEQ ID NO: 4 depict the amino acid sequence and nucleotide sequence of human SUMO-3 (hSUMO-3).

SEQ ID NO: 5 and SEQ ID NO: 6 depict the amino acid sequence and nucleotide sequence of *Arabidopsis thalania* SUMO1 (AtSUMO1).

SEQ ID. NO: 7 and SEQ ID NO: 8 depict the amino acid sequence and nucleotide sequence of *Arabidopsis thalania* SUMO2 (AtSUMO2).

SEQ ID NO: 9 and SEQ ID NO: 10 depict the amino acid sequence and nucleotide sequence of tomato (*Lycopersicum esculentum*) T-SUMO.

SEQ ID NO: 11 and SEQ ID NO: 12 depict the amino acid sequence and nucleotide sequence of *Saccharomyces cerevisiae* Smt3 (ySmt3, ySUMO).

SEQ ID NO: 13 and SEQ ID NO: 14 depict the amino acid sequence and nucleotide sequence of 6xHis-tagged human SUMO-1.

SEQ ID NO: 15 and SEQ ID NO: 16 depict the amino acid sequence and nucleotide sequence of 6xHis-tagged human SUMO-3.

SEQ ID NO: 17 and SEQ ID NO: 18 depict the amino acid sequence and nucleotide sequence of 6xHis-tagged *Arabidopsis thalania* SUMO1.

SEQ ID NO: 19 and SEQ ID NO: 20 depict the amino acid sequence and nucleotide sequence of 6xHis-tagged *Arabidopsis thalania* SUMO2.

SEQ ID NO: 21 and SEQ ID NO: 22 depict the amino acid sequence and nucleotide sequence of 6xHis-tagged tomato T-SUMO.

SEQ ID NO: 23 and SEQ ID NO: 24 depict the amino acid sequence and nucleotide sequence of 6xHis-tagged *Saccharomyces cerevisiae* Smt3.

SEQ ID NO: 25 and SEQ ID NO: 26 depict the amino acid sequence and nucleotide sequence of eGFP (enhanced green fluorescent protein).

SEQ ID NO: 27 and SEQ ID NO: 28 depict the amino acid sequence and nucleotide sequence of the N-terminally tagged 6xHis-eGFP protein as it appears in pET-6xHis-eGFP.

SEQ ID NO: 29 and SEQ ID NO: 40 depict the amino acid sequence and nucleotide sequence of 6xHis-hSUMO-1-eGFP.

SEQ ID NO: 41 and SEQ ID NO: 42 depict the amino acid sequence and nucleotide sequence of 6xHis-hSUMO-3-eGFP.

SEQ ID NO: 43 and SEQ ID NO: 44 depict the amino acid sequence and nucleotide sequence of 6xHis-AtSUMO1-eGFP.

SEQ ID NO: 45 and SEQ ID NO: 46 depict the amino acid sequence and nucleotide sequence of 6xHis-AtSUMO2-eGFP.

SEQ ID NO: 47 and SEQ ID NO: 48 depict the amino acid sequence and nucleotide sequence of 6xHis-T-SUMO-eGFP.

SEQ ID NO: 49 and SEQ ID NO: 40 depict the amino acid sequence and nucleotide sequence of 6xHis-ySmt3-eGFP.

SEQ ID NO: 41 and SEQ ID NO: 4 depict the amino acid sequence and nucleotide sequence of human SENP1 (hSENP1).

SEQ ID NO: 43 and SEQ ID NO: 44 depict the amino acid sequence and nucleotide sequence of human SENP2 (hSENP2).

SEQ ID NO: 45 and SEQ ID NO: 46 depict the amino acid sequence and nucleotide sequence of human SENP6 (hSENP6).

SEQ ID NO: 47 and SEQ ID NO: 48 depict the amino acid sequence and nucleotide sequence of *Arabidopsis thalania* ULP1c (AtULP1c).

SEQ ID NO: 49 and SEQ ID NO: 50 depict the amino acid sequence and nucleotide sequence of *Saccharomyces cerevisiae* Ulp1 (yeast Ulp1, yUlp1).

SEQ ID NO: 51 and SEQ ID NO: 52 depict the amino acid sequence and nucleotide sequence of a GST fusion of the catalytic domain of the *Xanthomonas campestris* pathovar vesicatoria protease XopD (GST-XopD).

SEQ ID NO: 53-68 depict the sequence of PCR primers.

SEQ ID NO: 69 AND SEQ ID NO: 70 depict the amino acid sequence and nucleotide sequence of 6xHis-hSUMO-3-X-eGFP, where "X" represents each of the 20 naturally occurring amino acids tested to demonstrate the ability to make proteins with a novel, i.e. non-methionine, N-terminal amino acid.

EXAMPLES

The following examples are illustrative of the inventive subject matter and are not intended to be limitations thereon. Unless otherwise indicated, all percentages are based upon 100% by weight of the final composition. All starting materials, reagents, and solvents were commercially available and were used either as obtained from commercial suppliers, synthesized according to known literature procedures, and/or washed, dried, distilled, recrystallized, and/or purified before use.

Example 1

Design and Construction of *E. coli* Expression Vectors

The original vector backbone was developed using pET 24d vector from Novagen. pET24d uses a T7 promoter system that is inducible with IPTG. The vector has a kanamycin selection marker and does not contain any translation terminator. This vector was modified by PCR to encode an N-terminal 6xHis tag followed by a BsaI site, becoming the plasmid pET24d-6xHis.

Example 2

Construction of 6xHis-SUMO and 6xHis-SUMO-eGFP Expression Plasmids

The amino-terminal 6xHis-tagged SUMO fusion vectors were constructed as follows. For human SUMO-1, a PCR product was generated with the primers 5'-TTTTTTC- CATGGGTCATCACCATCATCATCACTCT-
GACCAGGAGGCAAAAC-3' (SEQ ID NO: 53) and
5'-TTTTTTGGATCCGGTCTCAACCTC-
CCGTTTGTTCCTGATAAAC-3' (SEQ ID NO: 54) using a
SUMO-1 gene as a template (kind gift of K. I. Kim). For
Saccharomyces cerevisiae Smt3, a PCR product was generated with the primers 5'-CCATGGGTCATCACCATCAT-
CATCACGGGTCGGACTCAGAAGTCAATCAA-3' (SEQ
ID NO: 55) and 5'-GGATCCGGTCTCAACCTCCAATCT-
GTTCGCGGTGAG-3' (SEQ ID NO: 56) using a modified
SUMO (Smt3) gene as a template (kind gift of Erica
Johnson). Specifically, the SUMO (SEQ ID NO: 12) used
throughout the examples provided herein contains an adenine
nucleotide at position 229 in place of a guanine nucleotide
reported in the reported SUMO sequence (GenBank accession number U27233). This alteration produces an alanine
instead of a threonine in the encoded amino acid sequence
(compare SEQ ID NO: 11 with GenBank Accession No.
Q12306). Although the following examples employ the
altered version of SUMO, the instant inventive subject matter
includes the utilization of the "wild-type" SUMO as provided
in the above listed GenBank Accession Nos. For both
hSUMO-1 and ySmt3, the PCR fragment was double-digested with NcoI and BamHI and then ligated into pET24d
that had been similarly digested, resulting in 6xHis-
hSUMO-1 and 6xHis-ySmt3 plasmids.

To make 6xHis-SUMO-1 and 6xHis-Smt3 fusions with
eGFP, the eGFP sequence (46) was amplified with the primers
5'-GGTCTCAAGGTATGGTGAGCAAGGGCGAGGAGC-
3' (SEQ ID NO: 57) and 5'-AAGCTTATTACTTGTA-
CAGCTCGTCCATGCC-3' (SEQ ID NO: 58). The PCR
product was purified and double-digested with BsaI and HindIII and then ligated into pET24d-6xHis-SUMO vectors that
had been similarly digested.

For human SUMO-3, a PCR product was generated with
the primers 5'-GATCGAACCTGCATATAGGTATGTC-
CGAGGAGAAGCCCAAG-3' (SEQ ID NO: 59) and
5'-GATCGGATCCGGTCTCAACCTCCCGTCT-
GCTGCTGGAACACG-3' (SEQ ID NO: 60) using SUMO-
3-containing MGC cDNA clone #3505840 (Open Biosystems). For Arabidopsis thalania SUMO1, a PCR product was
generated with the primers 5'-GATCGAACCTGCATATAG-
GTATGTCTGCAAACCAGGAGGA-3' (SEQ ID NO: 61)
and 5'-GATCGGATCCGGTCTCAACCTCCAGTCT-
GATGGAGCATCGC-3' (SEQ ID NO: 62) using cDNA
clone U17495 from the Arabidopsis Biological Resource
Center. For Arabidopsis thalania SUMO2, a PCR product
was generated with the primers 5'-GATCGACGTCTCAAG-
GTATGTCTGCTACTCCGGAAGAAG-3' (SEQ ID NO: 63)
and 5'-GATCGGATCCGGTCTCAACCTCCAGTCT-
GATGAAGCATTGCA-3' (SEQ ID NO: 64) using cDNA
clone U21609 from the Arabidopsis Biological Resource
Center. For tomato T-SUMO, a PCR product was generated
with the primers 5'-GATCGAACCTGCATATAGGTAT-
GTCTGCTAGCGGCGGCACC-3' (SEQ ID NO: 65) and
5'-GATCGGATCCGGTCTCAACCTC-
CAGTTTGATGTAGCATTG-3' (SEQ ID NO: 66) a
T-SUMO plasmid kindly provided by M. B. Mudgett.

The PCR fragments were double-digested with BamHI and
BfuAI (hSUMO-3, AtSUMO1, and T-SUMO) or BsmBI (AtSUMO2), and then ligated into pET24d-6xHis that had been
digested with BamHI and BsaI.

The eGFP sequence was amplified with the primers
5'-TTTTTTGGTCTCAAGGTATGGTGAG-
CAAGGGCGAGGGCGAGGAGC-3' (SEQ ID NO: 67) and
5'-TTTTTTCTCGAGTTACTTGTACAGCTCGTCCATG-
3' (SEQ ID NO: 68). The PCR product was purified and
double digested with BsaI and XhoI and then ligated into the
pET24d-6xHis-SUMO vectors which had been similarly
digested.

Plasmids were sequenced to confirm the presence of correct sequence in each.

Example 3

Expression and Purification of 6xHis-eGFP and
6xHis-SUMO-eGFP Proteins

To test and compare expression of eGFP and the SUMO-
eGFP fusion proteins, a single colony of the *E. coli* Rosetta
strain (Novagen) containing each of the SUMO-eGFP plasmids was inoculated into 5 ml of Luria-Bertani (LB) media
containing 100 μg/ml Kanamycin and 30 μg/ml chloramphenicol. This strain is derived from the lambda DE3 lysogen
strain and carries a chromosomal copy of the IPTG-inducible
T7 RNA polymerase along with tRNAs on a pACYC-based
plasmid. The cells were grown at 37° C. overnight with shaking at 250 rpm. The next morning the overnight culture was
transferred into 100 ml fresh medium to permit exponential
growth. When the $OD_{600}$ value reached ~0.6-0.7, protein
expression was induced by addition of 1 mm IPTG (isopropyl-β-D-thiogalactopyranoside), followed by prolonged
cultivation at either 37° C. for 3 hours or 20° C. overnight
(~15 hours).

After the *E. coli* cells were harvested from LB medium
(100 ml) by centrifugation (8,000×g for 10 min at 4° C.), the
cell pellets were suspended in 6 ml of lysis buffer (PBS
containing 300 mM NaCl, 10 mM imidazole, 0.1% Triton
X100 and 1 mM PMSF, pH 8.0). The cells were lysed by
sonication (at 50% output for 5×30 second pulses). The sonication was conducted with the tube jacketed in wet ice and 1
min intervals between the pulse cycles to prevent heating.
After the lysates were incubated with DNase and RNase
(each at 40 μg/ml) for 15 min to digest nucleic acids, they
were centrifuged at 20,000 g for 30 min at 4° C., and the
supernatant (soluble protein fractions) was collected. The
pellets was washed once with 6 ml of the lysis buffer to further
extract the soluble fraction; the wash (6 ml) was combined
with previous extract (6 ml) to make final volume of 12 ml for
the soluble protein sample.

Insoluble protein samples were prepared from *E. coli*
inclusion bodies. Briefly, after the extract containing soluble
proteins were removed, the pellets containing inclusion bodies were suspended in the denaturing solubilization buffer
(Novagen) that contained 50 mM CAPS (pH 11.0), 0.3%
N-laurylsarcosine, and 1 mM DTT and incubated for 20 min
at room temperature with shaking. The extract (insoluble
protein fraction) was obtained by high-speed centrifugation
(80,000×g for 20 min at 4° C.).

For detection of expressed proteins using SDS-PAGE, 5 μl of
the samples prepared above were mixed with 3 μl of SDS-
PAGE sample buffer containing SDS and β-mercaptoethanol
and were heated at 95° C. for 5 min to facilitate denaturation
and reduction of proteins. Proteins were visualized using 15%
SDS-polyacrylamide gels with Tris-Glycine running buffer
and Coomassie blue staining.

Example 4

Purification of 6xHis-SUMO-eGFP Proteins

All of the SUMO-eGFP fusions were expressed in *E. coli*
as described above. Since all have 6xHis-tags, the soluble
proteins extracted from *E. coli* cells were purified using Ni- NTA affinity chromatography under native conditions and a BioLogic Duo-Flow FPLC system (Bio-Rad) was used for high-throughput fractionations. Briefly, the cell lysate (typically, 20-40 ml containing 0.2-0.5 g proteins) was loaded onto a column containing ~10 ml Ni-NTA superflow resin (Qiagen, Valencia, Calif.) and the unbounded proteins (flow-through) were eluted out. The resin was extensively washed with ~50-100 ml of Wash Buffer (PBS containing 20 mM imidazole and 300 mM NaCl, pH 8.0) until $UV_{280}$ reached or fell below the base line (UV value=0). Finally, the 6xHis tagged SUMO-fusion proteins were eluted by Elution Buffer (PBS containing 300 mM imidazole and 300 mM NaCl, pH 8.0). The purified SUMO-fused proteins eluted as a single isolated UV peak. The proteins with high $UV_{280}$ values were collected in 4 ml fractions that were checked on SDS gels and pooled. The purified SUMO-eGFP fusion proteins were dialyzed with 3.5 kDa cutoff membranes against PBS pH ~7.5 overnight at 4° C. to remove high salt and imidazole.

Example 5

Cleavage of SUMO-eGFP Fusion Proteins by SUMO Proteases

To evaluate and compare effectiveness of different SUMO proteases on cleavage of different SUMO-GFP fusions, Applicants either used serially diluted amounts of enzymes to digest substrates (different ratios of enzyme to substrate) for a given time or used the same amount of enzymes to digest substrates at a fixed ratio for over a period of time (time-course assays). For all cleavage reactions, Applicants used PBS buffer (pH ~7.5) containing either β-mercaptoethanol or DTT and incubated at 30° C.

For FIG. 4A, serially diluted amounts of yULP1 or hSENP2, starting at 1 μg (0.5 μg for the ySmt3 experiment) and successively decreasing 2-fold by titration, were used to cleave 10 μg of SUMO-GFP in PBS (pH 7.5) containing 5 mM β-mercaptoethanol at 30° C. for 1 hour. M=Molecular weight markers; C-=Negative controls (SUMO-eGFP without enzyme). Arrows highlight expected/observed migration positions of respective expressed proteins.

For the time course in FIG. 4B, cleavage reactions of different SUMO-GFP fusions by yULP1 and hSENP1 were performed enzyme to substrates ratio of 1:1000 (10 μM enzyme to 10 mM SUMO-GFP) and incubated in PBS (pH 7.5) containing 5 mM β-mercaptoethanol at 30° C. over a period of time (15 min., 30 min., and 1, 2, 3, and 4 hrs.). M=Molecular weight markers; C-=Negative controls (SUMO-GFP without enzyme). Arrows highlight expected/observed migration positions of respective expressed proteins.

For cleavage of different SUMO-eGFP fusions by hSENP1, hSENP6, AtULP1c and GST-XopD in FIG. 5, 10 mM of each substrate was added to the enzymes at the amount indicated and incubated in PBS (pH 7.5) containing 5 mM β-Mercaptoethanol at 30° C. for 1 h. Arrows highlight expected/observed migration positions of respective proteins.

Example 6

Attachment of Various SUMO Proteins to the N-Terminus of eGFP Enhances the Expression of the Protein in E. coli The design and construction of all the pET vectors expressing eGFP and SUMO-eGFP fusions has been described above. The DNA sequences of the SUMO proteins, eGFP, the fusion constructs, and translation frames are shown in the Sequence Listing. FIG. 3 shows the expression pattern of 6xHis-eGFP, 6xHis-hSUMO-1-eGFP, 6xHis-hSUMO-3-eGFP, 6xHis-AtSUMO1-eGFP, 6xHis-AtSUMO2-eGFP, 6xHis-T-SUMO-eGFP, and 6xHis-ySmt3-eGFP. Induced E. coli cells grown at 37° C. or 20° C. were ruptured by sonication, and soluble fractions and insoluble inclusion bodies were prepared and analyzed on SDS-polyacrylamide gels. The stained gel (FIG. 3) shows that un-fused eGFP is generally poorly expressed in E. coli, while all of the SUMO tags from diverse species increase the overall expression of eGFP. Notably, certain SUMO tags increased expression and solubility more effectively than others. At 37° C., hSUMO-3 and AtSUMO1 produced the most overall eGFP protein and the largest amount of soluble eGFP, while yeast Smt3, AtSUMO2, and T-SUMO resulted in less eGFP expression and solubility. At 20° C., all SUMO fusions demonstrated improved expression and/or solubility. The most effective tags under these conditions were hSUMO-1 and hSUMO-3, which produced a large amount of overall expression and soluble eGFP, with a minor amount of insoluble eGFP. Yeast Smt3 and AtSUMO1 resulted in very low amounts of insoluble eGFP fusion, but their amounts of overall and soluble eGFP were considerably lower than those from the human SUMO fusion strains. Importantly, human SUMO-3 was one of the best expression tags under the two conditions used, while yeast Smt3 was one of the least effective under the same conditions, indicating that hSUMO-3 is a superior agent for expression enhancement in E. coli than is yeast Smt3, the SUMO protein employed in previously described expression systems. The superiority of hSUMO-3 over ySmt3 as an expression tag is surprising and could not be predicted from sequence analysis or other previously published data.

Example 7

Quantitation of Soluble eGFP and SUMO-eGFP by Fluorescence

Because properly folded, active eGFP has fluorescent properties, the expressed eGFP fusions in this study could be quantified by using fluorimetry. The quantitation was only performed on the soluble fractions, since the insoluble proteins from bacterial inclusion bodies are usually incorrectly folded. Specifically, the eGFP fluorescence in soluble fractions (approximately 100 μg of proteins in a final volume of 40 μl) was measured using a Fluoroskan Ascent FL fluorimeter (LabSystems, Helsinki, Finland) with an excitation 485 nm/emission 510 nm filter set with the exposure set to 0.4 s. The data are presented in arbitrary units. A graphic representation of the results of the fluorescence analyses was drawn using Microsoft Excel.

FIG. 3B shows comparisons of fluorescence from eGFP un-fused or fused with different SUMO tags. From either 37° C. or 20° C. culture, the levels of soluble hSUMO3-eGFP and AtSUMO1-eGFP were significantly higher than that of ySmt3-eGFP ($p<0.01$); especially, hSUMO3-eGFP was more than 50% higher compared with ySmt3-eGFP. The yield of soluble AtSUMO2-eGFP was higher than that of ySmt3 from 37° C. culture, but lower from 20° C. eGFP without fusion was poorly expressed, since its fluorescence was significantly lower than that of any SUMO-fused eGFP ($p<0.01$). The hSUMO1-eGFP level was very similar to that of ySmt3-eGFP ($p>0.05\%$) and T-SUMO-eGFP was significantly lower than ySmt3-eGFP at 37° C. ($p<0.05$).

Quantitation of SUMO-eGFP by measurement of the eGFP fluorescence of the soluble fractions (FIG. 3B) confirm that, compared to ySmt3, hSUMO-3 yields significantly higher levels of soluble protein and overall expression (soluble+insoluble) at both 37° C. and 20° C. The soluble fractions demonstrated a 1.6-fold advantage of hSUMO-3 over ySmt3. The generation of larger quantities of soluble protein of interest is particularly important, because it has the potential to impact both the quality of the protein and its ease of purification. A soluble protein is more likely to be properly folded and will typically not require further treatment before purification, while insoluble protein must be rendered soluble by certain methods (such as detergents or chaotropic agents) and often subjected to lengthy refolding/dialysis, adding time and effort to the purification, as well as increasing the chances that a protein will be or become damaged and/or inactive. Obtaining a larger yield of soluble protein by way of hSUMO-3 is expected to obviate the need to work with insoluble protein; although an insoluble fraction of hSUMO-3 fusion is generated, it can be discarded, and yield will still be better than that of ySmt3 fusion.

The higher yield of overall and soluble expressed protein of interest from hSUMO-3 fusion as compared to ySmt3 or most other fusions tested is an unexpected and surprising finding that could not be predicted based on their amino acid sequences or general classification as SUMO proteins.

Example 8

Direct Comparison of Human SENP2 and Yeast Ulp1 Proteases Demonstrates Different Levels of Activity and Preferences for Certain SUMO Proteins In Vitro The design and construction of the pET vectors expressing SUMO protease catalytic domains of human SENP2 and yeast Ulp1 has been described above. The DNA sequences and translation frames of the proteases are shown in the Sequence Listing. These proteases and each of the six SUMO-eGFP fusions described above were expressed in *E. coli* and purified on nickel columns by way of the 6xHis tags on the C-termini (proteases) or N-termini (SUMO-eGFP's) of the proteins. In vitro reactions were performed in which each purified protease was used in reactions with each of the purified SUMO-eGFP proteins, and the cleavage results were analyzed by Coomassie-stained SDS-PAGE gels (FIG. 4).

For FIG. 4A, dilution series of the proteases were performed, where a fixed amount of each SUMO-eGFP was incubated for 1 hour at 30 C with sets of 2-fold dilutions of the enzymes. As shown in FIG. 4A, there were significant differences in the abilities of hSENP2 and yUlp1 to cleave fusions with different SUMO proteins. Specifically, hSENP2 was able to cleave hSUMO-3-eGFP at least 4-fold better than an identical amount of yUlp1. In addition, hSENP2 was able to cleave hSUMO-1 and ySmt3 fusions somewhat more effectively (about 2-fold) than yUlp1. On the other hand, yUlp1 had a distinct advantage in the cleavage of T-SUMO-eGFP and a slight advantage in the cleavage of AtSUMO2-eGFP. Both hSENP2 and yUlp1 cleaved the AtSUMO1 fusion similarly.

In addition to dilution series, a time-course experiments were performed with hSENP2, yUlp1, and the SUMO fusions in order to assess the relative activities of fixed amounts of the proteases against the different SUMO tags. In these experiments, fixed amounts of the proteases were incubated for varying amounts of time (15 min. to 4 hrs.) with the six SUMO-eGFP fusions tested. As shown in FIG. 4B, hSENP2 was again a considerably more active protease than yUlp1 against the hSUMO-3-eGFP protein, providing nearly complete cleavage within 2 hrs., while yUlp1 was able to cleave apparently less than half of the substrate in 4 hrs., consistent with the approximate 4-fold advantage of hSENP2 in the dilution series in FIG. 4A. With the other SUMO fusions, in general yUlp1 performed somewhat better in the time course experiments than in the dilution series, cleaving not only T-SUMO but also AtSUMO1 and AtSUMO2 significantly better than did hSENP2. In addition, the proteases has similar activity to each other against hSUMO-1 and ySmt3, with both enzymes cleaving hSUMO-1-eGFP poorly and ySmt3-eGFP well.

Overall, the experiments in FIG. 4 demonstrate that human SENP2 and yeast Ulp1 have different levels of activity and robustness on SUMO tags from a variety of species, and these non-obvious specificities have been revealed in these studies. A major finding of these two sets of experiments is that hSENP2 is a much stronger protease than yUlp1 against a human SUMO-3 fusion, while yUlp1 had some advantages in the cleavage of certain plant SUMO's. The fact that hSENP2 is able to effectively cleave hSUMO-3, which was shown to be a superior expression tag (FIG. 3), gives rise to the inventive subject matter of using hSUMO-3 and hSENP2 as an effective SUMO/protease pair for an expression system offering improvement over previously described ySmt3/yUlp1 systems. In addition, hSENP2 also cleaved ySmt3 fusion as well as (FIG. 4B) or better than (FIG. 4A) did yUlp1 itself, leading to the concept that hSENP2 could alternatively be employed in an expression system using yeast Smt3—i.e. a system featuring the pairing of tag and protease from different species.

Example 9

Additional Diverse SUMO Proteases have Different Levels of Activity and Preferences for Certain SUMO Proteins In Vitro The design and construction of all the pET vectors expressing four additional SUMO protease catalytic domains has been described above. The DNA sequences and translation frames of hSENP1, hSENP6, AtULP1c, and GST-XopD are shown in FIGS. 12-13. These proteases and each of the six SUMO-eGFP fusions described above were expressed in *E. coli* and purified on nickel columns by way of the 6xHis tags on the C-termini (proteases) or N-termini (SUMO-eGFP's) of the proteins. In vitro reactions were performed in which each purified protease was used in reactions with each of the purified SUMO-eGFP proteins, and the cleavage results were analyzed by Coomassie-stained SDS-PAGE gels (FIG. 5). Since the hSENP1, hSENP6, AtULP1c, and XopD protease catalytic domains displayed considerably less overall activity in vitro than those of hSENP2 and yUlp1, these 4 enzymes were tested at single concentrations with fixed incubation times, and were therefore not analyzed in as great detail as the proteases in FIG. 4, where enzyme amounts and incubation times were varied.

As shown in FIG. 5, different enzymes had different specificities against the various SUMO-eGFP fusion proteins. The most active of the proteases in FIG. 5 was hSENP1, which cleaved ySmt3 the best, followed by hSUMO-3. It also cleaved the other 4 fusions, but to a much lesser extent. Less active but seemingly more specific was hSENP6, which demonstrated partial cleavage of hSUMO-3-eGFP but did not digest the others at the incubation time and enzyme concentration used; interestingly, this protease had previously been claimed as an hSUMO-1-specific protease (Kim, K. I., S. H. Baek, Y. J. Jeon, S. Nishimori, T. Suzuki, S. Uchida, N.

Shimbara, H. Saitoh, K. Tanaka, and C. H. Chung, 2000, A new SUMO-1-specific protease, SUSP1, that is highly expressed in reproductive organs, J Biol Chem 275:14102-6) based on its ability to cleave β-galactosidase fusions of hSUMO-1 but not ySmt3, but those experiments did not test hSUMO-3. Another enzyme with particular SUMO specificities is XopD, derived from a prokaryotic plant pathogen, *Xanthomonas*. It carried out partial cleavage of the three plant SUMO fusions (AtSUMO1, AtSUMO2, and T-SUMO), but did not cleave the fusions with yeast or human SUMO's. This is possibly consistent with the role of the pathogen in plant systems and demonstrates that despite the high level of sequence conservation among SUMO proteins and among SUMO proteases, there is evidence for certain SUMO tag/protease pairs having specificity for each other within and between species. Finally, AtULP1c did not show activity against any of the SUMO fusions. Although one possibility is that inactive enzyme was produced, it should be noted that at least 13 putative SUMO proteases and at least 8 putative SUMO proteins have been identified in *Arabidopsis*, so another possibility is that AtSUMO1 and AtSUMO2 are the natural substrates for a different AtULP, and perhaps AtULP1c might be active against one of the other AtSUMO proteins, which have not yet been cloned and expressed.

The fact that different SUMO proteases from diverse species have varying levels of robustness and different and sometimes unexpected specificities for particular SUMO proteins points to the idea that multiple SUMO proteins and proteases must be investigated from a variety of species in order to maximize the effectiveness of overexpression proteins of interest and efficient generation of desired N-termini for them. Although in this inventive subject matter Applicants have already identified in hSUMO-3 and hSENP2 a SUMO tag/protease pair that gives substantial expression-system improvement over the previous state-of-the-art system, ySmt3/yUlp1, Applicants are also exploring the SUMO tags and proteases of multiple species by cloning and expressing them and testing them against one another. Examples of SUMO proteins and proteases Applicants are pursuing are provided in FIG. 1 and Table 3.

Example 10

Examples of Various Classes of Proteins Whose Fusion with SUMO Proteins Will Improve Quantity and Quality of Proteins The design and construction of all the pET vectors expressing eGFP has been described above. As with eGFP, any DNA sequence can be cloned as a fusion with 6xHis-SUMO, such as 6xHis-hSUMO-3. Furthermore, the 6xHis-SUMO-protein of interest fusion protein can be recloned into any yeast, such as Yep, baculoviral, such as pFastBac, mammalian, such as pcDNA3, or other host vectors by, for example, a simple cut-and-paste procedure identical or similar to the one described above. Cell propagation, protein expression, harvesting, lysis, and purification of fusion are performed described above or according to one of the established procedures described elsewhere. Cleavage of fusions with an appropriate SUMO protease (such as hSENP2) can be performed as described above. The system described in this application has significant advantages as compared to other systems currently in use. One or more of these advantages may create a precedent for preferred use of the system described here over other systems. Industrial needs for protein manufacturing may suggest that the following classes or groups of proteins may be exemplified as the ones most likely to benefit from use of the current inventive subject matter. Two of the factors that may be considered when an expression system is selected are 1) the success of expression of the protein in various systems and 2) requirement for specific N-terminus. Each of these factors can be successfully addressed by the system described herein: 1) SUMO proteins such as hSUMO-3 enhance the production of proteins, and 2) robust cleavage by SUMO proteases such as hSENP2 allows generation of almost any amino-terminus. Table 3 provides representative molecules and GenBank Accession numbers for the expression of the proteins produced using the methods of the inventive subject matter.

Example 11

Comparison of Enzyme Kinetics of hSENP2 and yUlp1

To further compare the catalytic activities of hSENP2 and yUlp1, Applicants analyzed their kinetics. The kinetic parameters ($K_m$ and $K_{cat}$) for both SUMO proteases were determined using yeast and human SUMO-GFP fusions. Briefly, the SUMO proteases were assayed by mixing 6 µM enzyme with different amounts of the substrate (either the ySmt3-eGFP or the hSUMO-3-eGFP, at 12, 6, 3, 1.5, 0.75, and 0.375 mM) in PBS (pH 7.5) containing 1.0 mM DTT. Our initial experiments for time course concluded that 1 hour was well within the initial velocity rates for both SUMO proteases, in that the rates of the reactions were within in the linear region. The reactions were incubated at 30 C for 1 hour and stopped by addition of SDS-PAGE loading buffer. Samples were then heated at 95 C for 3 min and loaded onto a 15% SDS-polyacrylamide gel for analysis. The SDS-polyacrylamide gels were stained with Coomassie Blue and scanned such that each band could be quantified using the software, Scion Image version Beta 4.0.2 (Scion Corporation). Densitometry analyses were performed to determine the amount of product generated per unit time, as compared with a loaded albumin (standard as known amount). The initial velocity values used for curve fitting were the mean of three independent experiments. These initial velocity measurements were plotted against the substrate concentrations and fit to the Michaelis-Menten equation using KaleidaGraph 3.5 (Synergy Corporation). The $K_{cat}$ values were calculated by assuming 100% activity for the enzyme.

Representative kinetic parameters for hSENP2 and yUlp1 are presented in Table 1, utilizing methionine at the interface of the fusion protein. Interestingly, although ySmt3 is the natural substrate for yUlp1, hSENP2 has a somewhat higher affinity and faster catalytic rate (about 2-fold difference in $K_{cat}$) for cleavage of ySmt3-eGFP than does yUlp1. But strikingly, hSENP2 has a much higher affinity and faster catalytic rate for hSUMO-3-eGFP than does yUlp1 (about 12-fold difference in $K_{cat}$). These data illustrate in a quantitative manner that hSENP2 is a much more active SUMO protease enzyme than yUlp1 on the effective expression tag hSUMO-3.

TABLE 1

Kinetic parameters ($K_m$ and $K_{cat}$) for hSENP2 and yUlp1

|  | hSENP2 | yUlp1 |
| --- | --- | --- |
| hSUMO-3-eGFP | $K_m$ = 2.41 mM<br>$K_{cat}$ = 0.33 mM$^{-1}$S$^{-1}$ | $K_m$ = 15.8 mM<br>$K_{cat}$ = 0.027 mM$^{-1}$S$^{-1}$ |

TABLE 1-continued

Kinetic parameters ($K_m$ and $K_{cat}$) for hSENP2 and yUlp1

|  | hSENP2 | yUlp1 |
|---|---|---|
| ySmt3-eGFP | $K_m$ = 2.72 mM<br>$K_{cat}$ = 0.75 mM$^{-1}$S$^{-1}$ | $K_m$ = 4.5 mM<br>$K_{cat}$ = 0.40 mM$^{-1}$S$^{-1}$ |

Example 12

Comparison of hSENP2 and yUlp1 on Cleavage of hSUMO-3-eGFP Fusions with Different Amino Acid Termini To determine if hSENP2 can cleave hSUMO-3-eGFP fusions with each of the 20 amino acids at the N-terminus of eGFP and to determine if it is more powerful than yUlp1, we have designed and made a set of hSUMO-3-X-eGFP fusions in which the methionine (M) that follows the C-terminal Gly-Gly motif of the hSUMO-3 has been replaced with one of the other 19 amino acids (X).

The purified hSUMO-3-X-eGFP fusions were incubated with either hSENP2 or yUlp1 in PBS (pH 7.4) containing 2 mM DTT at 30 C for 1 hour. Cleavage of the fusions was determined by quantitative comparison of the released proteins (eGFP and hSUMO-3) with the fusions observed on 15% SDS-polyacrylamide gels. Briefly, after the proteins were separated on the gels and stained with Coomassie Blue, the gels were scanned and saved as TIFF images. The protein bands were quantitated using the Scion Image (version Beta 4.0.2) (Scion Corporation, Bethesda, Md.) by densitometric analyses. The values of pixels (in arbitrary units) for each protein band (hSUMO-3-eGFP fusion, released eGFP and hSUMO-3) were recorded. Percentages of cleavage were determined by the ratio of the densities of the released eGFP and hSUMO-3 divided by the total densities (hSUMO-3-eGFP plus released proteins).

The results for cleavage of all versions of hSUMO-3-X-eGFP (with different amino acids at the eGFP N-terminus) by hSENP2 and yUlp1 are shown in Table 2 and FIG. 4C. Both hSENP2 and yUlp1 can partially or totally cleave hSUMO-3-X-eGFP for 19 of the amino acids, but the enzymes cannot effectively cleave the fusion where proline is at the N-terminus of eGFP. Compared to yUlp1, hSENP2 has much higher efficiency of cleavage (at least 5-10-fold higher in most cases) for all the 19 amino acid junctions. When a low amount of SENP2 was used (1:1000 ratio of enzyme to substrate), 14 amino acid junctions were >90% cleaved while five others (D, I, L, Q, and T) were at least >50% cleaved. In contrast, with the same amount of yUlp1 used, the enzyme gave only 10-27% cleavage for most of the amino acid junctions, and for the six other fusions (D, I, K, L, Q and V) only 0-4% cleavage was achieved. At a 1:100 ratio of enzyme to substrate SENP2 gave >95% cleavage for all the amino acid junctions except the proline fusion, but yUlp1 still poorly cleaves the I, K, L, and V fusions in that only ~2-22% cleavage was observed. Overall, the data demonstrate that hSENP2, unlike Ulp1, is an effective enzyme for cleavage of any amino acid (except proline) fused to hSUMO-3.

TABLE 2

Percent cleavage of hSUMO-3-eGFP fusions by hSENP2 and yUlp1

|  | Control | A[1] | C | D | E | F | G | H | I | K | L |
|---|---|---|---|---|---|---|---|---|---|---|---|
| hSENP2[2] (1:1000) | 0 | 92.5 | 98.5 | 69.8 | 92.2 | 98.9 | 98.9 | 98.4 | 56.2 | 92.8 | 75.2 |
| hSENP2 (1:100) | 0 | 99.6 | 100 | 99.5 | 100 | 100 | 100 | 100 | 98.4 | 100 | 98.6 |
| yUlp1 (1:1000) | 0 | 27.1 | 25.3 | 3.3 | 11.3 | 27.0 | 27.0 | 25.5 | 0 | 0 | 0 |
| yUlp1 (1:100) | 0 | 96.3 | 98.4 | 92.3 | 80.1 | 95.4 | 96.5 | 90.8 | 1.9 | 22.4 | 4.4 |

|  | M | N | P | Q | R | S | T | V | W | Y |
|---|---|---|---|---|---|---|---|---|---|---|
| hSENP2[2] (1:1000) | 95.4 | 98.3 | 0 | 66.7 | 98.7 | 99.1 | 82.0 | 99.8 | 99.4 | 98.7 |
| hSENP2 (1:100) | 99.4 | 96.2 | 0 | 95.9 | 99.7 | 99.6 | 99.0 | 100 | 100 | 100 |
| yUlp1 (1:1000) | 18.4 | 16.9 | 0 | 3.7 | 17.2 | 16.7 | 14.3 | 4.0 | 16.8 | 16.9 |
| yUlp1 (1:100) | 98.3 | 97.9 | 0 | 65.5 | 96.6 | 98.2 | 95.8 | 20.2 | 89.7 | 96.9 |

Control is hSUMO-3-M-eGFP treated with the same conditions, but with no enzyme added.
[1]The letters are the one-letter code indicating the amino acid that is present at the N-terminus of eGFP, fused with hSUMO-3.
[2]Ratio of enzyme to substrate is indicated in parentheses

TABLE 3

Summary of representative SUMO proteases

| SUMO protease | Species | Reference or accession number |
|---|---|---|
| yUlp1 | Saccharomyces cerevisiae | Li 1999, Malakhov |
| yUlp2 | Saccharomyces cerevisiae | Li 2000 |
| hSENP1 | Homo sapiens | Gong, Xu |
| hSENP2 | Homo sapiens | Nishida 2001, Zhang, Reverter |
| hSENP3 | Homo sapiens | Nishida 2000 |
| hSENP5 | Homo sapiens | Q96HI0 |
| hSENP6 | Homo sapiens | Kim |
| hSENP7 | Homo sapiens | Q9BQF6 |
| AtULP1a, b, c, d | Arabidopsis thalania | Kurepa |
| AtULP2a, b, c, d, e, f, g, h | Arabidopsis thalania | Kurepa |
| AtESD4 | Arabidopsis thalania | Murtas |
| XopD | Xanthomonas campestris | Hotson |
| XSENP1a, b | Xenopus laevis | Yukita |
| DmUlp1 | Drosophila melanogaster | Smith |
| CeULP-1 | Caenorhabditis elegans | AAK21468 |

TABLE 3-continued

Summary of representative SUMO proteases

| SUMO protease | Species | Reference or accession number |
|---|---|---|
| CeULP-2 | Caenorhabditis elegans | AAA98019 |
| SpUlp1 | Schizosaccharomyces pombe | Taylor |
| SpUlp2 | Schizosaccharomyces pombe | O13769 |
| KlUlp1 | Kluyveromyces lactis | CAG98289 |
| PfUlp | Plasmodium falciparum | AAN36413 |
| AnUlp | Aspergillus nidulans | EAA63091 |

Indicated are references for studies in which a given SUMO protease was identified and/or characterized; protein database accession numbers are given for putative SUMO proteases lacking published data.

TABLE 4

Summary of activity levels of SUMO protease catalytic domains on various SUMO fusions

| | hSUMO1-eGFP | hSUMO3-eGFP | AtSUMO1-eGFP | AtSUMO2-eGFP | T-SUMO-eGFP | ySmt3-eGFP |
|---|---|---|---|---|---|---|
| hSENP2 | ++ | +++ | + | + | + | +++++ |
| yULP1 | + | + | ++ | ++ | ++ | ++++ |
| hSENP1 | +/− | + | +/− | +/− | +/− | ++ |
| hSENP6 | − | +/− | − | − | − | − |
| AtULP1c | − | − | − | − | − | − |
| XopD | − | − | − | +/− | +/− | +/− |

TABLE 5

Examples of Proteins and Protein Classes for use with the Current Inventive Subject Matter

| Protein class | Success rate with conventional systems | Protein | Requirement for specific N-termini | ACC # |
|---|---|---|---|---|
| Cytokine | High/inclusion bodies | IL-15 IFN☐ | Yes | P40933 P01579 P01375 |
| Chemokine | High/inclusion bodies | Myb-1☐ | Yes | P13236 |
| Growth factors | low | TGF☐ | Yes | P01135 |
| Enzymes | Low | DNA polymerase | Yes | 1RDR |
| | Very low | DNase II alpha | Yes | AAC77366 |
| | Very low | Cathepsin (peptidase) | Unknown | P07858 |
| | Very low | BMP-1 protease | Unknown | NP_001190 |
| Peptides including therapeutic | Low/proteolysis | Calcitonin | Yes | CAA26189 |
| Nuclear receptors | high | LXR | No | Q13133 |
| Cytokine/chemokine/ growth factor receptors | Low/inclusion bodies | IFNAR, VEGFR, CCR9 | No | P15260 P35968 NP_034043 P00533 |
| Ser-Thr kinases | Low | MAPK | No | P49137 |
| Tyr kinases | Extremely low/ inactive | Zap 70 | No | P43403 |
| Transcription factors | low | CREB | Unknown | NP_005185 |
| Initiation factors | low | eIF2 | Unknown | NP_004085 |
| Viral/parasite/bacterial proteins (vaccines) | Low | Spike protein, Apa (Rv1860), RAP-1 | Varies | AAP33697 Q50906 AAF15365 |

REFERENCE LIST

The following references are cited to provide the reader with background information relating to the inventive subject matter and the general state of the art. The fact that a document is cited herein is not an indication that Applicants believe that any document is prior art or is material to patentability. Each of the following documents is incorporated by reference in the Specification of this application as though set forth in full herein.

1. Bayer, P., A. Arndt, S. Metzger, R. Mahajan, F. Melchior, R. Jaenicke, and J. Becker, 1998, Structure determination of the small ubiquitin-related modifier SUMO-1, J Mol Biol 280:275-86.
2. Ben-Bassat, A, 1991, Methods for removing N-terminal methionine from recombinant proteins, Bioprocess Technol 12:147-59.
3. Buchberger, A., M. J. Howard, M. Proctor, and M. Bycroft, 2001, The UBX domain: a widespread ubiquitin-like module, J Mol Biol 307:17-24.
4. Butt, T. R., S. Jonnalagadda, B. P. Monia, E. J. Sternberg, J. A. Marsh, J. M. Stadel, D. J. Ecker, and S. T. Crooke, 1989, Ubiquitin fusion augments the yield of cloned gene products in Escherichia coli, Proc Natl Acad Sci USA 86:2540-4.
5. Davis, G. D., C. Elisee, D. M. Newham, and R. G. Harrison, 1999, New fusion protein systems designed to give soluble expression in Escherichia coli, Biotechnol Bioeng 65:382-8.
6. di Guan, C., P. Li, P. D. Riggs, and H. Inouye, 1988, Vectors that facilitate the expression and purification of foreign peptides in Escherichia coli by fusion to maltose-binding protein, Gene 67:21-30.
7. Ecker, D. J., J. M. Stadel, T. R. Butt, J. A. Marsh, B. P. Monia, D. A. Powers, J. A. Gorman, P. E. Clark, F. Warren, A. Shatzman, and et al., 1989, Increasing gene expression in yeast by fusion to ubiquitin, J Biol Chem 264:7715-9.
8. Georgiou, G. and P. Valax, Isolating inclusion bodies from bacteria, 1999, Methods Enzymol 309:48-58.
9. Goettsch, S., and P. Bayer, 2002, Structural attributes in the conjugation of ubiquitin, SUMO and RUB to protein substrates, Front Biosci 7:a148-62.
10. Hanania, U., N. Furman-Matarasso, M. Ron, and A. Avni, 1999, Isolation of a novel SUMO protein from tomato that suppresses EIX-induced cell death, Plant J 19:533-41.
11. Hotson, A., R. Chosed, H. Shu, K. Orth, and M. B. Mudgett, 2003, Xanthomonas type III effector XopD targets SUMO-conjugated proteins in plants, Mol Microbiol 50:377-89.
12. Hu, M., P. Li, M. Li, W. Li, T. Yao, J. W. Wu, W. Gu, R. E. Cohen, and Y. Shi, 2002, Crystal structure of a UBP-family deubiquitinating enzyme in isolation and in complex with ubiquitin aldehyde, Cell 111:1041-54.
13. Ikonomou, L., Y. J. Schneider, and S. N. Agathos, 2003, Insect cell culture for industrial production of recombinant proteins, Appl Microbiol Biotechnol 62:1-20.
14. Jentsch, S., and G. Pyrowolakis, 2000, Ubiquitin and its kin: how close are the family ties? Trends Cell Biol 10:335-42.
15. Johnson, E. S., 2004, Protein modification by SUMO, Annu Rev Biochem 73:355-82.
16. Johnson, E. S., I. Schwienhorst, R. J. Dohmen, and G. Blobel, 1997, The ubiquitin-like protein Smt3p is activated for conjugation to other proteins by an Aos1p/Uba2p heterodimer, Embo J 16:5509-19.
17. Jonasson, P., S. Liljeqvist, P. A. Nygren, and S. Stahl, 2002, Genetic design for facilitated production and recovery of recombinant proteins in Escherichia coli, Biotechnol Appl Biochem 35:91-105.
18. Kapust, R. B., and D. S. Waugh, 1999, Escherichia coli maltose-binding protein is uncommonly effective at promoting the solubility of polypeptides to which it is fused, Protein Sci 8:1668-74.
19. Kim, K. I., S. H. Baek, and C. H. Chung, 2002, Versatile protein tag, SUMO: its enzymology and biological function, J Cell Physiol 191:257-68.
20. Kim, K. I., S. H. Baek, Y. J. Jeon, S. Nishimori, T. Suzuki, S. Uchida, N. Shimbara, H. Saitoh, K. Tanaka, and C. H. Chung, 2000, A new SUMO-1-specific protease, SUSP1, that is highly expressed in reproductive organs, J Biol Chem 275:14102-6.
21. Kretz-Remy, C., and R. M. Tanguay, 1999, SUMO/sentrin: protein modifiers regulating important cellular functions, Biochem Cell Biol 77:299-309.
22. Kurepa, J., J. M. Walker, J. Smalle, M. M. Gosink, S. J. Davis, T. L. Durham, D. Y. Sung, and R. D. Vierstra, 2003, The small ubiquitin-like modifier (SUMO) protein modification system in Arabidopsis, Accumulation of SUMO1 and -2 conjugates is increased by stress. J Biol Chem 278:6862-72.
23. Larsen, C. N., and H. Wang, 2002, The ubiquitin superfamily: members, features, and phylogenies, J Proteome Res 1:411-9.
24. Layfield, R., K. Franklin, M. Landon, G. Walker, P. Wang, R. Ramage, A. Brown, S. Love, K. Urquhart, T. Muir, R. Baker, and R. J. Mayer, 1999, Chemically synthesized ubiquitin extension proteins detect distinct catalytic capacities of deubiquitinating enzymes, Anal Biochem 274:40-9.
25. Li, S. J., and M. Hochstrasser, 1999, A new protease required for cell-cycle progression in yeast, Nature 398:246-51.
26. Li, S. and M. Hochstrasser, 2000, The yeast ULP2 (SMT4) gene encodes a novel protease specific for the ubiquitin-like Smt3 protein, Mol Cell Biol 20:2367-77.
27. Link, A. J., K. Robison, and G. M. Church, 1997, Comparing the predicted and observed properties of proteins encoded in the genome of Escherichia coli K-12, Electrophoresis 18:1259-313.
28. Lo Conte, L., B. Ailey, T. J. Hubbard, S. E. Brenner, A. G. Murzin, and C. Chothia, 2000, SCOP: a structural classification of proteins database, Nucleic Acids Res 28:257-9.
29. Lois, L. M., C. D. Lima, and N. H. Chua, 2003, Small ubiquitin-like modifier modulates abscisic acid signaling in Arabidopsis, Plant Cell 15:1347-59.
30. Malakhov, M. P., O. A. Malakhova, K. I. Kim, K. J. Ritchie, and D. E. Zhang, 2002, UBP43 (USP18) Specifically Removes ISG15 from Conjugated Proteins, J Biol Chem 277:9976-81.
31. Malakhov, M. P., Mattern, M. R., Malakhova, O. A., Drinker, M., Weeks, S. D., and Butt, T. R., 2004, SUMO fusions and SUMO-specific protease for efficient expression and purification of proteins, J Structural and Functional Genomics 5:75-86.
32. Melchior, F., M. Schergaut, and A. Pichler, 2003, SUMO: ligases, isopeptidases and nuclear pores, Trends Biochem Sci 28:612-8.
33. Mossessova, E., and C. D. Lima, 2000, Ulp1-SUMO crystal structure and genetic analysis reveal conserved interactions and a regulatory element essential for cell growth in yeast, Mol Cell 5:865-76.
34. Muller, S., C. Hoege, G. Pyrowolakis, and S. Jentsch, 2001, SUMO, ubiquitin's mysterious cousin, Nat Rev Mol Cell Biol 2:202-10.

35. Murtas, G., P. H. Reeves, Y. F. Fu, I. Bancroft, C. Dean, and G. Coupland, 2003, A nuclear protease required for flowering-time regulation in *Arabidopsis* reduces the abundance of SMALL UBIQUITIN-RELATED MODIFIER conjugates, Plant Cell 15:2308-19.

36. Ryan, T. E., and S. D. Patterson, 2002, Proteomics: drug target discovery on an industrial scale, Trends Biotechnol 20:S45-51.

37. Saitoh, H., and J. Hinchey, 2000, Functional heterogeneity of small ubiquitin-related protein modifiers SUMO-1 versus SUMO-2/3, J Biol Chem 275:6252-8.

38. Sambrook, J., E. F. Fritsch, and T. Maniatis, 1989, Molecular Cloning: A Laboratory Manual, Second Edition, Cold Spring Harbor Laboratory, Cold Spring Harbor, N.Y.

39. Smith, D. B., and K. S. Johnson, 1988, Single-step purification of polypeptides expressed in *Escherichia coli* as fusions with glutathione S-transferase, Gene 67:31-40.

40. Terpe, K., 2003, Overview of tag protein fusions: from molecular and biochemical fundamentals to commercial systems, Appl Microbiol Biotechnol 60:523-33.

41. Varshavsky, A., 2003, The N-end rule and regulation of apoptosis, Nat Cell Biol 5:373-6.

42. Varshavsky, A., 1996, The N-end rule: functions, mysteries, uses, Proc Natl Acad Sci USA 93:12142-9.

43. Waldo, G. S., B. M. Standish, J. Berendzen, and T. C. Terwilliger, 1999, Rapid protein-folding assay using green fluorescent protein, Nat Biotechnol 17:691-5.

44. Weickert, M. J., D. H. Doherty, E. A. Best, and P. O. Olins, 1996, Optimization of heterologous protein production in *Escherichia coli*, Curr Opin Biotechnol 7:494-9.

45. Yeh, E. T., L. Gong, and T. Kamitani, 2000, Ubiquitin-like proteins: new wines in new bottles, Gene 248:1-14.

46. Zhang, G., V. Gurtu, and S. R. Kain, 1996, An enhanced green fluorescent protein allows sensitive detection of gene transfer in mammalian cells, Biochem Biophys Res Commun 227:707-11.

47. Gong, L., Millas, S., Maul, G. G., and E. T. H. Yeh, 2000, Differential regulation of sentrinized proteins by a novel sentrin-specific protease, J. Biol. Chem. 275:3355-3359.

48. Xu, Z., and S. W. Au, 2005, Mapping residues of SUMO precursors essential in differential maturation by SUMO-specific protease, SENP1, Biochem. J., in press.

49. Nishida, T., Kaneko, F., Kitagawa, M., and H. Yasuda H, 2001, Characterization of a novel mammalian SUMO-1/Smt3-specific isopeptidase, a homologue of rat axam, which is an axin-binding protein promoting beta-catenin degradation, J. Biol. Chem. 276:39060-39066.

50. Reverter, D., and C. D. Lima CD, 2004, A basis for SUMO protease specificity provided by analysis of human Senp2 and a Senp2-SUMO complex, Structure (Camb.) 12:1519-1531.

51. Nishida, T., Tanaka, H., and H. Yasuda, 2000, A novel mammalian Smt3-specific isopeptidase 1 (SMT3IP1) localized in the nucleolus at interphase, Eur. J. Biochem. 267:6423-6427.

52. Yukita, A., Michiue, T., Fukui, A., Sakurai, K., Yamamoto, H., Ihara, M., Kikuchi, A., and M. Asashima, 2004, XSENP1, a novel sumo-specific protease in *Xenopus*, inhibits normal head formation by down-regulation of Wnt/beta-catenin signalling, Genes Cells 9:723-736.

53. Smith, M., Bhaskar, V., Fernandez, J., and A. J. Courey, 2004, *Drosophila* Ulp1, a nuclear pore-associated SUMO protease, prevents accumulation of cytoplasmic SUMO conjugates, J. Biol. Chem. 279:43805-43814.

54. Taylor, D. L., Ho, J. C., Oliver, A., and F. Z. Watts, 2002, Cell-cycle-dependent localisation of Ulp1, a *Schizosaccharomyces pombe* Pmt3 (SUMO)-specific protease, J. Cell Sci. 115:1113-1122.

55. Marblestone, J. Edavettal, S., Lim, Y., Lim, P., Zuo, X., Butt, T. R. (2006) Comparison of SUMO Fusion Technology with Traditional Gene Fusion System: Effects of Recombinant Protein Expression and Purification. Protein Science 15(1):182-9.

56. Butt, T. R., Edavettal S., Hall, J. and Mattern M. R (2005) SUMO Fusion Technology for Difficult to Express Proteins. Protein Expr. Purif. 43:1-9.

57. Zuo, Xun., Mattern, M. R., Tan, R., Li, S., Hall, H., Sterner, D. E., Shoo, J., Lim, P., Sarafianos, S. G., Kazi, L., Navas-Martin., Weiss, S. R. and Butt, T. R. (2005) Expression and Purification of SARS Coronavirus Proteins Using SUMO-Fusions. Protein Expr. Purif. 42:100-110.

58. Zuo, Xun, Li, Shuisen, Hall John, Mattern, Michael R., Tran, Tran, Shoo, Joshua, Tan, Robin, Weiss, Susan and Butt, T. R. (2005) Enhanced expression and purification of membrane proteins by SUMO fusion in *Echerichia coli*. J. Struct. Funct. Genomics 6(2-3):103-11.

The inventive subject matter being thus described, it will be obvious that the same may be modified or varied in many ways. Such modifications and variations are not to be regarded as a departure from the spirit and scope of the invention and all such modifications and variations are intended to be included within the scope of the following claims.

---

SEQUENCE LISTING

```
<160> NUMBER OF SEQ ID NOS: 113

<210> SEQ ID NO 1
<211> LENGTH: 97
<212> TYPE: PRT
<213> ORGANISM: Homo sapiens

<400> SEQUENCE: 1

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45
```

```
Glu Ser Tyr Cys Gln Arg Gln Gly Val Pro Met Asn Ser Leu Arg Phe
            50                  55                  60

Leu Phe Glu Gly Gln Arg Ile Ala Asp Asn His Thr Pro Lys Glu Leu
 65                 70                  75                  80

Gly Met Glu Glu Glu Asp Val Ile Glu Val Tyr Gln Glu Gln Thr Gly
                85                  90                  95

Gly

<210> SEQ ID NO 2
<211> LENGTH: 291
<212> TYPE: DNA
<213> ORGANISM: Homo sapiens

<400> SEQUENCE: 2
atgtctgacc aggaggcaaa accttcaact gaggacttgg gggataagaa ggaaggtgaa      60
tatattaaac tcaaagtcat tggacaggat agcagtgaga ttcacttcaa agtgaaaatg     120
acaacacatc tcaagaaact caaagaatca tactgtcaaa gacagggtgt tccaatgaat     180
tcactcaggt ttctctttga gggtcagaga attgctgata tcatactcc aaaagaactg      240 ggaatggagg aagaagatgt gattgaagtt tatcaggaac aaacgggggg t              291

<210> SEQ ID NO 3
<211> LENGTH: 92
<212> TYPE: PRT
<213> ORGANISM: Homo sapiens

<400> SEQUENCE: 3

Met Ser Glu Glu Lys Pro Lys Glu Gly Val Lys Thr Glu Asn Asp His
  1               5                  10                  15

Ile Asn Leu Lys Val Ala Gly Gln Asp Gly Ser Val Val Gln Phe Lys
                20                  25                  30

Ile Lys Arg His Thr Pro Leu Ser Lys Leu Met Lys Ala Tyr Cys Glu
            35                  40                  45

Arg Gln Gly Leu Ser Met Arg Gln Ile Arg Phe Arg Phe Asp Gly Gln
        50                  55                  60

Pro Ile Asn Glu Thr Asp Thr Pro Ala Gln Leu Glu Met Glu Asp Glu
 65                 70                  75                  80

Asp Thr Ile Asp Val Phe Gln Gln Gln Thr Gly Gly
                85                  90

<210> SEQ ID NO 4
<211> LENGTH: 276
<212> TYPE: DNA
<213> ORGANISM: Homo sapiens

<400> SEQUENCE: 4
atgtccgagg agaagcccaa ggagggtgtg aagacagaga tgaccacat caacctgaag        60 gtggccgggc aggacggctc cgtggtgcag ttcaagatca gaggcacac gccgctgagc      120 aagctgatga ggcctactg cgagaggcag ggcttgtcaa tgaggcagat cagattcagg      180
ttcgacgggc agccaatcaa tgaaactgac actccagcac agctggagat ggaggacgag     240
gacaccatcg acgtgttcca gcagcagacg ggaggt                               276

<210> SEQ ID NO 5
<211> LENGTH: 93
<212> TYPE: PRT
<213> ORGANISM: Arabidopsis thaliana
```

<400> SEQUENCE: 5

Met Ser Ala Asn Gln Glu Glu Asp Lys Lys Pro Gly Asp Gly Gly Ala
1               5                   10                  15

His Ile Asn Leu Lys Val Lys Gly Gln Asp Gly Asn Glu Val Phe Phe
            20                  25                  30

Arg Ile Lys Arg Ser Thr Gln Leu Lys Lys Leu Met Asn Ala Tyr Cys
        35                  40                  45

Asp Arg Gln Ser Val Asp Met Asn Ser Ile Ala Phe Leu Phe Asp Gly
    50                  55                  60

Arg Arg Leu Arg Ala Glu Gln Thr Pro Asp Glu Leu Asp Met Glu Asp
65                  70                  75                  80

Gly Asp Glu Ile Asp Ala Met Leu His Gln Thr Gly Gly
                85                  90

<210> SEQ ID NO 6
<211> LENGTH: 279
<212> TYPE: DNA
<213> ORGANISM: Arabidopsis thaliana

<400> SEQUENCE: 6
atgtctgcaa accaggagga agacaagaag ccaggagacg gaggagctca catcaatctc      60
aaagtcaagg acaggatgg aaacgaggtt tcctttagga tcaagagaag cactcagctc     120
aagaagctga tgaatgctta ctgtgaccgg caatctgtgg acatgaactc cattgctttc     180
ttgtttgatg gcgtcgtcct tcgtgctgag caaactcccg atgagcttga catggaggat     240
ggtgatgaga tcgatgcgat gctccatcag actggtggc                           279

<210> SEQ ID NO 7
<211> LENGTH: 92
<212> TYPE: PRT
<213> ORGANISM: Arabidopsis thaliana

<400> SEQUENCE: 7

Met Ser Ala Thr Pro Glu Glu Asp Lys Lys Pro Asp Gln Gly Ala His
1               5                   10                  15

Ile Asn Leu Lys Val Lys Gly Gln Asp Gly Asn Glu Val Phe Phe Arg
            20                  25                  30

Ile Lys Arg Ser Thr Gln Leu Lys Lys Leu Met Asn Ala Tyr Cys Asp
        35                  40                  45

Arg Gln Ser Val Asp Phe Asn Ser Ile Ala Phe Leu Phe Asp Gly Arg
    50                  55                  60

Arg Leu Arg Ala Glu Gln Thr Pro Asp Glu Leu Glu Met Glu Asp Gly
65                  70                  75                  80

Asp Glu Ile Asp Ala Met Leu His Gln Thr Gly Gly
                85                  90

<210> SEQ ID NO 8
<211> LENGTH: 276
<212> TYPE: DNA
<213> ORGANISM: Arabidopsis thaliana

<400> SEQUENCE: 8
atgtctgcta ctccggaaga agacaagaag cctgaccaag agctcacat caatctcaaa       60 gtcaagggac aggatggtaa tgaagtcttc tttaggatca agagaagcac tcagctcaaa    120
aaactgatga atgcttactg tgaccgtcag tctgtggatt tcaactcaat tgctttcttg    180
tttgatggtc gtcgtcttcg tgccgagcag actccagatg agcttgaaat ggaagatgga    240
gatgagatcg atgcaatgct tcatcagact ggtggt     276

```
<210> SEQ ID NO 9
<211> LENGTH: 96
<212> TYPE: PRT
<213> ORGANISM: Lycopersicum esculentum

<400> SEQUENCE: 9
```

Met Ser Ala Ser Gly Gly Thr Gly Asp Glu Asp Lys Lys Pro Asn Asp
1               5                   10                  15

Gln Met Val His Ile Asn Leu Lys Val Lys Gly Gln Asp Gly Asn Glu
            20                  25                  30

Val Phe Phe Arg Ile Lys Arg Ser Thr Gln Met Arg Lys Leu Met Asn
        35                  40                  45

Ala Tyr Cys Asp Arg Gln Ser Val Asp Met Asn Ser Ile Ala Phe Leu
    50                  55                  60

Phe Asp Gly Arg Arg Leu Arg Ala Glu Gln Thr Pro Asp Glu Leu Glu
65                  70                  75                  80

Met Glu Glu Gly Asp Glu Ile Asp Ala Met Leu His Gln Thr Gly Gly
                85                  90                  95

```
<210> SEQ ID NO 10
<211> LENGTH: 288
<212> TYPE: DNA
<213> ORGANISM: Lycopersicum esculentum

<400> SEQUENCE: 10
```
atgtctgcta gcggcggcac cggagatgaa gataagaagc ctaatgatca gatggttcat      60
atcaatctca aggttaaggg tcaggatggg aatgaagttt ttttcaggat caaacgtagc     120
acacagatgc gcaagctcat gaatgcttat tgtgaccggc agtcagtgga catgaactca     180
attgcattct tatttgatgg cgcaggctt agggcagagc aaactcctga tgagctggag      240
atggaggagg gtgatgaaat cgatgcaatg ctacatcaaa ctggaggc                  288

```
<210> SEQ ID NO 11
<211> LENGTH: 98
<212> TYPE: PRT
<213> ORGANISM: Saccharomyces cerevisiae

<400> SEQUENCE: 11
```

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Ala Pro Glu Asp
65                  70                  75                  80

Leu Asp Met Glu Asp Asn Asp Ile Ile Glu Ala His Arg Glu Gln Ile
                85                  90                  95

Gly Gly

```
<210> SEQ ID NO 12
<211> LENGTH: 294
<212> TYPE: DNA
<213> ORGANISM: Saccharomyces cerevisiae
```

<400> SEQUENCE: 12

```
atgtcggact cagaagtcaa tcaagaagct aagccagagg tcaagccaga agtcaagcct      60
gagactcaca tcaatttaaa ggtgtccgat ggatcttcag agatcttctt caagatcaaa     120
aagaccactc ctttaagaag gctgatggaa gcgttcgcta aaagacaggg taaggaaatg     180
gactccttaa gattcttgta cgacggtatt agaattcaag ctgatcaggc ccctgaagat     240
ttggacatgg aggataacga tattattgag gctcacagag aacagattgg tggt           294
```

<210> SEQ ID NO 13
<211> LENGTH: 104
<212> TYPE: PRT
<213> ORGANISM: Artificial Sequence
<220> FEATURE:
<223> OTHER INFORMATION: Amino acid sequence of N-terminally His-tagged
      human SUMO-1 protein as it is encoded in pET24-6xHis-hSUMO-1

<400> SEQUENCE: 13

```
Met Gly His His His His His His Ser Asp Gln Glu Ala Lys Pro Ser
1               5                   10                  15

Thr Glu Asp Leu Gly Asp Lys Lys Glu Gly Glu Tyr Ile Lys Leu Lys
            20                  25                  30

Val Ile Gly Gln Asp Ser Ser Glu Ile His Phe Lys Val Lys Met Thr
        35                  40                  45

Thr His Leu Lys Lys Leu Lys Glu Ser Tyr Cys Gln Arg Gln Gly Val
    50                  55                  60

Pro Met Asn Ser Leu Arg Phe Leu Phe Glu Gly Gln Arg Ile Ala Asp
65                  70                  75                  80

Asn His Thr Pro Lys Glu Leu Gly Met Glu Glu Glu Asp Val Ile Glu
                85                  90                  95

Val Tyr Gln Glu Gln Thr Gly Gly
            100
```

<210> SEQ ID NO 14
<211> LENGTH: 312
<212> TYPE: DNA
<213> ORGANISM: Artificial Sequence
<220> FEATURE:
<223> OTHER INFORMATION: Nucleotide sequence of N-terminally His-tagged
      human SUMO-1 gene as it appears in pET24-6xHis-hSUMO-1

<400> SEQUENCE: 14

```
atgggtcatc accatcatca tcactctgac caggaggcaa aaccttcaac tgaggacttg      60
ggggataaga aggaaggtga atatattaaa ctcaaagtca ttggacagga tagcagtgag     120
attcacttca aagtgaaaat gacaacacat ctcaagaaac tcaaagaatc atactgtcaa     180
agacagggtg ttccaatgaa ttcactcagg tttctctttg agggtcagag aattgctgat     240
aatcatactc caaaagaact gggaatggag gaagaagatg tgattgaagt ttatcaggaa     300
caaacgggag gt                                                         312
```

<210> SEQ ID NO 15
<211> LENGTH: 101
<212> TYPE: PRT
<213> ORGANISM: Artificial Sequence
<220> FEATURE:
<223> OTHER INFORMATION: Amino acid sequence of N-terminally His-tagged
      human SUMO-3 protein as it is encoded in pET24-6xHis-hSUMO-3

<400> SEQUENCE: 15

```
Met Gly His His His His His His Gly Gly Ser Glu Glu Lys Pro Lys
1               5                   10                  15
```

```
Glu Gly Val Lys Thr Glu Asn Asp His Ile Asn Leu Lys Val Ala Gly
            20                  25                  30

Gln Asp Gly Ser Val Val Gln Phe Lys Ile Lys Arg His Thr Pro Leu
        35                  40                  45

Ser Lys Leu Met Lys Ala Tyr Cys Glu Arg Gln Gly Leu Ser Met Arg
    50                  55                  60

Gln Ile Arg Phe Arg Phe Asp Gly Gln Pro Ile Asn Glu Thr Asp Thr
65                  70                  75                  80

Pro Ala Gln Leu Glu Met Glu Asp Glu Asp Thr Ile Asp Val Phe Gln
                85                  90                  95

Gln Gln Thr Gly Gly
            100
```

```
<210> SEQ ID NO 16
<211> LENGTH: 303
<212> TYPE: DNA
<213> ORGANISM: Artificial Sequence
<220> FEATURE:
<223> OTHER INFORMATION: Nucleotide sequence of N-terminally His-tagged
      human SUMO-3 gene as it appears in pET24-6xHis-hSUMO-3

<400> SEQUENCE: 16
atgggtcatc accatcatca tcacggaggt tccgaggaga agcccaagga gggtgtgaag      60
acagagaatg accacatcaa cctgaaggtg gccgggcagg acggctccgt ggtgcagttc     120
aagatcaaga ggcacacgcc gctgagcaag ctgatgaagg cctactgcga gaggcagggc     180
ttgtcaatga ggcagatcag attcaggttc gacgggcagc caatcaatga aactgacact     240
ccagcacagc tggagatgga ggacgaggac accatcgacg tgttccagca gcagacggga     300
ggt                                                                   303
```

```
<210> SEQ ID NO 17
<211> LENGTH: 102
<212> TYPE: PRT
<213> ORGANISM: Artificial Sequence
<220> FEATURE:
<223> OTHER INFORMATION: Amino acid sequence of N-terminally His-tagged
      Arabidopsis thalania SUMO1 protein as it is encoded in
      pET24-6xHis-AtSUMO1

<400> SEQUENCE: 17

Met Gly His His His His His His Gly Gly Ser Ala Asn Gln Glu Glu
1               5                   10                  15

Asp Lys Lys Pro Gly Asp Gly Gly Ala His Ile Asn Leu Lys Val Lys
            20                  25                  30

Gly Gln Asp Gly Asn Glu Val Phe Phe Arg Ile Lys Arg Ser Thr Gln
        35                  40                  45

Leu Lys Lys Leu Met Asn Ala Tyr Cys Asp Arg Gln Ser Val Asp Met
    50                  55                  60

Asn Ser Ile Ala Phe Leu Phe Asp Gly Arg Arg Leu Arg Ala Glu Gln
65                  70                  75                  80

Thr Pro Asp Glu Leu Asp Met Glu Asp Gly Asp Glu Ile Asp Ala Met
                85                  90                  95

Leu His Gln Thr Gly Gly
            100
```

```
<210> SEQ ID NO 18
<211> LENGTH: 306
<212> TYPE: DNA
<213> ORGANISM: Artificial Sequence
```

<220> FEATURE:
<223> OTHER INFORMATION: Nucleotide sequence of N-terminally His-tagged
      Arabidopsis thalania SUMO1 gene as it appears in
      pET24-6xHis-AtSUMO1

<400> SEQUENCE: 18
atgggtcatc accatcatca tcacggaggt tctgcaaacc aggaggaaga caagaagcca      60
ggagacggag agctcacat caatctcaaa gtcaagggac aggatggaaa cgaggttttc      120
tttaggatca agagaagcac tcagctcaag aagctgatga atgcttactg tgaccggcaa      180
tctgtggaca tgaactccat tgctttcttg tttgatgggc gtcgtcttcg tgctgagcaa      240
actcccgatg agcttgacat ggaggatggt gatgagatcg atgcgatgct ccatcagact      300
ggaggt      306

<210> SEQ ID NO 19
<211> LENGTH: 101
<212> TYPE: PRT
<213> ORGANISM: Artificial Sequence
<220> FEATURE:
<223> OTHER INFORMATION: Amino acid sequence of N-terminally His-tagged
      Arabidopsis thalania SUMO2 protein as it is encoded in
      pET24-6xHis-AtSUMO2

<400> SEQUENCE: 19

Met Gly His His His His His His Gly Gly Ser Ala Thr Pro Glu Glu
1               5                   10                  15

Asp Lys Lys Pro Asp Gln Gly Ala His Ile Asn Leu Lys Val Lys Gly
            20                  25                  30

Gln Asp Gly Asn Glu Val Phe Phe Arg Ile Lys Arg Ser Thr Gln Leu
        35                  40                  45

Lys Lys Leu Met Asn Ala Tyr Cys Asp Arg Gln Ser Val Asp Phe Asn
    50                  55                  60

Ser Ile Ala Phe Leu Phe Asp Gly Arg Arg Leu Arg Ala Glu Gln Thr
65                  70                  75                  80

Pro Asp Glu Leu Glu Met Glu Asp Gly Asp Glu Ile Asp Ala Met Leu
                85                  90                  95

His Gln Thr Gly Gly
            100

<210> SEQ ID NO 20
<211> LENGTH: 303
<212> TYPE: DNA
<213> ORGANISM: Artificial Sequence
<220> FEATURE:
<223> OTHER INFORMATION: Nucleotide sequence of N-terminally His-tagged
      Arabidopsis thalania SUMO2 gene as it appears in
      pET24-6xHis-AtSUMO2

<400> SEQUENCE: 20
atgggtcatc accatcatca tcacggaggt tctgctactc cggaagaaga caagaagcct      60
gaccaaggag ctcacatcaa tctcaaagtc aagggacagg atggtaatga agtcttcttt      120
aggatcaaga gaagcactca gctcaaaaaa ctgatgaatg cttactgtga ccgtcagtct      180
gtggatttca actcaattgc tttcttgttt gatggtcgtc gtcttcgtgc cgagcagact      240
ccagatgagc ttgaaatgga agatggagat gagatcgatg caatgcttca tcagactgga      300
ggt      303

<210> SEQ ID NO 21
<211> LENGTH: 105
<212> TYPE: PRT

<213> ORGANISM: Artificial Sequence
<220> FEATURE:
<223> OTHER INFORMATION: Amino acid sequence of N-terminally His-tagged tomato (Lycopersicum esculentum) T-SUMO protein as it is encoded in pET24-6xHis-T-SUMO

<400> SEQUENCE: 21

Met Gly His His His His His His Gly Gly Ser Ala Ser Gly Gly Thr
1               5                   10                  15

Gly Asp Glu Asp Lys Lys Pro Asn Asp Gln Met Val His Ile Asn Leu
            20                  25                  30

Lys Val Lys Gly Gln Asp Gly Asn Glu Val Phe Phe Arg Ile Lys Arg
        35                  40                  45

Ser Thr Gln Met Arg Lys Leu Met Asn Ala Tyr Cys Asp Arg Gln Ser
    50                  55                  60

Val Asp Met Asn Ser Ile Ala Phe Leu Phe Asp Gly Arg Arg Leu Arg
65                  70                  75                  80

Ala Glu Gln Thr Pro Asp Glu Leu Glu Met Glu Glu Gly Asp Glu Ile
                85                  90                  95

Asp Ala Met Leu His Gln Thr Gly Gly
            100                 105

<210> SEQ ID NO 22
<211> LENGTH: 315
<212> TYPE: DNA
<213> ORGANISM: Artificial Sequence
<220> FEATURE:
<223> OTHER INFORMATION: Nucleotide sequence of N-terminally His-tagged tomato T-SUMO gene as it appears in pET24-6xHis-T-SUMO

<400> SEQUENCE: 22
atgggtcatc accatcatca tcacggaggt tctgctagcg gcggcaccgg agatgaagat      60
aagaagccta atgatcagat ggttcatatc aatctcaagg ttaagggtca ggatgggaat     120
gaagtttttt tcaggatcaa acgtagcaca cagatgcgca agctcatgaa tgcttattgt     180
gaccggcagt cagtggacat gaactcaatt gcattcttat ttgatgggcg caggcttagg     240
gcagagcaaa ctcctgatga gctggagatg gaggagggtg atgaaatcga tgcaatgcta     300
catcaaactg gaggt                                                     315

<210> SEQ ID NO 23
<211> LENGTH: 106
<212> TYPE: PRT
<213> ORGANISM: Artificial Sequence
<220> FEATURE:
<223> OTHER INFORMATION: Amino acid sequence of N-terminally His-tagged yeast (Saccharomyces cerevisiae) Smt3 protein as it is encoded in pET24-6xHis-ySmt3

<400> SEQUENCE: 23

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile

Ile Glu Ala His Arg Glu Gln Ile Gly Gly
                100                    105

<210> SEQ ID NO 24
<211> LENGTH: 318
<212> TYPE: DNA
<213> ORGANISM: Artificial Sequence
<220> FEATURE:
<223> OTHER INFORMATION: Nucleotide sequence of N-terminally His-tagged
     yeast Smt3 gene as it appears in pET24-6xHis-ySmt3

<400> SEQUENCE: 24

```
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa aaggctgat ggaagcgttc      180 gctaaaagac agggtaagga aatggactcc ttaagattct tgtacgacgg tattagaatt     240
caagctgatc aggcccctga agatttggac atggaggata acgatattat tgaggctcac     300
agagaacaga ttggaggt                                                   318
```

<210> SEQ ID NO 25
<211> LENGTH: 239
<212> TYPE: PRT
<213> ORGANISM: Artificial Sequence
<220> FEATURE:
<223> OTHER INFORMATION: Amino acid sequence of eGFP (enhanced Green
     Fluorescent Protein)

<400> SEQUENCE: 25

Met Val Ser Lys Gly Glu Glu Leu Phe Thr Gly Val Val Pro Ile Leu
1               5                   10                15

Val Glu Leu Asp Gly Asp Val Asn Gly His Lys Phe Ser Val Ser Gly
                20                  25                 30

Glu Gly Glu Gly Asp Ala Thr Tyr Gly Lys Leu Thr Leu Lys Phe Ile
                35                  40                 45

Cys Thr Thr Gly Lys Leu Pro Val Pro Trp Pro Thr Leu Val Thr Thr
 50                   55                  60

Leu Thr Tyr Gly Val Gln Cys Phe Ser Arg Tyr Pro Asp His Met Lys
65               70                  75                 80

Gln His Asp Phe Phe Lys Ser Ala Met Pro Glu Gly Tyr Val Gln Glu
                85                  90                 95

Arg Thr Ile Phe Phe Lys Asp Asp Gly Asn Tyr Lys Thr Arg Ala Glu
                100                105             110

Val Lys Phe Glu Gly Asp Thr Leu Val Asn Arg Ile Glu Leu Lys Gly
                115                120             125

Ile Asp Phe Lys Glu Asp Gly Asn Ile Leu Gly His Lys Leu Glu Tyr
                130                135             140

Asn Tyr Asn Ser His Asn Val Tyr Ile Met Ala Asp Lys Gln Lys Asn
145             150                 155               160

Gly Ile Lys Val Asn Phe Lys Ile Arg His Asn Ile Glu Asp Gly Ser
                165                170             175

Val Gln Leu Ala Asp His Tyr Gln Gln Asn Thr Pro Ile Gly Asp Gly
                180                185             190

Pro Val Leu Leu Pro Asp Asn His Tyr Leu Ser Thr Gln Ser Ala Leu
                195                200             205

Ser Lys Asp Pro Asn Glu Lys Arg Asp His Met Val Leu Leu Glu Phe
                210                215             220

Val Thr Ala Ala Gly Ile Thr Leu Gly Met Asp Glu Leu Tyr Lys
225                 230                 235

<210> SEQ ID NO 26
<211> LENGTH: 720
<212> TYPE: DNA
<213> ORGANISM: Artificial Sequence
<220> FEATURE:
<223> OTHER INFORMATION: Nucleotide sequence of eGFP (enhanced Green
      Fluorescent Protein) gene; a fragment of NCBI acc. No. AF525449

<400> SEQUENCE: 26
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720

<210> SEQ ID NO 27
<211> LENGTH: 248
<212> TYPE: PRT
<213> ORGANISM: Artificial Sequence
<220> FEATURE:
<223> OTHER INFORMATION: Amino acid sequence of 6xHis-eGFP protein as it
      is encoded in the pET24d-6xHis-eGFP plasmid

<400> SEQUENCE: 27

Met Gly His His His His His His Gly Met Val Ser Lys Gly Glu Glu
1               5                   10                  15

Leu Phe Thr Gly Val Val Pro Ile Leu Val Glu Leu Asp Gly Asp Val
                20                  25                  30

Asn Gly His Lys Phe Ser Val Ser Gly Glu Gly Glu Gly Asp Ala Thr
            35                  40                  45

Tyr Gly Lys Leu Thr Leu Lys Phe Ile Cys Thr Thr Gly Lys Leu Pro
        50                  55                  60

Val Pro Trp Pro Thr Leu Val Thr Thr Leu Thr Tyr Gly Val Gln Cys
65                  70                  75                  80

Phe Ser Arg Tyr Pro Asp His Met Lys Gln His Asp Phe Phe Lys Ser
                85                  90                  95

Ala Met Pro Glu Gly Tyr Val Gln Glu Arg Thr Ile Phe Phe Lys Asp
                100                 105                 110

Asp Gly Asn Tyr Lys Thr Arg Ala Glu Val Lys Phe Glu Gly Asp Thr
            115                 120                 125

Leu Val Asn Arg Ile Glu Leu Lys Gly Ile Asp Phe Lys Glu Asp Gly
        130                 135                 140

Asn Ile Leu Gly His Lys Leu Glu Tyr Asn Tyr Asn Ser His Asn Val
145                 150                 155                 160

Tyr Ile Met Ala Asp Lys Gln Lys Asn Gly Ile Lys Val Asn Phe Lys
            165                 170                 175

Ile Arg His Asn Ile Glu Asp Gly Ser Val Gln Leu Ala Asp His Tyr
        180                 185                 190

Gln Gln Asn Thr Pro Ile Gly Asp Gly Pro Val Leu Leu Pro Asp Asn
    195                 200                 205

His Tyr Leu Ser Thr Gln Ser Ala Leu Ser Lys Asp Pro Asn Glu Lys
            210                 215                 220

Arg Asp His Met Val Leu Leu Glu Phe Val Thr Ala Ala Gly Ile Thr
225                 230                 235                 240

Leu Gly Met Asp Glu Leu Tyr Lys
            245

<210> SEQ ID NO 28
<211> LENGTH: 747
<212> TYPE: DNA
<213> ORGANISM: Artificial Sequence
<220> FEATURE:
<223> OTHER INFORMATION: Nucleotide sequence of 6xHis-eGFP gene as it
      appears in the pET24d-6xHis-eGFP

<400> SEQUENCE: 28
atgggtcatc accatcatca tcacgggatg gtgagcaagg gcgaggagct gttcaccggg     60
gtggtgccca tcctggtcga gctggacggc gacgtaaacg gccacaagtt cagcgtgtcc    120
ggcgagggcg agggcgatgc cacctacggc aagctgaccc tgaagttcat ctgcaccacc    180
ggcaagctgc ccgtgccctg gcccaccctc gtgaccaccc tgacctacgg cgtgcagtgc    240
ttcagccgct accccgacca catgaagcag cacgacttct tcaagtccgc catgcccgaa    300
ggctacgtcc aggagcgcac catcttcttc aaggacgacg gcaactacaa gacccgcgcc    360
gaggtgaagt tcgagggcga caccctggtg aaccgcatcg agctgaaggg catcgacttc    420
aaggaggacg gcaacatcct ggggcacaag ctggagtaca actacaacag ccacaacgtc    480
tatatcatgg ccgacaagca gaagaacggc atcaaggtga acttcaagat ccgccacaac    540
atcgaggacg gcagcgtgca gctcgccgac cactaccagc agaacacccc catcggcgac    600
ggccccgtgc tgctgcccga caaccactac ctgagcaccc agtccgccct gagcaaagac    660
cccaacgaga gcgcgatca catggtcctg ctggagttcg tgaccgccgc cgggatcact    720
ctcggcatgg acgagctgta caagtaa                                       747

<210> SEQ ID NO 29
<211> LENGTH: 343
<212> TYPE: PRT
<213> ORGANISM: Artificial Sequence
<220> FEATURE:
<223> OTHER INFORMATION: Amino acid sequence of N-terminally tagged
      human SUMO-1-eGFP as it is encoded in pET24-6xHis-hSUMO-1-eGFP

<400> SEQUENCE: 29

Met Gly His His His His His His Ser Asp Gln Glu Ala Lys Pro Ser
1               5                   10                  15

Thr Glu Asp Leu Gly Asp Lys Lys Glu Gly Glu Tyr Ile Lys Leu Lys
            20                  25                  30

Val Ile Gly Gln Asp Ser Ser Glu Ile His Phe Lys Val Lys Met Thr
        35                  40                  45

Thr His Leu Lys Lys Leu Lys Glu Ser Tyr Cys Gln Arg Gln Gly Val
    50                  55                  60

Pro Met Asn Ser Leu Arg Phe Leu Phe Glu Gly Gln Arg Ile Ala Asp
65                  70                  75                  80

```
Asn His Thr Pro Lys Glu Leu Gly Met Glu Glu Asp Val Ile Glu
                85                  90                  95
Val Tyr Gln Glu Gln Thr Gly Gly Met Val Ser Lys Gly Glu Glu Leu
            100                 105                 110
Phe Thr Gly Val Val Pro Ile Leu Val Glu Leu Asp Gly Asp Val Asn
            115                 120                 125
Gly His Lys Phe Ser Val Ser Gly Glu Gly Glu Gly Asp Ala Thr Tyr
        130                 135                 140
Gly Lys Leu Thr Leu Lys Phe Ile Cys Thr Thr Gly Lys Leu Pro Val
145                 150                 155                 160
Pro Trp Pro Thr Leu Val Thr Thr Leu Thr Tyr Gly Val Gln Cys Phe
                165                 170                 175
Ser Arg Tyr Pro Asp His Met Lys Gln His Asp Phe Phe Lys Ser Ala
                180                 185                 190
Met Pro Glu Gly Tyr Val Gln Glu Arg Thr Ile Phe Phe Lys Asp Asp
                195                 200                 205
Gly Asn Tyr Lys Thr Arg Ala Glu Val Lys Phe Glu Gly Asp Thr Leu
        210                 215                 220
Val Asn Arg Ile Glu Leu Lys Gly Ile Asp Phe Lys Glu Asp Gly Asn
225                 230                 235                 240
Ile Leu Gly His Lys Leu Glu Tyr Asn Tyr Asn Ser His Asn Val Tyr
                245                 250                 255
Ile Met Ala Asp Lys Gln Lys Asn Gly Ile Lys Val Asn Phe Lys Ile
                260                 265                 270
Arg His Asn Ile Glu Asp Gly Ser Val Gln Leu Ala Asp His Tyr Gln
                275                 280                 285
Gln Asn Thr Pro Ile Gly Asp Gly Pro Val Leu Leu Pro Asp Asn His
        290                 295                 300
Tyr Leu Ser Thr Gln Ser Ala Leu Ser Lys Asp Pro Asn Glu Lys Arg
305                 310                 315                 320
Asp His Met Val Leu Leu Glu Phe Val Thr Ala Ala Gly Ile Thr Leu
                325                 330                 335
Gly Met Asp Glu Leu Tyr Lys
            340

<210> SEQ ID NO 30
<211> LENGTH: 1032
<212> TYPE: DNA
<213> ORGANISM: Artificial Sequence
<220> FEATURE:
<223> OTHER INFORMATION: Nucleotide sequence of N-terminally tagged
      human SUMO-1-eGFP gene as it appears in pET24-6xHis-SUMO-1-eGFP

<400> SEQUENCE: 30
atgggtcatc accatcatca tcactctgac caggaggcaa aaccttcaac tgaggacttg      60
ggggataaga aggaaggtga atatattaaa ctcaaagtca ttggacagga tagcagtgag     120
attcacttca aagtgaaaat gacaacacat ctcaagaaac tcaaagaatc atactgtcaa     180
agacagggtg ttccaatgaa ttcactcagg tttctctttg agggtcagag aattgctgat     240
aatcatactc caaaagaact gggaatggag gaagaagatg tgattgaagt ttatcaggaa     300
caaacgggag gtatggtgag caagggcgag gagctgttca ccggggtggt gcccatcctg     360
gtcgagctgg acggcgacgt aaacggccac aagttcagcg tgtccggcga gggcgagggc     420
gatgccacct acggcaagct gaccctgaag ttcatctgca ccaccggcaa gctgcccgtg     480
ccctggccca ccctcgtgac caccctgacc tacggcgtgc agtgcttcag ccgctacccc     540
```

-continued

```
gaccacatga agcagcacga cttcttcaag tccgccatgc cgaaggcta cgtccaggag      600 cgcaccatct tcttcaagga cgacggcaac tacaagaccc gcgccgaggt gaagttcgag      660
ggcgacaccc tggtgaaccg catcgagctg aagggcatcg acttcaagga ggacggcaac      720
atcctggggc acaagctgga gtacaactac aacagccaca cgtctatat catggccgac      780 aagcagaaga acggcatcaa ggtgaacttc aagatccgcc acaacatcga ggacggcagc      840
gtgcagctcg ccgaccacta ccagcagaac acccccatcg gcgacggccc cgtgctgctg      900
cccgacaacc actacctgag cacccagtcc gccctgagca agacccccaa cgagaagcgc      960
gatcacatgg tcctgctgga gttcgtgacc gccgccggga tcactctcgg catggacgag     1020
ctgtacaagt aa                                                          1032
```

<210> SEQ ID NO 31
<211> LENGTH: 340
<212> TYPE: PRT
<213> ORGANISM: Artificial Sequence
<220> FEATURE:
<223> OTHER INFORMATION: Amino acid sequence of N-terminally His-tagged
human SUMO-3-eGFP protein as it is encoded in
pET24-6xHis-SUMO-3-eGFP

<400> SEQUENCE: 31

```
Met Gly His His His His His His Gly Gly Ser Glu Glu Lys Pro Lys
1               5                   10                  15

Glu Gly Val Lys Thr Glu Asn Asp His Ile Asn Leu Lys Val Ala Gly
            20                  25                  30

Gln Asp Gly Ser Val Val Gln Phe Lys Ile Lys Arg His Thr Pro Leu
        35                  40                  45

Ser Lys Leu Met Lys Ala Tyr Cys Glu Arg Gln Gly Leu Ser Met Arg
    50                  55                  60

Gln Ile Arg Phe Arg Phe Asp Gly Gln Pro Ile Asn Glu Thr Asp Thr
65                  70                  75                  80

Pro Ala Gln Leu Glu Met Glu Asp Glu Asp Thr Ile Asp Val Phe Gln
                85                  90                  95

Gln Gln Thr Gly Gly Met Val Ser Lys Gly Glu Glu Leu Phe Thr Gly
            100                 105                 110

Val Val Pro Ile Leu Val Glu Leu Asp Gly Asp Val Asn Gly His Lys
        115                 120                 125

Phe Ser Val Ser Gly Glu Gly Glu Gly Asp Ala Thr Tyr Gly Lys Leu
    130                 135                 140

Thr Leu Lys Phe Ile Cys Thr Thr Gly Lys Leu Pro Val Pro Trp Pro
145                 150                 155                 160

Thr Leu Val Thr Thr Leu Thr Tyr Gly Val Gln Cys Phe Ser Arg Tyr
                165                 170                 175

Pro Asp His Met Lys Gln His Asp Phe Phe Lys Ser Ala Met Pro Glu
            180                 185                 190

Gly Tyr Val Gln Glu Arg Thr Ile Phe Phe Lys Asp Asp Gly Asn Tyr
        195                 200                 205

Lys Thr Arg Ala Glu Val Lys Phe Glu Gly Asp Thr Leu Val Asn Arg
    210                 215                 220

Ile Glu Leu Lys Gly Ile Asp Phe Lys Glu Asp Gly Asn Ile Leu Gly
225                 230                 235                 240

His Lys Leu Glu Tyr Asn Tyr Asn Ser His Asn Val Tyr Ile Met Ala
                245                 250                 255

Asp Lys Gln Lys Asn Gly Ile Lys Val Asn Phe Lys Ile Arg His Asn
```

```
                         260                 265                 270
Ile Glu Asp Gly Ser Val Gln Leu Ala Asp His Tyr Gln Gln Asn Thr
            275                 280                 285

Pro Ile Gly Asp Gly Pro Val Leu Leu Pro Asp Asn His Tyr Leu Ser
        290                 295                 300

Thr Gln Ser Ala Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Lys
            340

<210> SEQ ID NO 32
<211> LENGTH: 1023
<212> TYPE: DNA
<213> ORGANISM: Artificial Sequence
<220> FEATURE:
<223> OTHER INFORMATION: Nucleotide sequence of N-terminally His-tagged
      human SUMO-3 -eGFP gene as it appears in pET24-6xHis-SUMO-3-eGFP

<400> SEQUENCE: 32
atgggtcatc accatcatca tcacggaggt tccgaggaga agcccaagga gggtgtgaag    60
acagagaatg accacatcaa cctgaaggtg gccgggcagg acggctccgt ggtgcagttc   120
aagatcaaga ggcacacgcc gctgagcaag ctgatgaagg cctactgcga gaggcagggc   180
ttgtcaatga ggcagatcag attcaggttc gacgggcagc caatcaatga aactgacact   240
ccagcacagc tggagatgga ggacgaggac catcgacg tgttccagca gcagacggga    300
ggtatggtga gcaagggcga ggagctgttc accggggtgg tgcccatcct ggtcgagctg   360
gacggcgacg taaacggcca caagttcagc gtgtccggcg agggcgaggg cgatgccacc   420
tacggcaagc tgacccctga gttcatctgc accaccggca agctgcccgt gccctggccc   480
accctcgtga ccaccctgac ctacggcgtg cagtgcttca gccgctaccc cgaccacatg   540
aagcagcacg acttcttcaa gtccgccatg cccgaaggct acgtccagga gcgcaccatc   600
ttcttcaagg acgacggcaa ctacaagacc cgcgccgagg tgaagttcga gggcgacacc   660
ctggtgaacc gcatcgagct gaagggcatc gacttcaagg aggacggcaa catcctgggg   720
cacaagctgg agtacaacta caacagccac aacgtctata tcatggccga caagcagaag   780
aacggcatca aggtgaactt caagatccgc cacaacatcg aggacggcag cgtgcagctc   840
gccgaccact accagcagaa cacccccatc ggcgacggcc ccgtgctgct gcccgacaac   900
cactacctga gcacccagtc cgccctgagc aaagacccca acgagaagcg cgatcacatg   960
gtcctgctgg agttcgtgac cgccgccggg atcactctcg gcatggacga gctgtacaag  1020
taa                                                                1023

<210> SEQ ID NO 33
<211> LENGTH: 341
<212> TYPE: PRT
<213> ORGANISM: Artificial Sequence
<220> FEATURE:
<223> OTHER INFORMATION: Amino acid sequence of N-terminally His-tagged
      Arabidopsis thalania SUMO1-eGFP protein as it is encoded in
      pET24-6xHis-AtSUMO1-eGFP

<400> SEQUENCE: 33

Met Gly His His His His His His Gly Gly Ser Ala Asn Gln Glu Glu
1               5                   10                  15

Asp Lys Lys Pro Gly Asp Gly Gly Ala His Ile Asn Leu Lys Val Lys
```

```
            20                  25                  30
Gly Gln Asp Gly Asn Glu Val Phe Phe Arg Ile Lys Arg Ser Thr Gln
        35                  40                  45
Leu Lys Lys Leu Met Asn Ala Tyr Cys Asp Arg Gln Ser Val Asp Met
50                  55                  60
Asn Ser Ile Ala Phe Leu Phe Asp Gly Arg Arg Leu Arg Ala Glu Gln
65                  70                  75                  80
Thr Pro Asp Glu Leu Asp Met Glu Asp Gly Glu Ile Asp Ala Met
                85                  90                  95
Leu His Gln Thr Gly Gly Met Val Ser Lys Gly Glu Glu Leu Phe Thr
            100                 105                 110
Gly Val Val Pro Ile Leu Val Glu Leu Asp Gly Asp Val Asn Gly His
            115                 120                 125
Lys Phe Ser Val Ser Gly Glu Gly Glu Gly Asp Ala Thr Tyr Gly Lys
        130                 135                 140
Leu Thr Leu Lys Phe Ile Cys Thr Thr Gly Lys Leu Pro Val Pro Trp
145                 150                 155                 160
Pro Thr Leu Val Thr Thr Leu Thr Tyr Gly Val Gln Cys Phe Ser Arg
                165                 170                 175
Tyr Pro Asp His Met Lys Gln His Asp Phe Phe Lys Ser Ala Met Pro
            180                 185                 190
Glu Gly Tyr Val Gln Glu Arg Thr Ile Phe Phe Lys Asp Asp Gly Asn
        195                 200                 205
Tyr Lys Thr Arg Ala Glu Val Lys Phe Glu Gly Asp Thr Leu Val Asn
    210                 215                 220
Arg Ile Glu Leu Lys Gly Ile Asp Phe Lys Glu Asp Gly Asn Ile Leu
225                 230                 235                 240
Gly His Lys Leu Glu Tyr Asn Tyr Asn Ser His Asn Val Tyr Ile Met
                245                 250                 255
Ala Asp Lys Gln Lys Asn Gly Ile Lys Val Asn Phe Lys Ile Arg His
            260                 265                 270
Asn Ile Glu Asp Gly Ser Val Gln Leu Ala Asp His Tyr Gln Gln Asn
        275                 280                 285
Thr Pro Ile Gly Asp Gly Pro Val Leu Leu Pro Asp Asn His Tyr Leu
    290                 295                 300
Ser Thr Gln Ser Ala Leu Ser Lys Asp Pro Asn Glu Lys Arg Asp His
305                 310                 315                 320
Met Val Leu Leu Glu Phe Val Thr Ala Ala Gly Ile Thr Leu Gly Met
                325                 330                 335
Asp Glu Leu Tyr Lys
            340

<210> SEQ ID NO 34
<211> LENGTH: 1026
<212> TYPE: DNA
<213> ORGANISM: Artificial Sequence
<220> FEATURE:
<223> OTHER INFORMATION: Nucleotide sequence of N-terminally His-tagged
      Arabidopsis thalania SUMO1-eGFP gene as it appears in
      pET24-6xHis-AtSUMO1-eGFP

<400> SEQUENCE: 34
atgggtcatc accatcatca tcacggaggt tctgcaaacc aggaggaaga caagaagcca    60
ggagacggag gagctcacat caatctcaaa gtcaagggac aggatggaaa cgaggttttc   120
tttaggatca agagaagcac tcagctcaag aagctgatga atgcttactg tgaccggcaa   180
```

```
tctgtggaca tgaactccat tgctttcttg tttgatgggc gtcgtcttcg tgctgagcaa    240
actcccgatg agcttgacat ggaggatggt gatgagatcg atgcgatgct ccatcagact    300
ggaggtatgg tgagcaaggg cgaggagctg ttcaccgggg tggtgcccat cctggtcgag    360
ctggacggcg acgtaaacgg ccacaagttc agcgtgtccg gcgagggcga gggcgatgcc    420
acctacggca agctgaccct gaagttcatc tgcaccaccg gcaagctgcc cgtgccctgg    480
cccaccctcg tgaccaccct gacctacggc gtgcagtgct tcagccgcta ccccgaccac    540
atgaagcagc acgacttctt caagtccgcc atgcccgaag ctacgtcca ggagcgcacc    600 atcttcttca aggacgacgg caactacaag acccgcgccg aggtgaagtt cgagggcgac    660 acctggtga accgcatcga gctgaagggc atcgacttca aggaggacgg caacatcctg    720
gggcacaagc tggagtacaa ctacaacagc cacaacgtct atatcatggc cgacaagcag    780
aagaacggca tcaaggtgaa cttcaagatc cgccacaaca tcgaggacgg cagcgtgcag    840
ctcgccgacc actaccagca gaacacccccc atcggcacg ccccgtgct gctgcccgac    900 aaccactacc tgagcaccca gtccgccctg agcaaagacc ccaacgagaa gcgcgatcac    960
atggtcctgc tggagttcgt gaccgccgcc gggatcactc tcggcatgga cgagctgtac    1020
aagtaa                                                              1026
```

<210> SEQ ID NO 35
<211> LENGTH: 340
<212> TYPE: PRT
<213> ORGANISM: Artificial Sequence
<220> FEATURE:
<223> OTHER INFORMATION: Amino acid sequence of N-terminally His-tagged
      Arabidopsis thalania SUMO2-eGPF protein as it is encoded in
      pET24-6xHis-AtSUMO2-eGFP

<400> SEQUENCE: 35

```
Met Gly His His His His His Gly Gly Ser Ala Thr Pro Glu Glu
1               5                   10                  15

Asp Lys Lys Pro Asp Gln Gly Ala His Ile Asn Leu Lys Val Lys Gly
            20                  25                  30

Gln Asp Gly Asn Glu Val Phe Phe Arg Ile Lys Arg Ser Thr Gln Leu
        35                  40                  45

Lys Lys Leu Met Asn Ala Tyr Cys Asp Arg Gln Ser Val Asp Phe Asn
50                  55                  60

Ser Ile Ala Phe Leu Phe Asp Gly Arg Arg Leu Arg Ala Glu Gln Thr
65                  70                  75                  80

Pro Asp Glu Leu Glu Met Glu Asp Gly Asp Ile Asp Ala Met Leu
            85                  90                  95

His Gln Thr Gly Gly Met Val Ser Lys Gly Glu Glu Leu Phe Thr Gly
            100                 105                 110

Val Val Pro Ile Leu Val Glu Leu Asp Gly Asp Val Asn Gly His Lys
        115                 120                 125

Phe Ser Val Ser Gly Glu Gly Glu Gly Asp Ala Thr Tyr Gly Lys Leu
    130                 135                 140

Thr Leu Lys Phe Ile Cys Thr Thr Gly Lys Leu Pro Val Pro Trp Pro
145                 150                 155                 160

Thr Leu Val Thr Thr Leu Thr Tyr Gly Val Gln Cys Phe Ser Arg Tyr
                165                 170                 175

Pro Asp His Met Lys Gln His Asp Phe Phe Lys Ser Ala Met Pro Glu
            180                 185                 190

Gly Tyr Val Gln Glu Arg Thr Ile Phe Phe Lys Asp Asp Gly Asn Tyr
        195                 200                 205
```

```
Lys Thr Arg Ala Glu Val Lys Phe Glu Gly Asp Thr Leu Val Asn Arg
    210                 215                 220
Ile Glu Leu Lys Gly Ile Asp Phe Lys Glu Asp Gly Asn Ile Leu Gly
225                 230                 235                 240
His Lys Leu Glu Tyr Asn Tyr Asn Ser His Asn Val Tyr Ile Met Ala
                245                 250                 255
Asp Lys Gln Lys Asn Gly Ile Lys Val Asn Phe Lys Ile Arg His Asn
                260                 265                 270
Ile Glu Asp Gly Ser Val Gln Leu Ala Asp His Tyr Gln Gln Asn Thr
            275                 280                 285
Pro Ile Gly Asp Gly Pro Val Leu Leu Pro Asp Asn His Tyr Leu Ser
290                 295                 300
Thr Gln Ser Ala Leu Ser Lys Asp Pro Asn Glu Lys Arg Asp His Met
305                 310                 315                 320
Val Leu Leu Glu Phe Val Thr Ala Ala Gly Ile Thr Leu Gly Met Asp
                325                 330                 335
Glu Leu Tyr Lys
        340

<210> SEQ ID NO 36
<211> LENGTH: 1023
<212> TYPE: DNA
<213> ORGANISM: Artificial Sequence
<220> FEATURE:
<223> OTHER INFORMATION: Nucleotide sequence of N-terminally His-tagged
      Arabidopsis thalania SUMO2-eGFP gene as it appears in
      pET24-6xHis-AtSUMO2-eGFP

<400> SEQUENCE: 36
atgggtcatc accatcatca tcacggaggt tctgctactc cggaagaaga caagaagcct      60
gaccaaggag ctcacatcaa tctcaaagtc aagggacagg atggtaatga agtcttcttt     120
aggatcaaga gaagcactca gctcaaaaaa ctgatgaatg cttactgtga ccgtcagtct     180
gtggatttca actcaattgc tttcttgttt gatggtcgtc gtcttcgtgc cgagcagact     240
ccagatgagc ttgaaatgga agatggagat gagatcgatg caatgcttca tcagactgga     300
ggtatggtga gcaagggcga ggagctgttc accggggtgg tgcccatcct ggtcgagctg     360
gacggcgacg taaacggcca caagttcagc gtgtccggcg agggcgaggg cgatgccacc     420
tacggcaagc tgaccctgaa gttcatctgc accaccggca agctgcccgt gccctggccc     480
accctcgtga ccaccctgac ctacggcgtg cagtgcttca gccgctaccc cgaccacatg     540
aagcagcacg acttcttcaa gtccgccatg cccgaaggct acgtccagga gcgcaccatc     600
ttcttcaagg acgacggcaa ctacaagacc cgcgccgagg tgaagttcga gggcgacacc     660
ctggtgaacc gcatcgagct gaagggcatc gacttcaagg aggacggcaa catcctgggg     720
cacaagctgg agtacaacta caacagccac aacgtctata tcatggccga caagcagaag     780
aacggcatca aggtgaactt caagatccgc cacaacatcg aggacggcag cgtgcagctc     840
gccgaccact accagcagaa cacccccatc ggcgacggcc ccgtgctgct gcccgacaac     900
cactacctga gcacccagtc cgccctgagc aaagacccca acgagaagcg cgatcacatg     960
gtcctgctgg agttcgtgac cgccgccggg atcactctcg gcatggacga gctgtacaag    1020
taa                                                                  1023

<210> SEQ ID NO 37
<211> LENGTH: 344
<212> TYPE: PRT
```

-continued

```
<213> ORGANISM: Artificial Sequence
<220> FEATURE:
<223> OTHER INFORMATION: Amino acid sequence of N-terminally His-tagged
      tomato (Lycopersicum esculentum) T-SUMO-eGFP protein as it is
      encoded in pET24-6xHis-T-SUMO-eGFP

<400> SEQUENCE: 37

Met Gly His His His His His His Gly Gly Ser Ala Ser Gly Gly Thr
1               5                   10                  15

Gly Asp Glu Asp Lys Lys Pro Asn Asp Gln Met Val His Ile Asn Leu
            20                  25                  30

Lys Val Lys Gly Gln Asp Gly Asn Glu Val Phe Phe Arg Ile Lys Arg
        35                  40                  45

Ser Thr Gln Met Arg Lys Leu Met Asn Ala Tyr Cys Asp Arg Gln Ser
    50                  55                  60

Val Asp Met Asn Ser Ile Ala Phe Leu Phe Asp Gly Arg Arg Leu Arg
65                  70                  75                  80

Ala Glu Gln Thr Pro Asp Glu Leu Glu Met Glu Glu Gly Asp Glu Ile
                85                  90                  95

Asp Ala Met Leu His Gln Thr Gly Gly Met Val Ser Lys Gly Glu Glu
            100                 105                 110

Leu Phe Thr Gly Val Val Pro Ile Leu Val Glu Leu Asp Gly Asp Val
        115                 120                 125

Asn Gly His Lys Phe Ser Val Ser Gly Glu Gly Glu Gly Asp Ala Thr
    130                 135                 140

Tyr Gly Lys Leu Thr Leu Lys Phe Ile Cys Thr Thr Gly Lys Leu Pro
145                 150                 155                 160

Val Pro Trp Pro Thr Leu Val Thr Thr Leu Thr Tyr Gly Val Gln Cys
                165                 170                 175

Phe Ser Arg Tyr Pro Asp His Met Lys Gln His Asp Phe Phe Lys Ser
            180                 185                 190

Ala Met Pro Glu Gly Tyr Val Gln Glu Arg Thr Ile Phe Phe Lys Asp
        195                 200                 205

Asp Gly Asn Tyr Lys Thr Arg Ala Glu Val Lys Phe Glu Gly Asp Thr
    210                 215                 220

Leu Val Asn Arg Ile Glu Leu Lys Gly Ile Asp Phe Lys Glu Asp Gly
225                 230                 235                 240

Asn Ile Leu Gly His Lys Leu Glu Tyr Asn Tyr Asn Ser His Asn Val
                245                 250                 255

Tyr Ile Met Ala Asp Lys Gln Lys Asn Gly Ile Lys Val Asn Phe Lys
            260                 265                 270

Ile Arg His Asn Ile Glu Asp Gly Ser Val Gln Leu Ala Asp His Tyr
        275                 280                 285

Gln Gln Asn Thr Pro Ile Gly Asp Gly Pro Val Leu Leu Pro Asp Asn
    290                 295                 300

His Tyr Leu Ser Thr Gln Ser Ala Leu Ser Lys Asp Pro Asn Glu Lys
305                 310                 315                 320

Arg Asp His Met Val Leu Leu Glu Phe Val Thr Ala Ala Gly Ile Thr
                325                 330                 335

Leu Gly Met Asp Glu Leu Tyr Lys
            340

<210> SEQ ID NO 38
<211> LENGTH: 1035
<212> TYPE: DNA
<213> ORGANISM: Artificial Sequence
<220> FEATURE:
```

<223> OTHER INFORMATION: Nucleotide sequence of N-terminally His-tagged
      tomato T-SUMO-eGFP gene as it appears in pET24-6xHis-T-SUM-eGFP

<400> SEQUENCE: 38

```
atgggtcatc accatcatca tcacggaggt tctgctagcg gcggcaccgg agatgaagat    60
aagaagccta atgatcagat ggttcatatc aatctcaagg ttaagggtca ggatgggaat   120
gaagtttttt tcaggatcaa acgtagcaca cagatgcgca agctcatgaa tgcttattgt   180
gaccggcagt cagtggacat gaactcaatt gcattcttat ttgatgggcg caggcttagg   240
gcagagcaaa ctcctgatga gctggagatg gaggagggtg atgaaatcga tgcaatgcta   300
catcaaactg gaggtatggt gagcaagggc gaggagctgt tcaccggggt ggtgcccatc   360
ctggtcgagc tggacggcga cgtaaacggc cacaagttca gcgtgtccgg cgagggcgag   420
ggcgatgcca cctacggcaa gctgaccctg aagttcatct gcaccaccgg caagctgccc   480
gtgccctggc ccaccctcgt gaccaccctg acctacggcg tgcagtgctt cagccgctac   540
cccgaccaca tgaagcagca cgacttcttc aagtccgcca tgcccgaagg ctacgtccag   600
gagcgcacca tcttcttcaa ggacgacggc aactacaaga cccgcgccga ggtgaagttc   660
gagggcgaca ccctggtgaa ccgcatcgag ctgaagggca tcgacttcaa ggaggacggc   720
aacatcctgg ggcacaagct ggagtacaac tacaacagcc acaacgtcta tatcatggcc   780
gacaagcaga agaacggcat caaggtgaac ttcaagatcc gccacaacat cgaggacggc   840
agcgtgcagc tcgccgacca ctaccagcag aacacccca tcggcgacgg ccccgtgctg   900
ctgcccgaca ccactacct gagcacccag tccgccctga gcaaagaccc caacgagaag   960
cgcgatcaca tggtcctgct ggagttcgtg accgccgccg ggatcactct cggcatggac  1020
gagctgtaca agtaa                                                   1035
```

<210> SEQ ID NO 39
<211> LENGTH: 345
<212> TYPE: PRT
<213> ORGANISM: Artificial Sequence
<220> FEATURE:
<223> OTHER INFORMATION: Amino acid sequence of N-terminally His-tagged
      yeast (Saccharomyces cerevisiae) Smt3-eGFP protein as it is
      encoded in pET24-6xHis-ySmt3-eGFP

<400> SEQUENCE: 39

```
Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
                85                  90                  95

Ile Glu Ala His Arg Glu Gln Ile Gly Gly Met Val Ser Lys Gly Glu
            100                 105                 110

Glu Leu Phe Thr Gly Val Val Pro Ile Leu Val Glu Leu Asp Gly Asp
        115                 120                 125

Val Asn Gly His Lys Phe Ser Val Ser Gly Glu Gly Glu Gly Asp Ala
    130                 135                 140
```

```
Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Leu Thr Tyr Gly Val Gln
                165                 170                 175

Cys Phe Ser Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
        195                 200                 205

Asp Asp Gly Asn Tyr Lys Thr Arg Ala Glu Val Lys Phe Glu Gly Asp
    210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
                245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285

Tyr Gln Gln Asn Thr Pro Ile Gly Asp Gly Pro Val Leu Leu Pro Asp
    290                 295                 300

Asn His Tyr Leu Ser Thr Gln Ser Ala Leu Ser Lys Asp Pro Asn Glu
305                 310                 315                 320

Lys Arg Asp His Met Val Leu Leu Glu Phe Val Thr Ala Ala Gly Ile
                325                 330                 335

Thr Leu Gly Met Asp Glu Leu Tyr Lys
                340                 345

<210> SEQ ID NO 40
<211> LENGTH: 1038
<212> TYPE: DNA
<213> ORGANISM: Artificial Sequence
<220> FEATURE:
<223> OTHER INFORMATION: Nucleotide sequence of N-terminally His-tagged
      yeast Smt3-eGFP gene as it appears in pET24-6xHis-ySmt3-eGFP

<400> SEQUENCE: 40
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
gctaaaagac agggtaagga aatggactcc ttaagattct tgtacgacgg tattagaatt     240
caagctgatc aggcccctga gatttggac atggaggata cgatattat tgaggctcac      300 agagaacaga ttggaggtat ggtgagcaag ggcgaggagc tgttcaccgg ggtggtgccc     360
atcctggtcg agctggacgg cgacgtaaac ggccacaagt tcagcgtgtc cggcgagggc     420
gagggcgatg ccacctacgg caagctgacc ctgaagttca tctgcaccac cggcaagctg     480
cccgtgccct ggcccaccct cgtgaccacc ctgacctacg gcgtgcagtg cttcagccgc     540
taccccgacc acatgaagca gcacgacttc ttcaagtccg ccatgcccga aggctacgtc     600
caggagcgca ccatcttctt caaggacgac ggcaactaca agacccgcgc cgaggtgaag     660
ttcgagggcg acaccctggt gaaccgcatc gagctgaagg gcatcgactt caaggaggac     720
ggcaacatcc tggggcacaa gctggagtac aactacaaca gccacaacgt ctatatcatg     780
gccgacaagc agaagaacgg catcaaggtg aacttcaaga tccgccacaa catcgaggac     840
ggcagcgtgc agctcgccga ccactaccag cagaacaccc ccatcggcga cggccccgtg     900
```

```
ctgctgcccg acaaccacta cctgagcacc cagtccgccc tgagcaaaga ccccaacgag    960
aagcgcgatc acatggtcct gctggagttc gtgaccgccg ccgggatcac tctcggcatg   1020
gacgagctgt acaagtaa                                                  1038
```

<210> SEQ ID NO 41
<211> LENGTH: 234
<212> TYPE: PRT
<213> ORGANISM: Artificial Sequence
<220> FEATURE:
<223> OTHER INFORMATION: Amino acid sequence of C-terminally His-tagged
      human SENP1 catalytic domain as it is encoded in pET24-hSENP1

<400> SEQUENCE: 41

```
Met Ala Ser Phe Pro Glu Ile Thr Glu Glu Met Glu Lys Glu Ile Lys
1               5                  10                  15

Asn Val Phe Arg Asn Gly Asn Gln Asp Glu Val Leu Ser Glu Ala Phe
            20                  25                  30

Arg Leu Thr Ile Thr Arg Lys Asp Ile Gln Thr Leu Asn His Leu Asn
        35                  40                  45

Trp Leu Asn Asp Glu Ile Ile Asn Phe Tyr Met Asn Met Leu Met Glu
    50                  55                  60

Arg Ser Lys Glu Lys Gly Leu Pro Ser Val His Ala Phe Asn Thr Phe
65                  70                  75                  80

Phe Phe Thr Lys Leu Lys Thr Ala Gly Tyr Gln Ala Val Lys Arg Trp
                85                  90                  95

Thr Lys Lys Val Asp Val Phe Ser Val Asp Ile Leu Leu Val Pro Ile
            100                 105                 110

His Leu Gly Val His Trp Cys Leu Ala Val Val Asp Phe Arg Lys Lys
        115                 120                 125

Asn Ile Thr Tyr Tyr Asp Ser Met Gly Gly Ile Asn Asn Glu Ala Cys
    130                 135                 140

Arg Ile Leu Leu Gln Tyr Leu Lys Gln Glu Ser Ile Asp Lys Lys Arg
145                 150                 155                 160

Lys Glu Phe Asp Thr Asn Gly Trp Gln Leu Phe Ser Lys Lys Ser Gln
                165                 170                 175

Ile Pro Gln Gln Met Asn Gly Ser Asp Cys Gly Met Phe Ala Cys Lys
            180                 185                 190

Tyr Ala Asp Cys Ile Thr Lys Asp Arg Pro Ile Asn Phe Thr Gln Gln
        195                 200                 205

His Met Pro Tyr Phe Arg Lys Arg Met Val Trp Glu Ile Leu His Arg
    210                 215                 220

Lys Leu Leu Glu His His His His His
225                 230
```

<210> SEQ ID NO 42
<211> LENGTH: 702
<212> TYPE: DNA
<213> ORGANISM: Artificial Sequence
<220> FEATURE:
<223> OTHER INFORMATION: Nucleotide sequence of C-terminally His-tagged
      human SENP1 partial gene as it appears in pET24-hSENP1

<400> SEQUENCE: 42

```
atggctagct ttcctgaaat tacagaggaa atggagaaag aaataaagaa tgtatttcgt    60
aatgggaatc aggatgaagt tctcagtgaa gcatttcgcc tgaccattac acgcaaagat   120
attcaaactc taaaccatct gaattggctc aatgatgaga tcatcaattt ctacatgaat   180
atgctgatgg agcgaagtaa agagaagggc ttgccaagtg tgcatgcatt taataccttt   240
```

```
ttcttcacta aattaaaaac ggctggttat caggcagtga aacgttggac aaagaaagta    300
gatgtatttt ctgttgacat tcttttggtg cccattcacc tgggagtaca ctggtgtcta    360
gctgttgtgg actttagaaa gaagaatatt acctattacg actccatggg tgggataaac    420
aatgaagcct gcagaatact cttgcaatac ctaaagcaag aaagcattga caagaaaagg    480
aaagagtttg acaccaatgg ctggcagctt ttcagcaaga aaagccagat tcctcagcag    540
atgaatggaa gtgactgtgg atgtttgcc tgcaaatatg ctgactgtat taccaaagac    600
agaccaatca acttcacaca gcaacacatg ccatacttcc ggaagcggat ggtctgggag    660
atcctccacc gaaaactcct cgagcaccac caccaccacc ac                      702
```

<210> SEQ ID NO 43
<211> LENGTH: 239
<212> TYPE: PRT
<213> ORGANISM: Artificial Sequence
<220> FEATURE:
<223> OTHER INFORMATION: Amino acid sequence of C-terminally His-tagged
      human SENP2 catalytic domain as it is encoded in pET24-hSENP2

<400> SEQUENCE: 43

```
Met Ala Ser Leu Leu Glu Leu Thr Glu Asp Met Glu Lys Glu Ile Ser
1               5                   10                  15

Asn Ala Leu Gly His Gly Pro Gln Asp Glu Ile Leu Ser Ser Ala Phe
            20                  25                  30

Lys Leu Arg Ile Thr Arg Gly Asp Ile Gln Thr Leu Lys Asn Tyr His
        35                  40                  45

Trp Leu Asn Asp Glu Val Ile Asn Phe Tyr Met Asn Leu Leu Val Glu
    50                  55                  60

Arg Asn Lys Lys Gln Gly Tyr Pro Ala Leu His Val Phe Ser Thr Phe
65                  70                  75                  80

Phe Tyr Pro Lys Leu Lys Ser Gly Gly Tyr Gln Ala Val Lys Arg Trp
                85                  90                  95

Thr Lys Gly Val Asn Leu Phe Glu Gln Glu Ile Ile Leu Val Pro Ile
            100                 105                 110

His Arg Lys Val His Trp Ser Leu Val Val Ile Asp Leu Arg Lys Lys
        115                 120                 125

Cys Leu Lys Tyr Leu Asp Ser Met Gly Gln Lys Gly His Arg Ile Cys
    130                 135                 140

Glu Ile Leu Leu Gln Tyr Leu Gln Asp Glu Ser Lys Thr Lys Arg Asn
145                 150                 155                 160

Ser Asp Leu Asn Leu Leu Glu Trp Thr His His Ser Met Lys Pro His
                165                 170                 175

Glu Ile Pro Gln Gln Leu Asn Gly Ser Asp Cys Gly Met Phe Thr Cys
            180                 185                 190

Lys Tyr Ala Asp Tyr Ile Ser Arg Asp Lys Pro Ile Thr Phe Thr Gln
        195                 200                 205

His Gln Met Pro Leu Phe Arg Lys Lys Met Val Trp Glu Ile Leu His
    210                 215                 220

Gln Gln Leu Leu Ala Ala Ala Leu Glu His His His His His His
225                 230                 235
```

<210> SEQ ID NO 44
<211> LENGTH: 717
<212> TYPE: DNA
<213> ORGANISM: Artificial Sequence
<220> FEATURE:
<223> OTHER INFORMATION: Nucleotide sequence of C-terminally His-tagged -continued human SENP2 partial gene as it appears in pET24-hSENP2

<400> SEQUENCE: 44

```
atggctagcc tccttgaact tacagaggac atggaaaagg aaatcagtaa tgccctaggc      60
catggcccac aggatgaaat cctaagtagt gctttcaaat tgcgaattac tcgaggagat     120
attcagacat taaagaacta tcactggctc aatgatgaag tcattaattt ttacatgaat     180
cttctggtgg aaagaaataa aaagcaaggc tatccagcac ttcatgtatt cagtactttc     240
ttctatccta aattaaagtc tgggggttac caagcagtga acgatggac caaaggggta      300
aatctctttg aacaagaaat tattctggtg cctattcatc ggaaggtaca ttggagcctg     360
gtggtgattg acctaagaaa aaagtgtctt aaatatctgg attctatggg acaaaagggc     420
cacaggatct gtgagattct ccttcagtat ttacaggatg aaagtaagac caaaagaaat     480
agtgatctga atcttttaga gtggacccat cacagcatga accacacga gattcctcaa     540
cagctgaatg ggagtgattg tggaatgttt acttgtaaat atgcagatta tatttctagg     600
gacaaaccta tcacatttac tcagcaccag atgcctctct tccggaagaa gatggtgtgg     660
gaaatccttc atcagcagtt gctggcggcc gcactcgagc accaccacca ccaccac      717
```

<210> SEQ ID NO 45
<211> LENGTH: 481
<212> TYPE: PRT
<213> ORGANISM: Artificial Sequence
<220> FEATURE:
<223> OTHER INFORMATION: Amino acid sequence of C-terminally His-tagged
      human SENP6 catalytic domain as it is encoded in pET24-hSENP6

<400> SEQUENCE: 45

```
Met Gly Glu Asn His Thr Ile Phe Ile Gly Pro Val Glu Lys Leu Ile
  1               5                  10                  15

Val Tyr Pro Pro Pro Ala Lys Gly Gly Ile Ser Val Thr Asn Glu
             20                  25                  30

Asp Leu His Cys Leu Asn Glu Gly Glu Phe Leu Asn Asp Val Ile Ile
             35                  40                  45

Asp Phe Tyr Leu Lys Tyr Leu Val Leu Glu Lys Leu Lys Lys Glu Asp
         50                  55                  60

Ala Asp Arg Ile His Ile Phe Ser Ser Phe Tyr Lys Arg Leu Asn
 65                  70                  75                  80

Gln Arg Glu Arg Arg Asn His Glu Thr Thr Asn Leu Ser Ile Gln Gln
                 85                  90                  95

Lys Arg His Gly Arg Val Lys Thr Trp Thr Arg His Val Asp Ile Phe
            100                 105                 110

Glu Lys Asp Phe Ile Phe Val Pro Leu Asn Glu Ala Ala His Trp Phe
        115                 120                 125

Leu Ala Val Val Cys Phe Pro Gly Leu Glu Lys Pro Lys Tyr Glu Pro
    130                 135                 140

Asn Pro His Tyr His Glu Asn Ala Val Ile Gln Lys Cys Ser Thr Val
145                 150                 155                 160

Glu Asp Ser Cys Ile Ser Ser Ala Ser Met Glu Ser Cys Ser
                165                 170                 175

Gln Asn Ser Ser Ala Lys Pro Val Ile Lys Met Leu Asn Lys Lys
            180                 185                 190

His Cys Ile Ala Val Ile Asp Ser Asn Pro Gly Gln Glu Glu Ser Asp
        195                 200                 205

Pro Arg Tyr Lys Arg Asn Ile Cys Ser Val Lys Tyr Ser Val Lys Lys
    210                 215                 220
```

-continued

```
Ile Asn His Thr Ala Ser Glu Asn Glu Glu Phe Asn Lys Gly Glu Ser
225                 230                 235                 240

Thr Ser Gln Lys Val Ala Asp Arg Thr Lys Ser Glu Asn Gly Leu Gln
            245                 250                 255

Asn Glu Ser Leu Ser Ser Thr His His Thr Asp Gly Leu Ser Lys Ile
        260                 265                 270

Arg Leu Asn Tyr Ser Asp Glu Ser Pro Glu Ala Gly Lys Met Leu Glu
    275                 280                 285

Asp Glu Leu Val Asp Phe Ser Glu Asp Gln Asn Gln Asp Asp Ser
290                 295                 300

Ser Asp Asp Gly Phe Leu Ala Asp Asp Asn Cys Ser Ser Glu Ile Gly
305                 310                 315                 320

Gln Trp His Leu Lys Pro Thr Ile Cys Lys Gln Pro Cys Ile Leu Leu
            325                 330                 335

Met Asp Ser Leu Arg Gly Pro Ser Arg Ser Asn Val Val Lys Ile Leu
        340                 345                 350

Arg Glu Tyr Leu Glu Val Glu Trp Glu Val Lys Lys Gly Ser Lys Arg
    355                 360                 365

Ser Phe Ser Lys Asp Val Met Lys Gly Ser Asn Pro Lys Val Pro Gln
370                 375                 380

Gln Asn Asn Phe Ser Asp Cys Gly Val Tyr Val Leu Gln Tyr Val Glu
385                 390                 395                 400

Ser Phe Phe Glu Asn Pro Ile Leu Ser Phe Glu Leu Pro Met Asn Leu
            405                 410                 415

Ala Asn Trp Phe Pro Pro Arg Met Arg Thr Lys Arg Glu Glu Ile
        420                 425                 430

Arg Asn Ile Ile Leu Lys Leu Gln Glu Asp Gln Ser Lys Glu Lys Arg
    435                 440                 445

Lys His Lys Asp Thr Tyr Ser Thr Glu Ala Pro Leu Gly Gly Gly Thr
450                 455                 460

Glu Gln Tyr Val Asn Ser Ile Ser Asp Leu Glu His His His His
465                 470                 475                 480

His
```

<210> SEQ ID NO 46
<211> LENGTH: 1443
<212> TYPE: DNA
<213> ORGANISM: Artificial Sequence
<220> FEATURE:
<223> OTHER INFORMATION: Nucleotide sequence of C-terminally His-tagged human SENP6 partial gene as it appears in pET24-hSENP6

<400> SEQUENCE: 46

```
atgggagaaa accacaccat cttcattggc ccagtagaaa agttgatagt atatccacca       60
cctccagcta agggaggcat ctctgttacc aatgaggacc tgcactgtct aaatgaagga      120
gaatttttaa atgatgttat tatagacttt tatttgaaat acttggtgct tgaaaaactg      180
aagaaggaag acgctgaccg aattcatata ttcagttctt ttttctataa acgccttaat      240
cagagagaga ggagaaatca tgaaacaact aatctgtcaa tacagcaaaa acggcatggg      300
agagtaaaaa catggacccg gcacgtagat attttttgaga aggattttat ttttgtaccc      360
cttaatgaag ctgcacactg gttttttggct gttgtttgtt tccccggttt ggaaaaacca      420
aagtatgaac ctaatcctca ttaccatgaa aatgctgtca tacagaaatg ttcaactgta      480
gaggacagtt gtatttcttc ttcagccagt gaaatggaga gttgttcaca aaactcttct      540
```

```
gccaagcctg taattaagaa gatgctaaac aaaaaacatt gcatagctgt aattgattcc    600
aatcctgggc aggaagaaag tgaccctcgt tataagagaa acatatgcag tgtaaaatac    660
agtgtgaaaa aaataaatca tactgcgagt gaaaatgaag aattcaataa aggagaatct    720
acatcccaga aagttgctga taggactaaa agtgagaatg ccctacagaa tgaaagttta    780
agttccacac atcatacaga tggcttaagc aaaatcagac taaactatag cgatgaatca    840
cctgaagctg gtaaaatgct tgaagatgaa ctcgtcgact tctcagaaga tcaggataac    900
caggatgata gcagtgacga tggattcctc gctgatgaca actgcagttc agaaatagga    960
cagtggcatt taaagcctac tatctgtaaa caaccttgta tcctacttat ggactcactc   1020
cgaggccctt ctcggtcaaa tgttgtcaaa attttaagag agtatttaga agtggaatgg   1080
gaagttaaaa aaggaagcaa aagaagtttt tccaaagatg ttatgaaggg ctctaatcca   1140
aaagtaccac agcaaaacaa cttcagtgac tgtggtgtat atgtattgca gtatgtagag   1200 agctttttg agaatccaat tctcagtttt gaactaccta tgaatttggc aaactggttt    1260
cctccaccaa gaatgagaac aaaaagagaa gaaatccgaa acataattct gaagctacag   1320
gaagatcaga gcaaagagaa aagaaagcat aaggacactt actcaacaga agcacccttac  1380 ggcgaaggaa cagaacaata tgtcaatagt atctcagatc tcgagcacca ccaccaccac   1440
cac                                                                 1443
```

<210> SEQ ID NO 47
<211> LENGTH: 279
<212> TYPE: PRT
<213> ORGANISM: Artificial Sequence
<220> FEATURE:
<223> OTHER INFORMATION: Amino acid sequence of C-terminally His-tagged
      Arabidopsis thalania ULP1c catalytic domain as it is encoded in
      pET24-AtULP1c

<400> SEQUENCE: 47

```
Met Val Val Glu Glu Ala Cys Glu Leu Pro Glu Gly Leu Pro Glu Asp
1               5                   10                  15

Ile Tyr Tyr Pro Ser Ser Asp Gln Ser Asp Gly Arg Asp Leu Val Gln
            20                  25                  30

Val Ser Leu Lys Asp Leu Lys Cys Leu Ser Pro Gly Glu Tyr Leu Thr
        35                  40                  45

Ser Pro Val Ile Asn Phe Tyr Ile Arg Tyr Val Gln His His Val Phe
    50                  55                  60

Ser Ala Asp Lys Thr Ala Ala Asn Cys His Phe Phe Asn Thr Phe Phe
65                  70                  75                  80

Tyr Lys Lys Leu Thr Glu Ala Val Ser Tyr Lys Gly Asn Asp Arg Asp
                85                  90                  95

Ala Tyr Phe Val Lys Phe Arg Arg Trp Trp Lys Gly Phe Asp Leu Phe
            100                 105                 110

Cys Lys Ser Tyr Ile Phe Ile Pro Ile His Glu Asp Leu His Trp Ser
        115                 120                 125

Leu Val Ile Ile Cys Ile Pro Asp Lys Glu Asp Glu Ser Gly Leu Thr
    130                 135                 140

Ile Ile His Leu Asp Ser Leu Gly Leu His Pro Arg Asn Leu Ile Phe
145                 150                 155                 160

Asn Asn Val Lys Arg Phe Leu Arg Glu Glu Trp Asn Tyr Leu Asn Gln
                165                 170                 175

Asp Ala Pro Leu Asp Leu Pro Ile Ser Ala Lys Val Trp Arg Asp Leu
            180                 185                 190
```

```
Pro Asn Met Ile Asn Glu Ala Glu Val Gln Val Pro Gln Gln Lys Asn
        195                 200                 205

Asp Phe Asp Cys Gly Leu Phe Leu Leu Phe Phe Ile Arg Arg Phe Ile
    210                 215                 220

Glu Glu Ala Pro Gln Arg Leu Thr Leu Gln Asp Leu Lys Met Ile His
225                 230                 235                 240

Lys Lys Trp Phe Lys Pro Glu Glu Ala Ser Ala Leu Arg Ile Lys Ile
                245                 250                 255

Trp Asn Ile Leu Val Asp Leu Phe Arg Lys Gly Asn Gln Thr Asp Leu
            260                 265                 270

Glu His His His His His His
        275
```

<210> SEQ ID NO 48
<211> LENGTH: 837
<212> TYPE: DNA
<213> ORGANISM: Artificial Sequence
<220> FEATURE:
<223> OTHER INFORMATION: Nucleotide sequence of C-terminally His-tagged
      Arabidopsis thalania ULP1c partial gene as it appears in
      pET24-AtULP1c

<400> SEQUENCE: 48

```
atggtagtag aggaagcatg tgaacttcct gaagggttac cagaagatat ttactaccca      60
tcaagtgatc aaagtgatgg gcgagacctt gttcaagtat ctcttaaaga tctgaaatgc     120
ctttcacctg gggaatatct acatcgcca gttataaatt tctacatcag gtacgtgcaa     180
catcacgtgt tttcagctga taagactgct gctaattgtc atttcttcaa tacgttttc     240 tacaagaagc tcacagaagc tgtttcatac aagggtaatg acagggatgc atattttgtg     300
aagttcaggc ggtggtggaa gggttttgat ctattctgta atcatatat atttatacca     360 atacatgaag atcttcactg gagcttagtc ataatttgca tcccagacaa ggaggacgaa     420
tcgggattga ctataattca cttggattca ttgggacttc acccaagaaa tttgattttc     480
aataatgtca aaagatttct gagagaggaa tggaactatc taaatcaaga tgctccattg     540
gatttaccaa tttcagcaaa agtatggaga gaccttccca atatgatcaa cgaagctgaa     600
gtgcaggttc cacaacagaa gaacgatttc gactgtggtc tgtttctgct cttcttcata     660
agacgtttca tcgaagaggc tcctcaaagg ctgacattgc aggatttgaa aatgattcac     720
aagaagtggt ttaaaccgga agaagcttcc gctttgagga tcaaaatctg aacatactc     780 gttgatctat ccgcaaggg taaccaaaca gatctcgagc accaccaca ccaccac       837
```

<210> SEQ ID NO 49
<211> LENGTH: 229
<212> TYPE: PRT
<213> ORGANISM: Artificial Sequence
<220> FEATURE:
<223> OTHER INFORMATION: Amino acid sequence of C-terminally His-tagged
      yeast (Saccharomyces cerevisiae) Ulp1 catalytic domain as it is
      encoded in pET24-yUlp1

<400> SEQUENCE: 49

```
Met Gly Leu Val Pro Glu Leu Asn Glu Lys Asp Asp Gln Val Gln
1               5                   10                  15

Lys Ala Leu Ala Ser Arg Glu Asn Thr Gln Leu Met Asn Arg Asp Asn
                20                  25                  30

Ile Glu Ile Thr Val Arg Asp Phe Lys Thr Leu Ala Pro Arg Arg Trp
            35                  40                  45

Leu Asn Asp Thr Ile Ile Glu Phe Phe Met Lys Tyr Ile Glu Lys Ser
```

```
                50                    55                    60
Thr Pro Asn Thr Val Ala Phe Asn Ser Phe Phe Tyr Thr Asn Leu Ser
 65                  70                      75                  80

Glu Arg Gly Tyr Gln Gly Val Arg Arg Trp Met Lys Arg Lys Lys Thr
                     85                      90                  95

Gln Ile Asp Lys Leu Asp Lys Ile Phe Thr Pro Ile Asn Leu Asn Gln
                    100                     105                 110

Ser His Trp Ala Leu Gly Ile Ile Asp Leu Lys Lys Thr Ile Gly
                    115                     120                 125

Tyr Val Asp Ser Leu Ser Asn Gly Pro Asn Ala Met Ser Phe Ala Ile
            130                     135                 140

Leu Thr Asp Leu Gln Lys Tyr Val Met Glu Glu Ser Lys His Thr Ile
145                     150                     155                 160

Gly Glu Asp Phe Asp Leu Ile His Leu Asp Cys Pro Gln Gln Pro Asn
                    165                     170                 175

Gly Tyr Asp Cys Gly Ile Tyr Val Cys Met Asn Thr Leu Tyr Gly Ser
                180                     185                 190

Ala Asp Ala Pro Leu Asp Phe Asp Tyr Lys Asp Ala Ile Arg Met Arg
                    195                     200             205

Arg Phe Ile Ala His Leu Ile Leu Thr Asp Ala Leu Lys Leu Glu His
        210                     215                 220

His His His His
225

<210> SEQ ID NO 50
<211> LENGTH: 687
<212> TYPE: DNA
<213> ORGANISM: Artificial Sequence
<220> FEATURE:
<223> OTHER INFORMATION: Nucleotide sequence of C-terminally His-tagged
      yeast Ulp1 partial gene as it appears in pET24-yUlp1

<400> SEQUENCE: 50
atgggacttg ttcctgaatt aaatgaaaaa gacgatgacc aagtacaaaa agctttggca      60
tctagagaaa atactcagtt aatgaataga gataatatag agataacagt acgtgatttt     120
aagaccttgg caccacgaag atggctaaat gacactatca ttgagttttt tatgaaatac     180
attgaaaaat ctaccccta tacagtggcg tttaattcat ttttctatac caatttatca     240 gaaagggggtt atcaaggcgt ccggaggtgg atgaagagaa agaagacaca aattgataaa     300
cttgataaaa tctttacacc aataaatttg aaccaatccc actgggcgtt gggcataatt     360
gatttaaaaa agaaaactat aggttacgta gattcattat cgaatggtcc aaatgctatg     420
agtttcgcta tactgactga cttgcaaaaa tatgttatgg aggaaagtaa gcatacaata     480
ggagaagact tgatttgat tcatttagat tgtccgcagc aaccaaatgg ctacgactgt     540
ggaatatatg tttgtatgaa tactctctat ggaagtgcag atgcgccatt ggattttgat     600
tataaagatg cgattaggat gagaagattt attgcccatt tgattttaac cgacgcttta     660
aaactcgagc accaccacca ccaccac                                          687

<210> SEQ ID NO 51
<211> LENGTH: 491
<212> TYPE: PRT
<213> ORGANISM: Artificial Sequence
<220> FEATURE:
<223> OTHER INFORMATION: Amino acid sequence of GST protein
      (glutathione-S-transferase) fused to the catalytic domain of
      Xanthomonas campestris pathovar vesicatoria XopD, encoded by the
      plasmid pGEX-5x-3-XopD(283-545)
```

<400> SEQUENCE: 51

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ile Glu Gly
    210                 215                 220

Arg Gly Ile Pro Glu Phe Asp Leu Asn Ile Pro Gln Gln Glu Glu Tyr
225                 230                 235                 240

Pro Asn Asn His Gly Thr Gln Thr Pro Met Gly Tyr Ser Ala Met Thr
                245                 250                 255

Pro Glu Arg Ile Asp Val Asp Asn Leu Pro Ser Pro Gln Asp Val Ala
            260                 265                 270

Asp Pro Glu Leu Pro Pro Val Arg Ala Thr Ser Trp Leu Leu Asp Gly
        275                 280                 285

His Leu Arg Ala Tyr Thr Asp Asp Leu Ala Arg Arg Leu Arg Gly Glu
    290                 295                 300

Pro Asn Ala His Leu Leu His Phe Ala Asp Ser Gln Val Val Thr Met
305                 310                 315                 320

Leu Ser Ser Ala Asp Pro Asp Gln Gln Ala Arg Ala Gln Arg Leu Leu
                325                 330                 335

Ala Gly Asp Asp Ile Pro Pro Ile Val Phe Leu Pro Ile Asn Gln Pro
            340                 345                 350

Asn Ala His Trp Ser Leu Leu Val Val Asp Arg Arg Asn Lys Asp Ala
        355                 360                 365

Val Ala Ala Tyr His Tyr Asp Ser Met Ala Gln Lys Asp Pro Gln Gln
    370                 375                 380

Arg Tyr Leu Ala Asp Met Ala Ala Tyr His Leu Gly Leu Asp Tyr Gln
385                 390                 395                 400

Gln Thr His Glu Met Pro Ile Ala Ile Gln Ser Asp Gly Tyr Ser Cys
                405                 410                 415
```

Gly Asp His Val Leu Thr Gly Ile Glu Val Leu Ala His Arg Val Leu
            420                 425                 430

Asp Gly Thr Phe Asp Tyr Ala Gly Gly Arg Asp Leu Thr Asp Ile Glu
        435                 440                 445

Pro Asp Arg Gly Leu Ile Arg Asp Arg Leu Ala Gln Ala Glu Gln Ala
    450                 455                 460

Pro Ala Glu Ser Ser Ile Arg Gln Val Pro Ala Arg Ser Asn Glu Gln
465                 470                 475                 480

Lys Lys Lys Lys Ser Lys Trp Trp Lys Phe
                485                 490

<210> SEQ ID NO 52
<211> LENGTH: 1473
<212> TYPE: DNA
<213> ORGANISM: Artificial Sequence
<220> FEATURE:
<223> OTHER INFORMATION: Nucleotide sequence of GST-XopD gene fusion

<400> SEQUENCE: 52

| | | | | | |
|---|---|---|---|---|---|
| atgtcccta | tactaggtta | ttggaaaatt | aagggccttg | tgcaacccac | tcgacttctt | 60 |
| ttggaatatc | ttgaagaaaa | atatgaagag | catttgtatg | agcgcgatga | aggtgataaa | 120 |
| tggcgaaaca | aaaagtttga | attgggtttg | gagtttccca | atcttcctta | ttatattgat | 180 |
| ggtgatgtta | aattaacaca | gtctatggcc | atcatacgtt | atatagctga | caagcacaac | 240 |
| atgttgggtg | gttgtccaaa | agagcgtgca | gagatttcaa | tgcttgaagg | agcggttttg | 300 |
| gatattagat | acggtgtttc | gagaattgca | tatagtaaag | actttgaaac | tctcaaagtt | 360 |
| gattttctta | gcaagctacc | tgaaatgctg | aaaatgttcg | aagatcgttt | atgtcataaa | 420 |
| acatatttaa | atggtgatca | tgtaacccat | cctgacttca | tgttgtatga | cgctcttgat | 480 |
| gttgttttat | acatggaccc | aatgtgcctg | gatgcgttcc | caaaattagt | ttgttttaaa | 540 |
| aaacgtattg | aagctatccc | acaaattgat | aagtacttga | atccagcaa | gtatatagca | 600 |
| tggcctttgc | agggctggca | agccacgttt | ggtggtggcg | accatcctcc | aaaatcggat | 660 |
| ctgatcgaag | tcgtgggat | ccccgaattc | gacctcaaca | tcccccagca | agaagagtac | 720 |
| cctaataacc | atggcacgca | gaccccccatg | ggatattcgg | ccatgactcc | tgaaaggatc | 780 |
| gatgtggaca | atctgccgtc | gccccaggac | gtcgcagacc | cgaacttcc | tccagtgagg | 840 |
| gccacttcgt | ggctgctgga | tggacatttg | cgcgcctaca | ccgatgacct | agctcgccga | 900 |
| ttgcgagggg | agcccaacgc | ccatttactc | cactttgccg | actcgcaggt | agtgaccatg | 960 |
| ctgagctccg | cagatccaga | ccaacaggcc | cgcgcacagc | gccttcttgc | cggagacgac | 1020 |
| atcccaccta | tcgtgttcct | gccgatcaat | cagcccaacg | ctcattggtc | attgctcgtc | 1080 |
| gtcgaccggc | gtaacaagga | cgctgttgcg | gcctaccact | atgattccat | ggcacagaag | 1140 |
| gacccacagc | aacgctacct | tgctgatatg | cggcctatc | accttggcct | tgattatcaa | 1200 |
| caaactcatg | aaatgcccat | cgcgatacag | tcggacggtt | attcctgcgg | cgatcatgtg | 1260 |
| ctgaccggga | tagaggtgtt | ggcccacagg | gtactcgacg | gcaccttcga | ctacgcaggc | 1320 |
| ggcagggacc | tgactgatat | cgaaccagac | cgcggcctca | tcagggatcg | tcttgcccaa | 1380 |
| gcggagcaag | ctccagcaga | aagcagcatc | aggcaagttc | ccgcacgatc | caacgaacag | 1440 |
| aagaaaaaga | aaagcaagtg | gtggaaaaag | ttc | | | 1473 |

<210> SEQ ID NO 53
<211> LENGTH: 51
<212> TYPE: DNA

<213> ORGANISM: Artificial Sequence
<220> FEATURE:
<223> OTHER INFORMATION: 5' primer for generation of a human SUMO-1 PCR
      product to create the amino-terminal 6xHis-tagged SUMO fusion
      vectors.

<400> SEQUENCE: 53 tttttttccat gggtcatcac catcatcatc actctgacca ggaggcaaaa c         51

<210> SEQ ID NO 54
<211> LENGTH: 43
<212> TYPE: DNA
<213> ORGANISM: Artificial Sequence
<220> FEATURE:
<223> OTHER INFORMATION: 3' primer for generation of a human SUMO-1 PCR
      product to create the amino-terminal 6xHis-tagged SUMO fusion
      vectors.

<400> SEQUENCE: 54 tttttttggat ccggtctcaa cctcccgttt gttcctgata aac                  43

<210> SEQ ID NO 55
<211> LENGTH: 50
<212> TYPE: DNA
<213> ORGANISM: Artificial Sequence
<220> FEATURE:
<223> OTHER INFORMATION: For Saccharomyces cerevisiae Smt3, a PCR
      product was generated with the primers (SEQ ID NO: 55) and (SEQ ID
      NO: 56) using a modified SUMO (Smt3) gene as a template.

<400> SEQUENCE: 55
ccatgggtca tcaccatcat catcacgggt cggactcaga agtcaatcaa             50

<210> SEQ ID NO 56
<211> LENGTH: 36
<212> TYPE: DNA
<213> ORGANISM: Artificial Sequence
<220> FEATURE:
<223> OTHER INFORMATION: For Saccharomyces cerevisiae Smt3, a PCR
      product was generated with the primers (SEQ ID NO: 55) and (SEQ ID
      NO: 56) using a modified SUMO (Smt3) gene as a template.

<400> SEQUENCE: 56
ggatccggtc tcaacctcca atctgttcgc ggtgag                           36

<210> SEQ ID NO 57
<211> LENGTH: 33
<212> TYPE: DNA
<213> ORGANISM: Artificial Sequence
<220> FEATURE:
<223> OTHER INFORMATION: To make 6xHis-SUMO-1 and 6xHis-Smt3 fusions
      with eGFP, the eGFP sequence (46) was amplified with the primers
      (SEQ ID NO: 57) and (SEQ ID NO: 58).

<400> SEQUENCE: 57
ggtctcaagg tatggtgagc aagggcgagg agc                              33

<210> SEQ ID NO 58
<211> LENGTH: 31
<212> TYPE: DNA
<213> ORGANISM: Artificial Sequence
<220> FEATURE:
<223> OTHER INFORMATION: To make 6xHis-SUMO-1 and 6xHis-Smt3 fusions
      with eGFP, the eGFP sequence (46) was amplified with the primers
      (SEQ ID NO: 57) and (SEQ ID NO: 58).

<400> SEQUENCE: 58
aagcttatta cttgtacagc tcgtccatgc c                                31

<210> SEQ ID NO 59
<211> LENGTH: 41
<212> TYPE: DNA
<213> ORGANISM: Artificial Sequence
<220> FEATURE:
<223> OTHER INFORMATION: For human SUMO-3, a PCR product was generated
      with the primers (SEQ ID NO: 59) and (SEQ ID NO: 60) using
      SUMO-3-containing MGC cDNA clone #3505840 (Open Biosystems).

<400> SEQUENCE: 59
gatcgaacct gcatataggt atgtccgagg agaagcccaa g         41

<210> SEQ ID NO 60
<211> LENGTH: 42
<212> TYPE: DNA
<213> ORGANISM: Artificial Sequence
<220> FEATURE:
<223> OTHER INFORMATION: For human SUMO-3, a PCR product was generated
      with the primers (SEQ ID NO: 59) and (SEQ ID NO: 60) using
      SUMO-3-containing MGC cDNA clone #3505840 (Open Biosystems).

<400> SEQUENCE: 60
gatcggatcc ggtctcaacc tcccgtctgc tgctggaaca cg        42

<210> SEQ ID NO 61
<211> LENGTH: 40
<212> TYPE: DNA
<213> ORGANISM: Artificial Sequence
<220> FEATURE:
<223> OTHER INFORMATION: For Arabidopsis thalania SUMO1, a PCR product
      was generated with the primers (SEQ ID NO: 61) and (SEQ ID NO: 62)
      using cDNA clone U17495 from the Arabidopsis Biological Resource
      Center.

<400> SEQUENCE: 61
gatcgaacct gcatataggt atgtctgcaa accaggagga         40

<210> SEQ ID NO 62
<211> LENGTH: 41
<212> TYPE: DNA
<213> ORGANISM: Artificial Sequence
<220> FEATURE:
<223> OTHER INFORMATION: For Arabidopsis thalania SUMO1, a PCR product
      was generated with the primers (SEQ ID NO: 61) and (SEQ ID NO: 62)
      using cDNA clone U17495 from the Arabidopsis Biological Resource
      Center.

<400> SEQUENCE: 62
gatcggatcc ggtctcaacc tccagtctga tggagcatcg c        41

<210> SEQ ID NO 63
<211> LENGTH: 39
<212> TYPE: DNA
<213> ORGANISM: Artificial Sequence
<220> FEATURE:
<223> OTHER INFORMATION: For Arabidopsis thalania SUMO2, a PCR product
      was generated with the primers (SEQ ID NO: 63) and (SEQ ID NO: 64)
      using cDNA clone U21609 from the Arabidopsis Biological Resource
      Center.

<400> SEQUENCE: 63
gatcgacgtc tcaaggtatg tctgctactc cggaagaag         39

<210> SEQ ID NO 64
<211> LENGTH: 42
<212> TYPE: DNA
<213> ORGANISM: Artificial Sequence
<220> FEATURE:
<223> OTHER INFORMATION: For Arabidopsis thalania SUMO2, a PCR product -continued was generated with the primers (SEQ ID NO: 63) and (SEQ ID NO: 64)
using cDNA clone U21609 from the Arabidopsis Biological Resource
Center.

<400> SEQUENCE: 64
gatcggatcc ggtctcaacc tccagtctga tgaagcattg ca                42

<210> SEQ ID NO 65
<211> LENGTH: 41
<212> TYPE: DNA
<213> ORGANISM: Artificial Sequence
<220> FEATURE:
<223> OTHER INFORMATION: For tomato T-SUMO, a PCR product was generated
      with the primers (SEQ ID NO: 65) and (SEQ ID NO: 66) a T-SUMO
      plasmid kindly provided by M. B. Mudgett.

<400> SEQUENCE: 65
gatcgaacct gcatataggt atgtctgcta gcggcggcac c                 41

<210> SEQ ID NO 66
<211> LENGTH: 40
<212> TYPE: DNA
<213> ORGANISM: Artificial Sequence
<220> FEATURE:
<223> OTHER INFORMATION: For tomato T-SUMO, a PCR product was generated
      with the primers (SEQ ID NO: 65) and (SEQ ID NO: 66) a T-SUMO
      plasmid kindly provided by M. B. Mudgett.

<400> SEQUENCE: 66
gatcggatcc ggtctcaacc tccagtttga tgtagcattg                   40

<210> SEQ ID NO 67
<211> LENGTH: 45
<212> TYPE: DNA
<213> ORGANISM: Artificial Sequence
<220> FEATURE:
<223> OTHER INFORMATION: The eGFP sequence was amplified with the
      primers (SEQ ID NO: 67) and (SEQ ID NO: 68).

<400> SEQUENCE: 67 tttttttggtc tcaaggtatg gtgagcaagg gcgagggcga ggagc            45

<210> SEQ ID NO 68
<211> LENGTH: 34
<212> TYPE: DNA
<213> ORGANISM: Artificial Sequence
<220> FEATURE:
<223> OTHER INFORMATION: The eGFP sequence was amplified with the
      primers (SEQ ID NO: 67) and (SEQ ID NO: 68).

<400> SEQUENCE: 68 tttttttctcg agttacttgt acagctcgtc catg                        34

<210> SEQ ID NO 69
<211> LENGTH: 340
<212> TYPE: PRT
<213> ORGANISM: Artificial Sequence
<220> FEATURE:
<223> OTHER INFORMATION: Amino acid sequence of N-terminally His-tagged
      human SUMO-3-eGFP protein as it is encoded in
      pET24-6xHis-SUMO-3-eGFP

<400> SEQUENCE: 69

Met Gly His His His His His His Gly Gly Ser Glu Glu Lys Pro Lys
1               5                   10                  15

Glu Gly Val Lys Thr Glu Asn Asp His Ile Asn Leu Lys Val Ala Gly
            20                  25                  30

Gln Asp Gly Ser Val Val Gln Phe Lys Ile Lys Arg His Thr Pro Leu
            35                  40                  45

Ser Lys Leu Met Lys Ala Tyr Cys Glu Arg Gln Gly Leu Ser Met Arg
 50                  55                  60

Gln Ile Arg Phe Arg Phe Asp Gly Gln Pro Ile Asn Glu Thr Asp Thr
 65                  70                  75                  80

Pro Ala Gln Leu Glu Met Glu Asp Glu Asp Thr Ile Asp Val Phe Gln
                 85                  90                  95

Gln Gln Thr Gly Gly Met Val Ser Lys Gly Glu Glu Leu Phe Thr Gly
            100                 105                 110

Val Val Pro Ile Leu Val Glu Leu Asp Gly Asp Val Asn Gly His Lys
            115                 120                 125

Phe Ser Val Ser Gly Glu Gly Glu Gly Asp Ala Thr Tyr Gly Lys Leu
130                 135                 140

Thr Leu Lys Phe Ile Cys Thr Thr Gly Lys Leu Pro Val Pro Trp Pro
145                 150                 155                 160

Thr Leu Val Thr Thr Leu Thr Tyr Gly Val Gln Cys Phe Ser Arg Tyr
                165                 170                 175

Pro Asp His Met Lys Gln His Asp Phe Phe Lys Ser Ala Met Pro Glu
                180                 185                 190

Gly Tyr Val Gln Glu Arg Thr Ile Phe Phe Lys Asp Asp Gly Asn Tyr
            195                 200                 205

Lys Thr Arg Ala Glu Val Lys Phe Glu Gly Asp Thr Leu Val Asn Arg
210                 215                 220

Ile Glu Leu Lys Gly Ile Asp Phe Lys Glu Asp Gly Asn Ile Leu Gly
225                 230                 235                 240

His Lys Leu Glu Tyr Asn Tyr Asn Ser His Asn Val Tyr Ile Met Ala
                245                 250                 255

Asp Lys Gln Lys Asn Gly Ile Lys Val Asn Phe Lys Ile Arg His Asn
                260                 265                 270

Ile Glu Asp Gly Ser Val Gln Leu Ala Asp His Tyr Gln Gln Asn Thr
            275                 280                 285

Pro Ile Gly Asp Gly Pro Val Leu Leu Pro Asp Asn His Tyr Leu Ser
290                 295                 300

Thr Gln Ser Ala Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Lys
            340

```
<210> SEQ ID NO 70
<211> LENGTH: 1023
<212> TYPE: DNA
<213> ORGANISM: Artificial Sequence
<220> FEATURE:
<223> OTHER INFORMATION: Nucleotide sequence of N-terminally His-tagged
      human SUMO-3 -eGFP gene as it appears in pET24-6xHis-SUMO-3-eGFP

<400> SEQUENCE: 70
atgggtcatc accatcatca tcacggaggt tccgaggaga agcccaagga gggtgtgaag      60
acagagaatg accacatcaa cctgaaggtg gccgggcagg acggctccgt ggtgcagttc     120
aagatcaaga ggcacacgcc gctgagcaag ctgatgaagg cctactgcga gaggcagggc     180
ttgtcaatga ggcagatcag attcaggttc gacgggcagc caatcaatga aactgacact     240
ccagcacagc tggagatgga ggacgaggac accatcgacg tgttccagca gcagacggga     300
```

```
ggtatggtga gcaagggcga ggagctgttc accggggtgg tgcccatcct ggtcgagctg     360
gacggcgacg taaacggcca caagttcagc gtgtccggcg agggcgaggg cgatgccacc     420
tacggcaagc tgaccctgaa gttcatctgc accaccggca agctgcccgt gccctggccc     480
accctcgtga ccaccctgac ctacggcgtg cagtgcttca gccgctaccc cgaccacatg     540
aagcagcacg acttcttcaa gtccgccatg cccgaaggct acgtccagga gcgcaccatc     600
ttcttcaagg acgacggcaa ctacaagacc cgcgccgagg tgaagttcga gggcgacacc     660
ctggtgaacc gcatcgagct gaagggcatc gacttcaagg aggacggcaa catcctgggg     720
cacaagctgg agtacaacta caacagccac aacgtctata tcatggccga caagcagaag     780
aacggcatca aggtgaactt caagatccgc cacaacatcg aggacggcag cgtgcagctc     840
gccgaccact accagcagaa cacccccatc ggcgacggcc ccgtgctgct gcccgacaac     900
cactacctga gcacccagtc cgccctgagc aaagacccca acgagaagcg cgatcacatg     960
gtcctgctgg agttcgtgac cgccgccggg atcactctcg gcatggacga gctgtacaag    1020
taa                                                                  1023
```

<210> SEQ ID NO 71
<211> LENGTH: 93
<212> TYPE: PRT
<213> ORGANISM: Homo Sapiens

<400> SEQUENCE: 71

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Lys Ala Tyr Cys
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly
                85                  90

<210> SEQ ID NO 72
<211> LENGTH: 93
<212> TYPE: PRT
<213> ORGANISM: Arabidopsis thaliana

<400> SEQUENCE: 72

Met Ser Asn Pro Gln Asp Asp Lys Pro Ile Asp Glu Gln Glu Ala
1               5                   10                  15

His Val Ile Leu Lys Val Lys Ser Gln Asp Gly Asp Glu Val Leu Phe
            20                  25                  30

Lys Asn Lys Lys Ser Ala Pro Leu Lys Lys Leu Met Tyr Val Tyr Cys
        35                  40                  45

Asp Arg Arg Gly Leu Lys Leu Asp Ala Phe Ala Phe Ile Phe Asn Gly
    50                  55                  60

Ala Arg Ile Gly Gly Leu Glu Thr Pro Asp Glu Leu Asp Met Glu Asp
65                  70                  75                  80

Gly Asp Val Ile Asp Ala Cys Arg Ala Met Ser Gly Gly
                85                  90

```
<210> SEQ ID NO 73
<211> LENGTH: 104
<212> TYPE: PRT
<213> ORGANISM: Arabidopsis thaliana

<400> SEQUENCE: 73

Met Ser Thr Thr Ser Arg Val Gly Ser Asn Glu Val Lys Met Glu Gly
1               5                   10                  15

Gln Lys Arg Lys Val Val Ser Asp Pro Thr His Val Thr Leu Lys Val
            20                  25                  30

Lys Gly Gln Asp Glu Glu Asp Phe Arg Val Phe Trp Val Arg Arg Asn
        35                  40                  45

Ala Lys Leu Leu Lys Met Met Glu Leu Tyr Thr Lys Met Arg Gly Ile
    50                  55                  60

Glu Trp Asn Thr Phe Arg Phe Leu Phe Asp Gly Ser Arg Ile Arg Glu
65                  70                  75                  80

Tyr His Thr Pro Asp Glu Leu Glu Arg Lys Asp Gly Asp Glu Ile Asp
                85                  90                  95

Ala Met Leu Cys Gln Gln Ser Gly
            100

<210> SEQ ID NO 74
<211> LENGTH: 103
<212> TYPE: PRT
<213> ORGANISM: Arabidopsis thaliana

<400> SEQUENCE: 74

Met Val Ser Ser Thr Asp Thr Ile Ser Ala Ser Phe Val Ser Lys Lys
1               5                   10                  15

Ser Arg Ser Pro Glu Thr Ser Pro His Met Lys Val Thr Leu Lys Val
            20                  25                  30

Lys Asn Gln Gln Gly Ala Glu Asp Leu Tyr Lys Ile Gly Thr His Ala
        35                  40                  45

His Leu Lys Lys Leu Met Ser Ala Tyr Cys Thr Lys Arg Asn Leu Asp
    50                  55                  60

Tyr Ser Val Arg Phe Val Tyr Asn Gly Arg Glu Ile Lys Ala Arg
65                  70                  75                  80

Gln Thr Pro Ala Gln Leu His Met Glu Glu Glu Asp Glu Ile Cys Met
                85                  90                  95

Val Met Glu Leu Gly Gly Gly
            100

<210> SEQ ID NO 75
<211> LENGTH: 108
<212> TYPE: PRT
<213> ORGANISM: Arabidopsis thaliana

<400> SEQUENCE: 75

Met Ser Thr Lys Ser Ser Ser Ile His Gly Arg Asn Glu Val Lys Met
1               5                   10                  15

Glu Gly Glu Lys Arg Lys Asp Val Glu Ser Glu Ser Thr His Val Thr
            20                  25                  30

Leu Asn Val Lys Gly Gln Asp Glu Glu Gly Val Lys Val Phe Arg Val
        35                  40                  45

Arg Arg Lys Ala Arg Leu Leu Lys Leu Met Glu Tyr Ala Lys Met
    50                  55                  60

Arg Gly Ile Glu Trp Asn Thr Phe Arg Phe Leu Ser Asp Asp Gly Ser
65                  70                  75                  80
```

```
Arg Ile Arg Glu Tyr His Thr Ala Asp Asp Met Glu Leu Lys Asp Gly
                85                  90                  95
Asp Gln Ile Asp Ala Leu Leu Pro Gln Glu Ser Gly
            100                 105

<210> SEQ ID NO 76
<211> LENGTH: 90
<212> TYPE: PRT
<213> ORGANISM: Arabidopsis thaliana

<400> SEQUENCE: 76

Met Ser Ala Ala Asp Lys Lys Pro Leu Ile Pro Ser His Ile Thr
1               5                   10                  15
Ile Lys Ile Lys Ser Gln Asp Asp Ile Cys Val Tyr Phe Arg Ile Lys
                20                  25                  30
Arg Asp Val Glu Leu Arg Thr Met Met Gln Ala Tyr Ser Asp Lys Val
            35                  40                  45
Gly Gln Gln Met Ser Ala Phe Arg Phe His Cys Asp Gly Ile Arg Ile
        50                  55                  60
Lys Pro Asn Gln Thr Pro Asn Glu Leu Asp Leu Glu Asp Gly Asp Glu
65                  70                  75                  80
Ile Asp Ala Phe Val Asp Gln Ile Ala Gly
                85                  90

<210> SEQ ID NO 77
<211> LENGTH: 93
<212> TYPE: PRT
<213> ORGANISM: Arabidopsis thaliana

<400> SEQUENCE: 77

Met Ser Ser Ser Asp Lys Lys Pro Leu Ile Pro Ser Ser His Ile Thr
1               5                   10                  15
Val Lys Val Lys Asn Gln Asp Asp Ile Cys Val Tyr Phe Arg Ile Lys
                20                  25                  30
Arg Asp Val Glu Leu Arg Lys Met Met His Ala Tyr Ser Asp Lys Val
            35                  40                  45
Gly Val Glu Met Lys Thr Leu Arg Phe Leu Phe Asp Gly Asn Arg Ile
        50                  55                  60
Lys Leu Asn Gln Thr Pro Asn Glu Val Phe Gln Leu Gly Leu Glu Asp
65                  70                  75                  80
Glu Asp Glu Ile Glu Ala Gly Gly Glu Gln Leu Gly Gly
                85                  90

<210> SEQ ID NO 78
<211> LENGTH: 98
<212> TYPE: PRT
<213> ORGANISM: Xenopus laevis

<400> SEQUENCE: 78

Met Ser Asp Gln Glu Ala Lys Pro Ser Ser Glu Asp Leu Gly Asp Lys
1               5                   10                  15
Lys Asp Gly Gly Asp Tyr Ile Lys Leu Lys Val Ile Gly Gln Asp Ser
                20                  25                  30
Ser Glu Ile His Phe Lys Val Lys Met Thr Thr His Leu Lys Lys Leu
            35                  40                  45
Lys Glu Ser Tyr Arg Gln Arg Gln Gly Val Pro Met Asn Ser Leu Arg
        50                  55                  60
Phe Leu Phe Glu Gly Gln Arg Ile Ser Asp His Gln Thr Pro Lys Glu
65                  70                  75                  80
```

```
Leu Gly Met Glu Glu Glu Asp Val Ile Glu Val Tyr Gln Gln Thr
                85                  90                  95

Gly Gly

<210> SEQ ID NO 79
<211> LENGTH: 93
<212> TYPE: PRT
<213> ORGANISM: Xenopus laevis

<400> SEQUENCE: 79

Met Ala Asp Asp Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
                20                  25                  30

Lys Ile Lys Arg Gln Thr Pro Leu Ser Lys Leu Met Lys Ala Tyr Cys
            35                  40                  45

Glu Arg Gln Gly Leu Ser Met Arg Gln Ile Arg Phe Arg Phe Asp Gly
        50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Thr Gly Gly
                85                  90

<210> SEQ ID NO 80
<211> LENGTH: 92
<212> TYPE: PRT
<213> ORGANISM: Xenopus laevis

<400> SEQUENCE: 80

Met Ser Glu Glu Lys Pro Lys Glu Gly Val Lys Thr Glu Asn Asp His
1               5                   10                  15

Ile Asn Leu Lys Val Ala Gly Gln Asp Gly Ser Val Val Gln Phe Lys
                20                  25                  30

Ile Lys Arg His Thr Pro Leu Ser Lys Leu Met Lys Ala Tyr Cys Asp
            35                  40                  45

Arg Gln Gly Leu Ser Met Arg Gln Ile Arg Phe Arg Phe Asp Gly Gln
        50                  55                  60

Pro Ile Asn Glu Thr Asp Thr Pro Ala Gln Leu Glu Met Glu Asp Glu
65                  70                  75                  80

Asp Thr Ile Asp Val Phe Gln Gln Gln Thr Gly Gly
                85                  90

<210> SEQ ID NO 81
<211> LENGTH: 88
<212> TYPE: PRT
<213> ORGANISM: Drosophila melanogaster

<400> SEQUENCE: 81

Met Ser Asp Glu Lys Lys Gly Gly Glu Thr Glu His Ile Asn Leu Lys
1               5                   10                  15

Val Leu Gly Gln Asp Asn Ala Val Val Gln Phe Lys Ile Lys Lys His
                20                  25                  30

Thr Pro Leu Arg Lys Leu Met Asn Ala Tyr Cys Asp Arg Ala Gly Leu
            35                  40                  45

Ser Met Gln Val Val Arg Phe Arg Phe Asp Gly Gln Pro Ile Asn Glu
        50                  55                  60

Asn Asp Thr Pro Thr Ser Leu Glu Met Glu Glu Gly Asp Thr Ile Glu
65                  70                  75                  80
```

Val Tyr Gln Gln Gln Thr Gly Gly
                85

<210> SEQ ID NO 82
<211> LENGTH: 90
<212> TYPE: PRT
<213> ORGANISM: Caenorhabditis elegans

<400> SEQUENCE: 82

Met Ala Asp Asp Ala Ala Gln Ala Gly Asp Asn Ala Glu Tyr Ile Lys
1               5                   10                  15

Ile Lys Val Val Gly Gln Asp Ser Asn Glu Val His Phe Arg Val Lys
                20                  25                  30

Tyr Gly Thr Ser Met Ala Lys Leu Lys Lys Ser Tyr Ala Asp Arg Thr
            35                  40                  45

Gly Val Ala Val Asn Ser Leu Arg Phe Leu Phe Asp Gly Arg Arg Ile
        50                  55                  60

Asn Asp Asp Asp Thr Pro Lys Thr Leu Glu Met Glu Asp Asp Asp Val
65                  70                  75                  80

Ile Glu Val Tyr Gln Glu Gln Leu Gly Gly
                85                  90

<210> SEQ ID NO 83
<211> LENGTH: 111
<212> TYPE: PRT
<213> ORGANISM: Schizosacharomyces pombe

<400> SEQUENCE: 83

Met Ser Glu Ser Pro Ser Ala Asn Ile Ser Asp Ala Asp Lys Ser Ala
1               5                   10                  15

Ile Thr Pro Thr Thr Gly Asp Thr Ser Gln Gln Asp Val Lys Pro Ser
                20                  25                  30

Thr Glu His Ile Asn Leu Lys Val Val Gly Gln Asp Asn Asn Glu Val
            35                  40                  45

Phe Phe Lys Ile Lys Lys Thr Thr Glu Phe Ser Lys Leu Met Lys Ile
        50                  55                  60

Tyr Cys Ala Arg Gln Gly Lys Ser Met Asn Ser Leu Arg Phe Leu Val
65                  70                  75                  80

Asp Gly Glu Arg Ile Arg Pro Asp Gln Thr Pro Ala Glu Leu Asp Met
                85                  90                  95

Glu Asp Gly Asp Gln Ile Glu Ala Val Leu Glu Gln Leu Gly Gly
            100                 105                 110

<210> SEQ ID NO 84
<211> LENGTH: 98
<212> TYPE: PRT
<213> ORGANISM: Plasmodium falciparum

<400> SEQUENCE: 84

Met Gly Asp Asp Ser Ala Val Asn Asn Gly Ser Ser Pro Val
1               5                   10                  15

Asn Asn Gln Gly Glu His Ile Gln Val Lys Val Arg Ser Pro Asp Gly
                20                  25                  30

Ala Glu Val Phe Phe Lys Ile Lys Arg Lys Thr Lys Leu Glu Lys Leu
            35                  40                  45

Met Glu Val Tyr Cys Asn Arg Leu Gly Gln Ser Met Glu Ala Val Arg
        50                  55                  60

Phe Leu Tyr Asp Gly Asp Arg Ile His Gly Asp Asn Thr Pro Glu Gln

```
                65                  70                  75                  80
Leu Gly Ile Glu Asp Gly Asp Val Ile Asp Ala Met Val Gln Gln Thr
                    85                  90                  95
Gly Gly

<210> SEQ ID NO 85
<211> LENGTH: 92
<212> TYPE: PRT
<213> ORGANISM: Aspergillus nidulans

<400> SEQUENCE: 85

Met Ser Asp Pro Ser Ala Pro Thr Pro Glu Ala Pro Ala Pro Val Glu
1               5                   10                  15

His Leu Asn Ile Lys Val Thr Asp Asn Asn Asn Glu Val Phe Phe Lys
                20                  25                  30

Ile Lys Arg Thr Thr Thr Leu Lys Lys Leu Met Asp Ala Phe Cys Asp
                35                  40                  45

Arg Gln Gly Lys Gln Pro Ser Thr Val Arg Phe Leu Phe Asp Gly Thr
        50                  55                  60

Arg Val Arg Pro Glu Asp Thr Pro Asp Thr Leu Asp Met Ala Asp Gly
65                  70                  75                  80

Asp Thr Leu Glu Val His Gln Glu Gln Ile Gly Gly
                85                  90

<210> SEQ ID NO 86
<211> LENGTH: 219
<212> TYPE: PRT
<213> ORGANISM: Saccharomyces cerevisiae

<400> SEQUENCE: 86

Leu Val Pro Glu Leu Asn Glu Lys Asp Asp Gln Val Gln Lys Ala
1               5                   10                  15

Leu Ala Ser Arg Glu Asn Thr Gln Leu Met Asn Arg Asp Asn Ile Glu
                20                  25                  30

Ile Thr Val Arg Asp Phe Lys Thr Leu Ala Pro Arg Arg Trp Leu Asn
                35                  40                  45

Asp Thr Ile Ile Glu Phe Phe Met Lys Tyr Ile Glu Lys Ser Thr Pro
    50                  55                  60

Asn Thr Val Ala Phe Asn Ser Phe Phe Tyr Thr Asn Leu Ser Glu Arg
65                  70                  75                  80

Gly Tyr Gln Gly Val Arg Arg Trp Met Lys Arg Lys Lys Thr Gln Ile
                85                  90                  95

Asp Lys Leu Asp Lys Ile Phe Thr Pro Ile Asn Leu Asn Gln Ser His
                100                 105                 110

Trp Ala Leu Gly Ile Ile Asp Leu Lys Lys Lys Thr Ile Gly Tyr Val
                115                 120                 125

Asp Ser Leu Ser Asn Gly Pro Asn Ala Met Ser Phe Ala Ile Leu Thr
            130                 135                 140

Asp Leu Gln Lys Tyr Val Met Glu Glu Ser Lys His Thr Ile Gly Glu
145                 150                 155                 160

Asp Phe Asp Leu Ile His Leu Asp Cys Pro Gln Gln Pro Asn Gly Tyr
                165                 170                 175

Asp Cys Gly Ile Tyr Val Cys Met Asn Thr Leu Tyr Gly Ser Ala Asp
                180                 185                 190

Ala Pro Leu Asp Phe Asp Tyr Lys Asp Ala Ile Arg Met Arg Arg Phe
            195                 200                 205
```

```
Ile Ala His Leu Ile Leu Thr Asp Ala Leu Lys
        210                 215
```

<210> SEQ ID NO 87
<211> LENGTH: 256
<212> TYPE: PRT
<213> ORGANISM: Saccharomyces cerevisiae

<400> SEQUENCE: 87

```
Asn Ser Glu Phe Asp Asp Ala Thr Thr Glu Phe Glu Thr Pro Glu Leu
1               5                   10                  15

Phe Lys Pro Ser Leu Cys Tyr Lys Phe Asn Asp Gly Ser Ser Tyr Thr
            20                  25                  30

Ile Thr Asn Gln Asp Phe Lys Cys Leu Phe Asn Lys Asp Trp Val Asn
        35                  40                  45

Asp Ser Ile Leu Asp Phe Phe Thr Lys Phe Tyr Ile Glu Ser Ser Ile
    50                  55                  60

Glu Lys Ser Ile Ile Lys Arg Glu Gln Val His Leu Met Ser Ser Phe
65                  70                  75                  80

Phe Tyr Thr Lys Leu Ile Ser Asn Pro Ala Asp Tyr Tyr Ser Asn Val
                85                  90                  95

Lys Lys Trp Val Asn Asn Thr Asp Leu Phe Ser Lys Lys Tyr Val Val
            100                 105                 110

Ile Pro Ile Asn Ile Ser Tyr His Trp Phe Ser Cys Ile Ile Thr Asn
        115                 120                 125

Leu Asp Ala Ile Leu Asp Phe His Gln Asn Lys Asp Lys Asn Asp Ala
    130                 135                 140

Ile Asn Ser Asp Glu Ile Ser Ile Asn Asn Pro Leu Val Asn Ile Leu
145                 150                 155                 160

Thr Phe Asp Ser Leu Arg Gln Thr His Ser Arg Glu Ile Asp Pro Ile
                165                 170                 175

Lys Glu Phe Leu Ile Ser Tyr Ala Leu Asp Lys Tyr Ser Ile Gln Leu
            180                 185                 190

Asp Lys Thr Gln Ile Lys Met Lys Thr Cys Pro Val Pro Gln Gln Pro
        195                 200                 205

Asn Met Ser Asp Cys Gly Val His Val Ile Leu Asn Ile Arg Lys Phe
    210                 215                 220

Phe Glu Asn Pro Val Glu Thr Ile Asp Val Trp Lys Asn Ser Lys Ile
225                 230                 235                 240

Lys Ser Lys His Phe Thr Ala Lys Met Ile Asn Lys Tyr Phe Asp Lys
                245                 250                 255
```

<210> SEQ ID NO 88
<211> LENGTH: 225
<212> TYPE: PRT
<213> ORGANISM: Homo sapiens

<400> SEQUENCE: 88

```
Phe Pro Glu Ile Thr Glu Glu Met Glu Lys Glu Ile Lys Asn Val Phe
1               5                   10                  15

Arg Asn Gly Asn Gln Asp Glu Val Leu Ser Glu Ala Phe Arg Leu Thr
            20                  25                  30

Ile Thr Arg Lys Asp Ile Gln Thr Leu Asn His Leu Asn Trp Leu Asn
        35                  40                  45

Asp Glu Ile Ile Asn Phe Tyr Met Asn Met Leu Met Glu Arg Ser Lys
    50                  55                  60

Glu Lys Gly Leu Pro Ser Val His Ala Phe Asn Thr Phe Phe Phe Thr
```

```
                65                  70                  75                  80
Lys Leu Lys Thr Ala Gly Tyr Gln Ala Val Lys Arg Trp Thr Lys Lys
                    85                  90                  95

Val Asp Val Phe Ser Val Asp Ile Leu Leu Val Pro Ile His Leu Gly
                    100                 105                 110

Val His Trp Cys Leu Ala Val Val Asp Phe Arg Lys Lys Asn Ile Thr
                    115                 120                 125

Tyr Tyr Asp Ser Met Gly Gly Ile Asn Asn Glu Ala Cys Arg Ile Leu
                    130                 135                 140

Leu Gln Tyr Leu Lys Gln Glu Ser Ile Asp Lys Lys Arg Lys Glu Phe
145                 150                 155                 160

Asp Thr Asn Gly Trp Gln Leu Phe Ser Lys Lys Ser Gln Glu Ile Pro
                    165                 170                 175

Gln Gln Met Asn Gly Ser Asp Cys Gly Met Phe Ala Cys Lys Tyr Ala
                    180                 185                 190

Asp Cys Ile Thr Lys Asp Arg Pro Ile Asn Phe Thr Gln Gln His Met
                    195                 200                 205

Pro Tyr Phe Arg Lys Arg Met Val Trp Glu Ile Leu His Arg Lys Leu
                    210                 215                 220

Leu
225

<210> SEQ ID NO 89
<211> LENGTH: 225
<212> TYPE: PRT
<213> ORGANISM: Homo sapiens

<400> SEQUENCE: 89

Leu Leu Glu Leu Thr Glu Asp Met Glu Lys Glu Ile Ser Asn Ala Leu
1               5                   10                  15

Gly His Gly Pro Gln Asp Glu Ile Leu Ser Ser Ala Phe Lys Leu Arg
                    20                  25                  30

Ile Thr Arg Gly Asp Ile Gln Thr Leu Lys Asn Tyr His Trp Leu Asn
                    35                  40                  45

Asp Glu Val Ile Asn Phe Tyr Met Asn Leu Leu Val Glu Arg Asn Lys
50                  55                  60

Lys Gln Gly Tyr Pro Ala Leu His Val Phe Ser Thr Phe Phe Tyr Pro
65                  70                  75                  80

Lys Leu Lys Ser Gly Gly Tyr Gln Ala Val Lys Arg Trp Thr Lys Gly
                    85                  90                  95

Val Asn Leu Phe Glu Gln Glu Ile Ile Leu Val Pro Ile His Arg Lys
                    100                 105                 110

Val His Trp Ser Leu Val Val Ile Asp Leu Arg Lys Lys Cys Leu Lys
                    115                 120                 125

Tyr Leu Asp Ser Met Gly Gln Lys Gly His Arg Ile Cys Glu Ile Leu
                    130                 135                 140

Leu Gln Tyr Leu Gln Asp Glu Ser Lys Thr Lys Arg Asn Ser Asp Leu
145                 150                 155                 160

Asn Leu Leu Glu Trp Thr His His Ser Met Lys Pro His Glu Ile Pro
                    165                 170                 175

Gln Gln Leu Asn Gly Ser Asp Cys Gly Met Phe Thr Cys Lys Tyr Ala
                    180                 185                 190

Asp Tyr Ile Ser Arg Asp Lys Pro Ile Thr Phe Thr Gln His Gln Met
                    195                 200                 205

Pro Leu Phe Arg Lys Lys Met Val Trp Glu Ile Leu His Gln Gln Leu
```

Leu
225

<210> SEQ ID NO 90
<211> LENGTH: 218
<212> TYPE: PRT
<213> ORGANISM: Homo sapiens

<400> SEQUENCE: 90

Arg Lys Gly Leu Val Leu Gln Leu Ile Gln Ser Tyr Gln Arg Met Pro
1               5                   10                  15

Gly Asn Ala Met Val Arg Gly Phe Arg Val Ala Tyr Lys Arg His Val
            20                  25                  30

Leu Thr Met Asp Asp Leu Gly Thr Leu Tyr Gly Gln Asn Trp Leu Asn
        35                  40                  45

Asp Gln Val Met Asn Met Tyr Gly Asp Leu Val Met Asp Thr Val Pro
    50                  55                  60

Glu Lys Val His Phe Phe Asn Ser Phe Phe Tyr Asp Lys Leu Arg Thr
65                  70                  75                  80

Lys Gly Tyr Asp Gly Val Lys Arg Trp Thr Lys Asn Val Asp Ile Phe
                85                  90                  95

Asn Lys Glu Leu Leu Leu Ile Pro Ile His Leu Glu Val His Trp Ser
            100                 105                 110

Leu Ile Ser Val Asp Val Arg Arg Thr Ile Thr Tyr Phe Asp Ser
        115                 120                 125

Gln Arg Thr Leu Asn Arg Arg Cys Pro Lys His Ile Ala Lys Tyr Leu
    130                 135                 140

Gln Ala Glu Ala Val Lys Lys Asp Arg Leu Asp Phe His Gln Gly Trp
145                 150                 155                 160

Lys Gly Tyr Phe Lys Met Asn Val Ala Arg Gln Asn Asn Asp Ser Asp
                165                 170                 175

Cys Gly Ala Phe Val Leu Gln Tyr Cys Lys His Leu Ala Leu Ser Gln
            180                 185                 190

Pro Phe Ser Phe Thr Gln Gln Asp Met Pro Lys Leu Arg Arg Gln Ile
        195                 200                 205

Tyr Lys Glu Leu Cys His Cys Lys Leu Thr
    210                 215

<210> SEQ ID NO 91
<211> LENGTH: 218
<212> TYPE: PRT
<213> ORGANISM: Homo sapiens

<400> SEQUENCE: 91

Phe Ser Asn Arg Lys Pro Phe Ile Asn Arg Glu Ile Thr Asn Tyr Arg
1               5                   10                  15

Ala Arg His Gln Lys Cys Asn Phe Arg Ile Phe Tyr Asn Lys His Met
            20                  25                  30

Leu Asp Met Asp Asp Leu Ala Thr Leu Asp Gly Gln Asn Trp Leu Asn
        35                  40                  45

Asp Gln Val Ile Asn Met Tyr Gly Glu Leu Ile Met Asp Ala Val Pro
    50                  55                  60

Asp Lys Val His Phe Phe Asn Ser Phe Phe His Arg Gln Leu Val Thr
65                  70                  75                  80

Lys Gly Tyr Asn Gly Val Lys Arg Trp Thr Lys Lys Val Asp Leu Phe
                85                  90                  95

```
Lys Lys Ser Leu Leu Leu Ile Pro Ile His Leu Glu Val His Trp Ser
            100                 105                 110
Leu Ile Thr Val Thr Leu Ser Asn Arg Ile Ile Ser Phe Tyr Asp Ser
            115                 120                 125
Gln Gly Ile His Phe Lys Phe Cys Val Glu Asn Ile Arg Lys Tyr Leu
            130                 135                 140
Leu Thr Glu Ala Arg Glu Lys Asn Arg Pro Glu Phe Leu Gln Gly Trp
145                 150                 155                 160
Gln Thr Ala Val Thr Lys Cys Ile Pro Gln Gln Lys Asn Asp Ser Asp
                    165                 170                 175
Cys Gly Val Phe Val Leu Gln Tyr Cys Lys Cys Leu Ala Leu Glu Gln
                    180                 185                 190
Pro Phe Gln Phe Ser Gln Glu Asp Met Pro Arg Val Arg Lys Arg Ile
                    195                 200                 205
Tyr Lys Glu Leu Cys Glu Cys Arg Leu Met
            210                 215
```

<210> SEQ ID NO 92
<211> LENGTH: 436
<212> TYPE: PRT
<213> ORGANISM: Homo sapiens

<400> SEQUENCE: 92

```
Gly Glu Asn His Thr Ile Phe Ile Gly Pro Val Lys Leu Ile Val
1               5                   10                  15
Tyr Pro Pro Pro Pro Ala Lys Gly Gly Ile Ser Val Thr Asn Glu Asp
                    20                  25                  30
Leu His Cys Leu Asn Glu Gly Glu Phe Leu Asn Asp Val Ile Ile Asp
                    35                  40                  45
Phe Tyr Leu Lys Tyr Leu Val Leu Glu Lys Lys Lys Glu Asp Ala
                    50                  55                  60
Asp Arg Ile His Ile Phe Ser Ser Phe Phe Tyr Lys Arg Leu Asn Gln
65                  70                  75                  80
Arg Glu Arg Arg Asn His Glu Thr Thr Asn Leu Ser Ile Gln Gln Lys
                    85                  90                  95
Arg His Gly Arg Val Lys Thr Trp Thr Arg His Val Asp Ile Phe Glu
                    100                 105                 110
Lys Asp Phe Ile Phe Val Pro Leu Asn Glu Ala Ala His Trp Phe Leu
                    115                 120                 125
Ala Val Val Cys Phe Pro Gly Leu Glu Lys Pro Lys Tyr Glu Pro Asn
                    130                 135                 140
Pro His Tyr His Glu Asn Ala Val Ile Gln Lys Cys Ser Thr Val Glu
145                 150                 155                 160
Asp Ser Cys Ile Ser Ser Ser Ala Ser Glu Met Glu Ser Cys Ser Gln
                    165                 170                 175
Asn Ser Ser Ala Lys Pro Val Ile Lys Lys Met Leu Asn Lys Lys His
                    180                 185                 190
Cys Ile Ala Val Ile Asp Ser Asn Pro Gly Gln Glu Glu Ser Asp Pro
                    195                 200                 205
Arg Tyr Lys Arg Asn Ile Cys Ser Val Lys Tyr Ser Val Lys Ile
            210                 215                 220
Asn His Thr Ala Ser Glu Asn Glu Glu Phe Lys Gly Glu Ser Thr
225                 230                 235                 240
Ser Gln Lys Val Ala Asp Arg Thr Lys Ser Glu Asn Gly Leu Gln Asn
                    245                 250                 255
```

```
Glu Ser Leu Ser Ser Thr His His Thr Asp Gly Leu Ser Lys Ile Arg
            260                 265                 270

Leu Asn Tyr Ser Asp Glu Ser Pro Glu Ala Gly Lys Met Leu Glu Asp
            275                 280                 285

Glu Leu Val Asp Phe Ser Asp Gln Asp Asn Gln Asp Asp Ser Ser
        290                 295                 300

Asp Asp Gly Phe Leu Ala Asp Asp Asn Cys Ser Ser Glu Ile Gly Gln
305                 310                 315                 320

Trp His Leu Lys Pro Thr Ile Cys Lys Gln Pro Cys Ile Leu Leu Met
            325                 330                 335

Asp Ser Leu Arg Gly Pro Ser Arg Ser Asn Val Val Lys Ile Leu Arg
            340                 345                 350

Glu Tyr Leu Glu Val Glu Trp Glu Val Lys Lys Gly Ser Lys Arg Ser
            355                 360                 365

Phe Ser Lys Asp Val Met Lys Gly Ser Asn Pro Lys Val Pro Gln Gln
            370                 375                 380

Asn Asn Phe Ser Asp Cys Gly Val Tyr Val Leu Gln Tyr Val Glu Ser
385                 390                 395                 400

Phe Phe Glu Asn Pro Ile Leu Ser Phe Glu Leu Pro Met Asn Leu Ala
                405                 410                 415

Asn Trp Phe Pro Pro Arg Met Arg Thr Lys Arg Glu Glu Ile Arg
            420                 425                 430

Asn Ile Ile Leu
        435

<210> SEQ ID NO 93
<211> LENGTH: 301
<212> TYPE: PRT
<213> ORGANISM: Homo sapiens

<400> SEQUENCE: 93

Glu Val Arg His Thr Gly Leu Val Gln Lys Leu Ile Val Tyr Pro Pro
1               5                   10                  15

Pro Pro Thr Lys Gly Gly Leu Gly Val Thr Asn Glu Asp Leu Glu Cys
            20                  25                  30

Leu Glu Glu Gly Glu Phe Leu Asn Asp Val Ile Ile Asp Phe Tyr Leu
        35                  40                  45

Lys Tyr Leu Ile Leu Glu Lys Ala Ser Asp Glu Leu Val Glu Arg Ser
    50                  55                  60

His Ile Phe Ser Ser Phe Phe Tyr Lys Cys Leu Thr Arg Lys Glu Asn
65                  70                  75                  80

Asn Leu Thr Glu Asp Asn Pro Asn Leu Ser Met Ala Gln Arg Arg His
                85                  90                  95

Lys Arg Val Arg Thr Trp Thr Arg His Ile Asn Ile Phe Asn Lys Asp
            100                 105                 110

Tyr Ile Phe Val Pro Val Asn Glu Ser Ser His Trp Tyr Leu Ala Val
        115                 120                 125

Ile Cys Phe Pro Trp Leu Glu Glu Ala Val Tyr Glu Asp Phe Pro Gln
    130                 135                 140

Thr Val Ser Gln Gln Ser Gln Ala Gln Ser Gln Asn Asp Asn Lys
145                 150                 155                 160

Thr Ile Asp Asn Asp Leu Arg Thr Thr Ser Thr Leu Ser Leu Ser Ala
                165                 170                 175

Glu Asp Ser Gln Ser Thr Glu Ser Asn Met Ser Val Pro Lys Lys Met
            180                 185                 190
```

```
Cys Lys Arg Pro Cys Ile Leu Ile Leu Asp Ser Leu Lys Ala Ala Ser
            195                 200                 205

Val Gln Asn Thr Val Gln Asn Leu Arg Glu Tyr Leu Glu Val Glu Trp
    210                 215                 220

Glu Val Lys Leu Lys Thr His Arg Gln Phe Ser Lys Thr Asn Met Val
225                 230                 235                 240

Asp Leu Cys Pro Lys Val Pro Lys Gln Asp Asn Ser Ser Asp Cys Gly
                245                 250                 255

Val Tyr Leu Leu Gln Tyr Val Glu Ser Phe Phe Lys Asp Pro Ile Val
            260                 265                 270

Asn Phe Glu Leu Pro Ile His Leu Glu Lys Trp Phe Pro Arg His Val
        275                 280                 285

Ile Lys Thr Lys Arg Glu Asp Ile Arg Glu Leu Ile Leu
    290                 295                 300

<210> SEQ ID NO 94
<211> LENGTH: 233
<212> TYPE: PRT
<213> ORGANISM: Arabidopsis thaliana

<400> SEQUENCE: 94

Val Pro Leu Ser Arg Glu Glu Thr Ala Val Arg Arg Ala Phe Ser
1               5                   10                  15

Ala Asn Asp Ser Asn Ile Leu Val Thr His Lys Asn Ser Asn Ile Asp
            20                  25                  30

Ile Thr Gly Lys Ile Leu Arg Cys Leu Lys Pro Gly Lys Trp Leu Asn
        35                  40                  45

Asp Glu Val Ile Asn Leu Tyr Met Val Leu Lys Glu Arg Glu Ala
50                  55                  60

Arg Glu Pro Lys Lys Phe Leu Lys Cys His Phe Phe Asn Thr Phe Phe
65                  70                  75                  80

Phe Thr Lys Leu Val Asn Ser Ala Thr Gly Tyr Asn Tyr Gly Ala Val
                85                  90                  95

Arg Arg Trp Thr Ser Met Lys Arg Leu Gly Tyr His Lys Lys Asp Cys
            100                 105                 110

Asp Lys Ile Phe Ile Pro Ile His Met Asn Ile His Trp Thr Leu Ala
        115                 120                 125

Val Ile Asn Ile Lys Asp Gln Lys Phe Gln Tyr Leu Asp Ser Phe Lys
    130                 135                 140

Gly Arg Glu Pro Lys Ile Leu Asp Ala Leu Ala Arg Tyr Phe Val Asp
145                 150                 155                 160

Glu Val Arg Asp Lys Ser Glu Val Asp Leu Asp Val Ser Arg Trp Arg
                165                 170                 175

Gln Glu Phe Val Gln Asp Leu Pro Met Gln Arg Asn Gly Phe Asp Cys
            180                 185                 190

Gly Met Phe Met Val Lys Tyr Ile Asp Phe Tyr Ser Arg Gly Leu Asp
        195                 200                 205

Leu Cys Phe Thr Gln Glu Gln Met Pro Tyr Phe Arg Ala Arg Thr Ala
    210                 215                 220

Lys Glu Ile Leu Gln Leu Lys Ala Glu
225                 230

<210> SEQ ID NO 95
<211> LENGTH: 240
<212> TYPE: PRT
<213> ORGANISM: Arabidopsis thaliana
```

<400> SEQUENCE: 95

```
Val Asp Ala Met Gln Asp Leu Ala Leu Val Asn Ser Ala Leu Ser Lys
 1               5                  10                  15
Arg Asn Arg Lys Lys Ile Leu Val Ser His Lys Asn Ser Asn Ile Asp
            20                  25                  30
Ile Ser Gly Glu Thr Leu Gln Cys Leu Arg Pro Asn Gln Trp Leu Asn
        35                  40                  45
Asp Val Thr Asn Leu Tyr Leu Glu Leu Leu Lys Glu Arg Gln Thr
    50                  55                  60
Arg Asp Pro Gln Lys Tyr Phe Lys Cys His Phe Asn Thr Phe Phe
 65                  70                  75                  80
Tyr Val Lys Leu Val Ser Gly Ser Gly Tyr Asn Tyr Lys Ala Val Ser
                85                  90                  95
Arg Trp Thr Thr Lys Arg Lys Leu Gly Tyr Asp Leu Ile Asp Cys Asp
            100                 105                 110
Ile Ile Phe Val Pro Ile His Ile Asp Ile His Trp Thr Leu Gly Val
        115                 120                 125
Ile Asn Asn Arg Glu Arg Lys Phe Val Tyr Leu Asp Ser Leu Phe Thr
    130                 135                 140
Gly Val Gly His Thr Ile Leu Asn Ala Met Ala Lys Tyr Leu Val Asp
145                 150                 155                 160
Glu Val Lys Gln Lys Ser Gln Lys Asn Ile Asp Val Ser Ser Trp Gly
                165                 170                 175
Met Glu Tyr Val Glu Glu Arg Pro Gln Gln Asn Gly Tyr Asp Cys
            180                 185                 190
Gly Met Phe Met Leu Lys Tyr Ile Asp Phe Tyr Ser Arg Gly Leu Ser
        195                 200                 205
Leu Gln Phe Ser Gln Val Ile Arg Asp Val Ile Lys Lys Asp Met Pro
    210                 215                 220
Tyr Phe Arg Leu Arg Thr Ala Lys Glu Ile Leu Arg Leu Arg Ala Asp
225                 230                 235                 240
```

<210> SEQ ID NO 96
<211> LENGTH: 261
<212> TYPE: PRT
<213> ORGANISM: Arabidopsis thaliana

<400> SEQUENCE: 96

```
Met Val Val Glu Glu Ala Cys Glu Leu Pro Glu Gly Leu Pro Glu Asp
 1               5                  10                  15
Ile Tyr Tyr Pro Ser Ser Asp Gln Ser Asp Gly Arg Asp Leu Val Gln
            20                  25                  30
Val Ser Leu Lys Asp Leu Lys Cys Leu Ser Pro Gly Glu Tyr Leu Thr
        35                  40                  45
Ser Pro Val Ile Asn Phe Tyr Ile Arg Tyr Val Gln His His Val Phe
    50                  55                  60
Ser Ala Asp Lys Thr Ala Ala Asn Cys His Phe Phe Asn Thr Phe Phe
 65                  70                  75                  80
Tyr Lys Lys Leu Thr Glu Ala Val Ser Tyr Lys Gly Asn Asp Arg Asp
                85                  90                  95
Ala Tyr Phe Val Lys Phe Arg Arg Trp Trp Lys Gly Phe Asp Leu Phe
            100                 105                 110
Cys Lys Ser Tyr Ile Phe Ile Pro Ile His Glu Asp Leu His Trp Ser
        115                 120                 125
```

```
Leu Val Ile Ile Cys Ile Pro Asp Lys Glu Asp Ser Gly Leu Thr
    130                 135                 140
Ile Ile His Leu Asp Ser Leu Gly Leu His Pro Arg Asn Leu Ile Phe
145                 150                 155                 160
Asn Asn Val Lys Arg Phe Leu Arg Glu Glu Trp Asn Tyr Leu Asn Gln
                165                 170                 175
Asp Ala Pro Leu Asp Leu Pro Ile Ser Ala Lys Val Trp Arg Asp Leu
            180                 185                 190
Pro Asn Met Ile Asn Glu Ala Glu Val Gln Val Pro Gln Gln Lys Asn
        195                 200                 205
Asp Phe Asp Cys Gly Leu Phe Leu Leu Phe Phe Ile Arg Arg Phe Ile
    210                 215                 220
Glu Glu Ala Pro Gln Arg Leu Thr Leu Gln Asp Leu Lys Met Ile His
225                 230                 235                 240
Lys Lys Trp Phe Lys Pro Glu Glu Ala Ser Ala Leu Arg Ile Lys Ile
                245                 250                 255
Trp Asn Ile Leu Val
            260

<210> SEQ ID NO 97
<211> LENGTH: 259
<212> TYPE: PRT
<213> ORGANISM: Arabidopsis thaliana

<400> SEQUENCE: 97

Thr Val Ala Glu Gln Ala Ala Glu Leu Pro Glu Gly Leu Gln Glu Asp
1               5                   10                  15
Ile Cys Tyr Pro Thr Arg Asp Asp Pro His Phe Val Gln Val Cys Leu
            20                  25                  30
Lys Asp Leu Glu Cys Leu Ala Pro Arg Glu Tyr Leu Thr Ser Pro Val
        35                  40                  45
Met Asn Phe Tyr Met Arg Phe Leu Gln Gln Ile Ser Ser Ser Asn
    50                  55                  60
Gln Ile Ser Ala Asp Cys His Phe Phe Asn Thr Tyr Phe Tyr Lys Lys
65                  70                  75                  80
Leu Ser Asp Ala Val Thr Tyr Lys Gly Asn Asp Lys Asp Ala Phe Phe
                85                  90                  95
Val Arg Phe Arg Arg Trp Trp Lys Gly Ile Asp Leu Phe Arg Lys Ala
            100                 105                 110
Tyr Ile Phe Ile Pro Ile His Glu Asp Leu His Trp Ser Leu Val Ile
        115                 120                 125
Val Cys Ile Pro Asp Lys Lys Asp Glu Ser Gly Leu Thr Ile Leu His
    130                 135                 140
Leu Asp Ser Leu Gly Leu His Ser Arg Lys Ser Ile Val Glu Asn Val
145                 150                 155                 160
Lys Arg Phe Leu Lys Asp Glu Trp Asn Tyr Leu Asn Gln Asp Asp Tyr
                165                 170                 175
Ser Leu Asp Leu Pro Ile Ser Glu Lys Val Trp Lys Asn Leu Pro Arg
            180                 185                 190
Arg Ile Ser Glu Ala Val Val Gln Val Pro Gln Gln Lys Asn Asp Phe
        195                 200                 205
Asp Cys Gly Pro Phe Val Leu Phe Phe Ile Lys Arg Phe Ile Glu Glu
    210                 215                 220
Ala Pro Gln Arg Leu Lys Arg Lys Asp Leu Gly Met Phe Asp Lys Lys
225                 230                 235                 240
```

```
Trp Phe Arg Pro Asp Glu Ala Ser Ala Leu Arg Ile Lys Ile Arg Asn
                245                 250                 255

Thr Leu Ile

<210> SEQ ID NO 98
<211> LENGTH: 232
<212> TYPE: PRT
<213> ORGANISM: Arabidopsis thaliana

<400> SEQUENCE: 98

Pro Leu Thr Glu Asp Glu Glu Ala Glu Val Tyr Arg Ala Phe Ser Gly
1               5                   10                  15

Arg Asn Arg Arg Lys Val Leu Ala Thr His Glu Asn Ser Asn Ile Asp
            20                  25                  30

Ile Thr Gly Glu Val Leu Gln Cys Leu Thr Pro Ser Ala Trp Leu Asn
        35                  40                  45

Asp Glu Val Ile Asn Val Tyr Leu Glu Leu Leu Lys Glu Arg Glu Thr
    50                  55                  60

Arg Glu Pro Lys Lys Tyr Leu Lys Cys His Tyr Phe Asn Thr Phe Phe
65                  70                  75                  80

Tyr Lys Lys Leu Val Ser Asp Ser Gly Tyr Asn Phe Lys Ala Val Arg
                85                  90                  95

Arg Trp Thr Thr Gln Arg Lys Leu Gly Tyr Ala Leu Ile Asp Cys Asp
            100                 105                 110

Met Ile Phe Val Pro Ile His Arg Gly Val His Trp Thr Leu Ala Val
        115                 120                 125

Ile Asn Asn Arg Glu Ser Lys Leu Leu Tyr Leu Asp Ser Leu Asn Gly
    130                 135                 140

Val Asp Pro Met Ile Leu Asn Ala Leu Ala Lys Tyr Met Gly Asp Glu
145                 150                 155                 160

Ala Asn Glu Lys Ser Gly Lys Lys Ile Asp Ala Asn Ser Trp Asp Met
                165                 170                 175

Glu Phe Val Glu Asp Leu Pro Gln Gln Lys Asn Gly Tyr Asp Cys Gly
            180                 185                 190

Met Phe Met Leu Lys Tyr Ile Asp Phe Phe Ser Arg Gly Leu Gly Leu
        195                 200                 205

Cys Phe Ser Gln Glu His Met Pro Tyr Phe Arg Leu Arg Thr Ala Lys
    210                 215                 220

Glu Ile Leu Arg Leu Arg Ala Asp
225                 230

<210> SEQ ID NO 99
<211> LENGTH: 227
<212> TYPE: PRT
<213> ORGANISM: Xanthomonas campestris

<400> SEQUENCE: 99

Glu Tyr Pro Asn Asn His Gly Thr Gln Thr Pro Met Gly Tyr Ser Ala
1               5                   10                  15

Met Thr Pro Glu Arg Ile Asp Val Asp Asn Leu Pro Ser Pro Gln Asp
            20                  25                  30

Val Ala Asp Pro Glu Leu Pro Pro Val Arg Ala Thr Ser Trp Leu Leu
        35                  40                  45

Asp Gly His Leu Arg Ala Tyr Thr Asp Leu Ala Arg Arg Leu Arg
    50                  55                  60

Gly Glu Pro Asn Ala His Leu Leu His Phe Ala Asp Ser Gln Val Val
65                  70                  75                  80
```

```
Thr Met Leu Ser Ser Ala Asp Pro Asp Gln Gln Ala Arg Ala Gln Arg
                85                  90                  95

Leu Leu Ala Gly Asp Asp Ile Pro Pro Ile Val Phe Leu Pro Ile Asn
                100                 105                 110

Gln Pro Asn Ala His Trp Ser Leu Leu Val Val Asp Arg Arg Asn Lys
                115                 120                 125

Asp Ala Val Ala Ala Tyr His Tyr Asp Ser Met Ala Gln Lys Asp Pro
            130                 135                 140

Gln Gln Arg Tyr Leu Ala Asp Met Ala Ala Tyr His Leu Gly Leu Asp
145                 150                 155                 160

Tyr Gln Gln Thr His Glu Met Pro Ile Ala Ile Gln Ser Asp Gly Tyr
                165                 170                 175

Ser Cys Gly Asp His Val Leu Thr Gly Ile Glu Val Leu Ala His Arg
                180                 185                 190

Val Leu Asp Gly Thr Phe Asp Tyr Ala Gly Gly Arg Asp Leu Thr Asp
            195                 200                 205

Ile Glu Pro Asp Arg Gly Leu Ile Arg Asp Arg Leu Ala Gln Ala Glu
210                 215                 220

Gln Ala Pro
225

<210> SEQ ID NO 100
<211> LENGTH: 225
<212> TYPE: PRT
<213> ORGANISM: Xenopus laevis

<400> SEQUENCE: 100

Phe Pro Glu Ile Thr Glu Val Met Glu Arg Glu Ile Lys Arg Ala Leu
1               5                   10                  15

Phe Gly Gly Ser Gln Asp Gln Ser Leu Ser Glu Gly Tyr Arg Leu Thr
                20                  25                  30

Ile Thr Arg Lys Asp Ile Met Thr Leu His Ser Leu Asn Trp Leu Asn
            35                  40                  45

Asp Glu Ile Ile Asn Phe Tyr Met Asn Leu Leu Met Glu Arg Ser Lys
50                  55                  60

Arg Lys Gly Leu Pro Thr Val His Ala Phe Asn Thr Phe Phe Phe Thr
65                  70                  75                  80

Lys Leu Lys Ser Ala Gly Tyr Gln Ala Val Lys Arg Trp Thr Lys Lys
                85                  90                  95

Val Asp Ile Phe Ser Met Asn Ile Leu Leu Val Pro Ile His Leu Gly
                100                 105                 110

Val His Trp Cys Leu Ala Val Val Asp Leu Arg Lys Lys Ser Ile Thr
            115                 120                 125

Tyr Phe Asp Ser Met Gly Gly Leu Asn Asn Asp Ala Cys Arg Ile Leu
130                 135                 140

Leu Gln Tyr Leu Lys Gln Glu Ser Val Asp Lys Lys Gly Ala Cys Phe
145                 150                 155                 160

Asp Ser Asn Gly Trp Thr Leu Thr Cys Lys Thr Ser Glu Glu Ile Pro
                165                 170                 175

Gln Gln Met Asn Gly Ser Asp Cys Gly Met Phe Ala Cys Lys Tyr Ala
                180                 185                 190

Asp Tyr Ile Thr Lys Asp Lys Ser Ile Thr Phe Thr Gln His His Met
            195                 200                 205

Pro Tyr Phe Arg Lys Arg Met Val Trp Glu Ile Leu His Gln Lys Leu
210                 215                 220
```

Leu
225

<210> SEQ ID NO 101
<211> LENGTH: 226
<212> TYPE: PRT
<213> ORGANISM: Drosophila melanogaster

<400> SEQUENCE: 101

Lys Leu Ile Pro Leu Thr Lys Glu Asp His Ala Arg Phe Gln Glu Met
1               5                   10                  15

Thr Thr Ile Glu Val Thr Thr Asn Leu Ile Phe Lys Tyr Asn Leu Gln
            20                  25                  30

Ile Thr Thr Asp Asp Ile Phe Thr Phe Val Asp Gly Glu Trp Leu Asn
        35                  40                  45

Asp Ala Ile Ile Asn Phe Tyr Met Ser Met Leu Thr Glu Arg Ser Glu
    50                  55                  60

Lys Arg Ala Gly Glu Leu Pro Ala Thr Tyr Ala Met Asn Thr Phe Phe
65                  70                  75                  80

Met Pro Arg Leu Leu Gln Ala Gly Tyr Ala Gly Val Arg Arg Trp Thr
                85                  90                  95

Arg Lys Val Asp Leu Phe Ser Lys Asp Ile Ile Pro Val Pro Val His
            100                 105                 110

Cys Gly Asn Val His Trp Cys Met Ala Ile Ile His Leu Arg Asn Lys
        115                 120                 125

Thr Ile Phe Tyr Tyr Asp Ser Met Gly Arg Pro Asn Gln Pro Ala Leu
    130                 135                 140

Asp Ala Leu Val Lys Tyr Leu His Glu Glu Ser Leu Asp Lys Arg Lys
145                 150                 155                 160

Gln Pro Phe Asp Met Thr Gly Phe Val Val Glu Asn Ala Gln Asn Ile
                165                 170                 175

Pro Arg Gln Gly Asn Ser Ser Asp Cys Gly Val Phe Ser Cys Met Phe
            180                 185                 190

Ala Glu Tyr Ile Thr Arg Asp Val Pro Ile Thr Phe Ser Gln Ala Glu
        195                 200                 205

Met Leu Tyr Phe Arg Thr Lys Met Ala Leu Glu Ile Ala Asp Gly Lys
    210                 215                 220

Leu Trp
225

<210> SEQ ID NO 102
<211> LENGTH: 224
<212> TYPE: PRT
<213> ORGANISM: Caenorhabditis elegans

<400> SEQUENCE: 102

Phe Met Ala Leu Pro Asp Ala Ala Asp Ala Leu Val Glu Arg Ala Trp
1               5                   10                  15

Ser Gly Gly Asn Pro Asn Glu Gln Phe Val Asp Ala Phe Ser Ile Gln
            20                  25                  30

Ile Cys Lys Lys Asp Leu Ala Thr Leu Ser Gly Leu His Trp Leu Asn
        35                  40                  45

Asp Glu Ile Ile Asn Phe Tyr Leu Gln Leu Ile Cys Asp Arg Ser Asn
    50                  55                  60

Gly Asp Ser Lys Tyr Pro Lys Ile Tyr Ala Phe Asn Thr Phe Phe Tyr
65                  70                  75                  80

```
Ser Asn Ile Val Ser Lys Gly Tyr Ala Ser Val Lys Arg Trp Thr Arg
                85                  90                  95

Lys Val Asp Ile Phe Ala Phe Asp Ile Val Leu Val Pro Val His Leu
            100                 105                 110

Gly Met His Trp Cys Met Ala Val Ile Asp Met Gly Glu Lys Lys Ile
            115                 120                 125

Glu Phe Tyr Asp Ser Leu Tyr Asp Gly Asn Thr Ala Val Leu Pro Ala
            130                 135                 140

Leu Arg Gly Tyr Leu Glu Ala Glu Ser Leu Asp Lys Lys Thr Ala
145                 150                 155                 160

Met Asn Phe Ser Gly Trp Thr Ile Gln Gln Met Thr Asp Ile Pro Arg
            165                 170                 175

Gln Gln Asn Gly Ser Asp Cys Gly Val Phe Ser Cys Gln Phe Gly Glu
            180                 185                 190

Trp Ala Ser Arg Arg Thr Thr Pro Arg Phe Thr Gln Lys Asn Met Pro
            195                 200                 205

Tyr Tyr Arg Lys Arg Met Val Tyr Glu Ile Val Ser Lys Lys Leu Leu
            210                 215                 220

<210> SEQ ID NO 103
<211> LENGTH: 284
<212> TYPE: PRT
<213> ORGANISM: Caenorhabditis elegans

<400> SEQUENCE: 103

Pro Thr Arg Pro Val Val Glu Lys Ile Pro Asp Thr Gln Leu Phe
1               5                  10                  15

Thr Phe Pro Pro Ser Gly Ser Cys Thr Thr Gly Met Asp Pro Val Val
            20                  25                  30

Leu Leu Val Lys Asp Ile Lys Thr Leu Asp Arg Lys Glu Phe Leu Asn
            35                  40                  45

Asp Ser Val Met Ala Phe Met Leu Asn Tyr Ile Ala Phe Met Leu Ser
        50                  55                  60

Ser Glu Leu Met Lys Ser Val His Met Cys Asn Thr Phe Leu Phe Val
65                  70                  75                  80

Asn Leu Thr Arg Leu Leu Pro Pro Leu Cys Phe Ser Lys Arg Arg Pro
                85                  90                  95

Ile Glu Pro Glu His Ile Lys Ile Val Lys Asp Asn Cys Pro Arg Val
            100                 105                 110

Leu Arg Trp Thr Arg Lys Phe Asp Val Leu Ala Lys Asp Tyr Ile Ile
            115                 120                 125

Ile Pro Ile Asn Glu Asp Leu His Trp Leu Val Ile Ala Val Ile Asn
            130                 135                 140

Pro Ser Gly Ala Ile Val Asp Met Ser Asn Glu Glu Ala Ser Arg Ala
145                 150                 155                 160

Ala Pro Lys Cys Tyr Ile Val Phe Phe Asp Pro Leu Ser Gly Leu Asp
            165                 170                 175

Pro Ser Lys Lys Asn His Met Cys His Cys Ile Lys Ile Tyr Leu Ala
            180                 185                 190

Gln Leu Tyr Glu Asn Thr Lys Ala Pro Gly Met Lys Phe Ala Ser Lys
            195                 200                 205

Asn Pro Thr Ile Tyr Asp Glu Glu Arg Val Val Thr Arg Ala Glu
            210                 215                 220

Asn Thr Pro Ile Gln Asp Asn Phe Tyr Asp Cys Gly Leu Tyr Val Leu
225                 230                 235                 240
```

```
His Phe Ile Glu Gly Leu Phe Cys Tyr Pro Asn Arg Pro Val Asn Val
                245                 250                 255

Asn Asp Phe Pro Asn Phe Asp Trp Ser Lys Phe Phe Pro Glu Ala Asn
            260                 265                 270

Lys Met Cys Asp Leu Met Arg Asp Lys Val Tyr Asn
        275                 280
```

<210> SEQ ID NO 104
<211> LENGTH: 222
<212> TYPE: PRT
<213> ORGANISM: Schizosaccharomyces pombe

<400> SEQUENCE: 104

```
Phe Pro Asp Asn Ala Arg Lys Arg Ala Leu Lys Tyr Leu Asn Gln Ser
1               5                   10                  15

Asn Ser Val Ser Ser Glu Pro Ile Ile Thr Lys Phe Asn Ile Pro
            20                  25                  30

Ile Thr Leu Lys Asp Leu His Thr Leu Arg Asn Arg Gln Trp Leu Asn
        35                  40                  45

Asp Glu Val Ile Asn Phe Tyr Met Asn Leu Ile Ser Glu Arg Ser Lys
50                  55                  60

Ile Asp Ser Ser Leu Pro Arg Val His Gly Phe Asn Thr Phe Phe Tyr
65                  70                  75                  80

Thr Ser Leu Gln Arg Arg Gly Tyr Ala Gly Val Arg Arg Trp Ala Lys
                85                  90                  95

Lys Ala Arg Val Asn Ile Ala Asp Met Asp Ala Val Phe Ile Pro Val
            100                 105                 110

His Leu Asp Val His Trp Cys Met Ala Val Ile Asn Lys Ser Lys Lys
        115                 120                 125

Arg Phe Glu Tyr Trp Asp Ser Leu Ala Gly Ser Pro Gly Lys Val Phe
    130                 135                 140

Asp Leu Leu Arg Asp Tyr Tyr Ile Ala Glu Thr Lys Gly Ala Val Asp
145                 150                 155                 160

Val Ser Asp Trp Glu Asn Phe Met Asp Asp Asn Ser Pro Arg Gln Arg
                165                 170                 175

Asn Gly His Asp Cys Gly Val Phe Ala Cys Lys Thr Ala Glu Cys Val
            180                 185                 190

Ser Arg Asn Val Pro Val Gln Phe Ser Gln Asn Asp Met Pro Glu Leu
        195                 200                 205

Arg Ile Lys Met Ala Ala Ser Ile Ile Asp Ala Gln Ile Tyr
    210                 215                 220
```

<210> SEQ ID NO 105
<211> LENGTH: 269
<212> TYPE: PRT
<213> ORGANISM: Schizosaccharomyces pombe

<400> SEQUENCE: 105

```
Thr Leu Cys Ser Gln Gly Ser Asp Lys Thr Leu Leu Ser Asp Ala Ser
1               5                   10                  15

Cys Thr Thr Ile Leu Val Tyr Pro Phe Ser Gly Thr Asn Ser Ile Ala
            20                  25                  30

Ile Thr Asn Thr Asp Leu Thr Arg Leu Asn Glu Gly Glu Phe Leu Asn
        35                  40                  45

Asp Thr Ile Val Asp Phe Tyr Leu Arg Tyr Leu Tyr Cys Lys Leu Gln
50                  55                  60

Thr Gln Asn Pro Ser Leu Ala Asn Asp Thr His Ile Phe Asn Thr Phe
```

```
                65                  70                  75                  80
Phe Tyr Asn Arg Leu Thr Ser Lys Asp Lys Asp Gly Lys Arg Leu Gly
                    85                  90                  95

His Arg Gly Val Arg Lys Trp Thr Gln Lys Val Asp Leu Phe His Lys
                100                 105                 110

Lys Tyr Ile Ile Val Pro Ile Asn Glu Thr Phe His Trp Tyr Leu Ala
                115                 120                 125

Ile Ile Cys Asn Ile Asp Arg Leu Met Pro Val Asp Thr Lys Leu Glu
            130                 135                 140

Glu Gln Asp Glu Ile Val Met Ser Ser Val Glu Gln Pro Ser Ala Ser
145                 150                 155                 160

Lys Thr Arg Gln Ala Glu Leu Thr Ser Asn Ser Pro Ala Ile Leu Ile
                165                 170                 175

Phe Asp Ser Leu Ala Asn Leu His Lys Gly Ala Leu Asn Tyr Leu Arg
                180                 185                 190

Glu Tyr Leu Leu Glu Ala Phe Glu Arg Lys Asn Val His Leu Lys
                195                 200                 205

Ser Thr Asp Ile Arg Gly Phe His Ala Lys Val Pro Gln Gln Ser Asn
            210                 215                 220

Phe Ser Asp Cys Gly Ile Tyr Ala Leu His Phe Val Glu Leu Phe Leu
225                 230                 235                 240

Glu Thr Pro Glu Gln Val Ile Ala Asn Thr Leu Asp Lys Ser Leu Arg
                245                 250                 255

Arg Thr Asp Ala Lys Asn Phe Asp Gln Gln Trp Asn Leu
                260                 265

<210> SEQ ID NO 106
<211> LENGTH: 216
<212> TYPE: PRT
<213> ORGANISM: Kluyveromyces lactis

<400> SEQUENCE: 106

Leu Ile Pro Asp Leu Ser Thr Glu Asp Leu Ser Glu Val Lys Ala Thr
1               5                   10                  15

Phe Asn Arg Ser Asp Asn Ala Val Leu Ser Ser Lys Tyr Met Leu Glu
                20                  25                  30

Val Thr Val Arg Asp Phe Lys Thr Leu Ala Pro Arg Arg Trp Leu Asn
            35                  40                  45

Asp Thr Ile Ile Glu Phe Phe Met Lys Tyr Ile Glu Gln Asn Thr Ala
        50                  55                  60

Lys Thr Val Ala Phe Asn Ser Phe Tyr Ser Thr Leu Ala Asp Arg
65              70                  75                  80

Gly Tyr Gln Gly Val Arg Arg Trp Met Lys Arg Lys Lys Val Asp Ile
                85                  90                  95

Leu Asp Leu Asn Lys Ile Phe Val Pro Ile Asn Leu Asn Asp Ser His
                100                 105                 110

Trp Thr Leu Gly Ile Ile Glu Met Lys Gln His Lys Ile Tyr Tyr Leu
            115                 120                 125

Asp Ser Leu Ser Ser Gly Met Asn Ser Val Ser Phe Leu Ile Met Lys
        130                 135                 140

Asn Leu Gln Ser Tyr Val Met Glu Glu Ser Lys Gln Lys Leu Gly Glu
145                 150                 155                 160

Asp Phe Glu Leu Cys His Ile Ala Cys Pro Gln Gln Pro Asn Gly Phe
                165                 170                 175

Asp Cys Gly Ile Tyr Val Cys Leu Asn Thr Leu Tyr Met Ser Lys Asp
```

```
              180                 185                 190
Tyr Thr Leu Ser Phe Asp Ser Lys Asp Ala Ala Asn Met Arg Asn Tyr
        195                 200                 205

Ile Gly His Leu Ile Leu Ser Lys
    210                 215

<210> SEQ ID NO 107
<211> LENGTH: 231
<212> TYPE: PRT
<213> ORGANISM: Plasmodium falciparum

<400> SEQUENCE: 107

Phe Lys Cys Ser Lys Lys Glu Tyr Tyr Glu Lys Ala Ile Ile Ile Leu
1               5                   10                  15

Asn Glu Lys Ile Glu Asn Arg Val Leu Ile Glu Lys Phe Asn Val Pro
            20                  25                  30

Leu Leu Tyr Ser Gln Ile Lys Cys Leu Ile Asp Thr Arg Trp Leu Asn
        35                  40                  45

Asp Glu Val Ile Asn Phe Tyr Leu Ser Met Leu Gln Glu Tyr Asn Glu
    50                  55                  60

Gln His Thr Lys Asn Asn Ser Leu Thr Phe Ile Pro Lys Ile Phe Thr
65                  70                  75                  80

Phe Ser Thr Phe Phe Gln Ser Leu Asn Phe Asn Gly Ser Tyr Asn
                85                  90                  95

Tyr Ser Lys Val Ser Arg Trp Thr Lys Arg Lys Gln Val Asp Ile Phe
                100                 105                 110

Ser Phe Asp Leu Ile Leu Ile Pro Leu His Val Gly Gly Asn His Trp
        115                 120                 125

Thr Leu Gly Ser Ile His Met Lys Asp Lys Lys Ile Cys Leu Tyr Asp
    130                 135                 140

Ser Leu Asn Gly Ser Asn Lys Lys Phe Phe Glu Tyr Met Arg Arg Tyr
145                 150                 155                 160

Ile Val Asp Glu Met Lys Asp Lys Lys Gln Lys Asp Leu Asp Ile Ser
                165                 170                 175

Leu Trp Thr Tyr Ser Lys Glu Gly Val Ser Glu Lys Gly Ile Pro His
            180                 185                 190

Gln Glu Asn Gly Tyr Asp Cys Gly Val Phe Thr Cys Met Phe Ala Lys
        195                 200                 205

Cys Leu Ser Phe Asn Arg Glu Phe Asp Phe Asn Gln Arg Asp Ile Lys
    210                 215                 220

Asp Ile Arg Leu Lys Met Val
225                 230

<210> SEQ ID NO 108
<211> LENGTH: 238
<212> TYPE: PRT
<213> ORGANISM: Aspergillus nidulans

<400> SEQUENCE: 108

Arg Pro Leu Pro Asp Asn Trp Lys Ala Arg Leu Lys Asp Leu Lys Lys
1               5                   10                  15

Lys Ala His Trp Val Glu Val Ala Thr Thr Pro Ser Gly Glu Ser Leu
            20                  25                  30

Thr Arg Asp Asp Ile Asp Thr Cys Leu Thr Pro Met Ala Trp Leu Asn
        35                  40                  45

Asp Glu Val Ile Asn Ser Tyr Leu Gly Leu Ile Val Asn His Met Arg
    50                  55                  60
```

His Glu Asn Gly Asn Ala Gly Arg His Asp Lys Pro Arg Tyr His Ala
65                  70                  75                  80

Phe Asn Thr Phe Phe Phe Ser Asn Leu Arg Asp Lys Gly Tyr Asp Ser
            85                  90                  95

Val Lys Arg Trp Ala Lys Arg Ala Lys Ile Gly Gly Lys Asp Leu Leu
            100                 105                 110

Asp Val Asp Thr Val Phe Ile Pro Val His Asn Lys Ala His Trp Thr
            115                 120                 125

Leu Ile Val Val Lys Pro Ser Ala Arg Thr Ile Glu His Phe Asp Ser
            130                 135                 140

Leu Gly Ser Leu Ser Arg Arg His Val Glu Thr Val Lys Gly Trp Leu
145                 150                 155                 160

Arg Gly Glu Leu Gly Asp Leu Tyr Asp Asp Glu Trp Glu Val Leu
                165                 170                 175

Pro Ser Glu Ser Pro Gln Gln Asp Asn Gly Ser Asp Cys Gly Val Phe
            180                 185                 190

Leu Leu Thr Thr Ala Lys Ala Val Ala Leu Asn Ile Glu Pro Leu Ala
            195                 200                 205

Tyr Gly Ala Arg Asp Thr Pro Leu Leu Arg Gln Lys Ile Val Ala Glu
210                 215                 220

Leu Ile Asn Gly Gly Phe Glu Gly Asp Phe Thr Pro Asp Gly
225                 230                 235

<210> SEQ ID NO 109
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 7
<223> OTHER INFORMATION: n = a, t, c, or g

<400> SEQUENCE: 109
ggaggtngag acc                                                          13

<210> SEQ ID NO 110
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 7
<223> OTHER INFORMATION: n = a, c, t, or g

<400> SEQUENCE: 110
ggtctcnacc tcc                                                          13

<210> SEQ ID NO 111
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 7
<223> OTHER INFORMATION: n = a, c, t, or g

<400> SEQUENCE: 111

-continued

```
ggtctcnagg t                                                          11

<210> SEQ ID NO 112
<211> LENGTH: 11
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 5
<223> OTHER INFORMATION: n = a, c, t, or g

<400> SEQUENCE: 112
acctngagac c                                                          11

<210> SEQ ID NO 113
<211> LENGTH: 463
<212> TYPE: DNA
<213> ORGANISM: Artificial Sequence
<220> FEATURE:
<223> OTHER INFORMATION: Synthetic sequence

<400> SEQUENCE: 113
agatctcgat cccgcgaaat taatacgact cactataggg gaattgtgag cggataacaa     60
ttcccctcta gaaataattt tgtttaactt taagaaggag atataccatg ggtcatcacc    120
atcatcatca cggaggttcc gaggagaagc ccaaggaggg tgtgaagaca gagaatgacc    180
acatcaacct gaaggtggcc gggcaggacg gctccgtggt gcagttcaag atcaagaggc    240
acacgccgct gagcaagctg atgaaggcct actgcgagag gcagggcttg tcaatgaggc    300
agatcagatt caggttcgac gggcagccaa tcaatgaaac tgacactcca gcacagctgg    360
agatggagga cgaggacacc atcgacgtgt tccagcagca gacgggaggt tgagaccgga    420
tccgaattcg agctccgtcg acaagcttgc ggccgcactc gag                     463
```

We claim:

1. A nucleic acid composition for enhancing expression levels of a protein of interest, comprising, in-frame:
   (a) an isolated nucleic acid sequence which encodes a human SUMO-3 protein, wherein said human SUMO-3 protein is SEQ ID NO: 3;
   (b) an isolated nucleic acid sequence encoding said protein of interest; and
   (c) an isolated nucleic acid sequence encoding at least one purification tag,
   wherein, upon expression in a suitable host cell, said nucleic acid composition produces a fusion protein in which said human SUMO-3 protein is attached to the amino terminal of said protein of interest and said purification tag is N-terminal to said human SUMO-3 protein.

2. The composition of claim 1, wherein said purification tag is selected from the group consisting of polyhistidine tags, polyarginine tags, glutathione-S-transferase, maltose binding protein, S-tag, influenza virus HA tag, thioredoxin, staphylococcal protein A tag, the FLAG™ epitope, AviTag epitope, and the c-myc epitope.

3. The composition of claim 1, wherein said host cell is selected from the group consisting of bacteria, yeast, mammalian cells, and insect cells.

4. An expression vector comprising, in-frame:
   (a) an isolated nucleic acid sequence which encodes a human SUMO-3 protein, wherein said human SUMO-3 protein is SEQ ID NO: 3;
   (b) an isolated nucleic acid sequence encoding a protein of interest; and
   (c) an isolated nucleic acid sequence encoding at least one purification tag,
   wherein, upon expression in a suitable host cell, said expression vector produces a fusion protein in which said human SUMO-3 protein is attached to the amino terminal of said protein of interest and said purification tag is N-terminal to said human SUMO-3 protein.

5. The expression vector of claim 4, wherein said purification tag is selected from the group consisting of polyhistidine tags, polyarginine tags, glutathione-S-transferase, maltose binding protein, S-tag, influenza virus HA tag, thioredoxin, staphylococcal protein A tag, the FLAG™ epitope, AviTag epitope, and the c-myc epitope.

6. The expression vector of claim 4, wherein said host cell is selected from the group consisting of bacteria, yeast, mammalian cells, and insect cells.

7. A method for enhancing expression of a protein of interest, comprising the steps of:
   (a) transforming a host cell with an expression vector comprising:
   (1) a vector which is suitable for transforming a host cell, and
   (2) a nucleic acid insert comprising, in-frame (i) an isolated nucleic acid sequence encoding a human SUMO-3 protein, wherein said human SUMO-3 protein is SEQ ID NO: 3, (ii) an isolated nucleic acid sequence encoding said protein of interest, and (iii) an isolated nucleic acid encoding at least one purification tag, operably linked;

(b) expressing said expression vector in a suitable host cell; and (c) isolating the protein produced by expression of said nucleic acid insert, wherein upon expression in said host cell, said expression vector encodes a fusion protein in which said purification tag is N-terminal to said human SUMO-3 protein, and said human SUMO-3 protein is attached to the amino terminal of the protein of interest.

8. The method of claim 7, wherein said host cell is selected from the group consisting of bacteria, yeast, mammalian cells, and insect cells.

9. The method of claim 7, optionally comprising one or more of the following additional step(s):
   (d) lysing the host cell expressing the fusion protein;
   (e) purifying the fusion protein by way of said at least one purification tag; and
   (f) cleaving the SUMO moiety and purification tag(s) from the protein of interest with human SUMO protease SENP2 encoded by SEQ ID NO: 43, an equivalent thereof, a homologue thereof, a catalytic domain thereof, or a combination thereof.

10. The method of claim 7, wherein said purification tag is selected from the group consisting of polyhistidine tags, polyarginine tags, glutathione-S-transferase, maltose binding protein, S-tag, influenza virus HA tag, thioredoxin, staphylococcal protein A tag, the FLAG™ epitope, AviTag epitope, and the c-myc epitope.

11. The method of claim 7, wherein said protein of interest has a desired native N-terminal amino acid following cleavage with SENP2 protease, and provided that said N-terminal amino acid is not proline.

12. A kit for enhancing expression levels of a protein of interest, comprising:
   (a) a vector which is suitable for transforming a host cell and which has at least one cloning site for cloning a nucleic acid encoding a protein of interest, operably linked to an nucleic acid insert comprising, in-frame, (i) an isolated nucleic acid sequence encoding a human SUMO-3 protein, wherein said human SUMO-3 protein is SEQ ID NO: 3, and (ii) an isolated nucleic acid encoding at least one purification tag,
   wherein said at least one cloning site is oriented in said vector so that upon cloning in a nucleic acid sequence encoding said protein of interest, and expression of said vector in a host cell, said vector encodes a fusion protein in which said purification tag is N-terminal to said human SUMO-3 protein, and said human SUMO-3 protein is attached to the amino terminal of the protein of interest; and
   (b) a cleavage enzyme for cleaving the SUMO moiety and purification tag(s) from the protein of interest, comprising human SUMO protease SENP2 encoded by SEQ ID NO: 43, an equivalent thereof, a homologue thereof, a catalytic domain thereof, or a combination thereof.

13. The kit of claim 12, wherein said purification tag is selected from the group consisting of polyhistidine tags, polyarginine tags, glutathione-S-transferase, maltose binding protein, S-tag, influenza virus HA tag, thioredoxin, staphylococcal protein A tag, the FLAG™ epitope, AviTag epitope, and the c-myc epitope.

14. The kit of claim 12, wherein said host cell is selected from the group consisting of bacteria, yeast, mammalian cells, and insect cells.

15. The kit of claim 12, further comprising:
   i) a solid support resin for binding the purification tag,
   ii) cell lysis buffers,
   iii) wash buffers,
   iv) elution buffers,
   v) SENP2 cleavage buffers,
   vi) an instruction manual, or
   vii) a combination thereof.

16. The kit of claim 12, wherein said protein of interest has a desired native N-terminal amino acid following cleavage with SENP2 protease, and provided that said N-terminal amino acid is not proline.

17. The composition of claim 1, wherein said isolated nucleic acid sequence which encodes a human SUMO-3 protein is SEQ ID NO: 4.

18. The expression vector of claim 4, wherein said isolated nucleic acid sequence which encodes a human SUMO-3 protein is SEQ ID NO: 4.

19. The method of claim 7, wherein said isolated nucleic acid sequence which encodes a human SUMO-3 protein is SEQ ID NO: 4.

20. The kit of claim 12, wherein said isolated nucleic acid sequence which encodes a human SUMO-3 protein is SEQ ID NO: 4.

21. The method of claim 3, wherein said host cell is a yeast cell.

22. The method of claim 6, wherein said host cell is a yeast cell.

23. The method of claim 8, wherein said host cell is a yeast cell.

24. The kit of claim 14, wherein said host cell is a yeast cell.

* * * * *